United States Patent
Liang et al.

(10) Patent No.: US 11,065,257 B2
(45) Date of Patent: Jul. 20, 2021

(54) SUBSTITUTED PYRAZOLOAZEPIN-4-ONES AND THEIR USE AS PHOSPHODIESTERASE INHIBITORS

(71) Applicant: LEO Pharma A/S, Ballerup (DK)

(72) Inventors: Xifu Liang, Ballerup (DK); Jens Larsen, Ballerup (DK); Simon Feldbaek Nielsen, Ballerup (DK); Peter Andersen, Ballerup (DK)

(73) Assignee: LEO Pharma A/S, Ballerup (DK)

( * ) Notice: Subject to any disclaimer, the term of this patent is extended or adjusted under 35 U.S.C. 154(b) by 0 days.

(21) Appl. No.: 16/468,444

(22) PCT Filed: Dec. 12, 2017

(86) PCT No.: PCT/EP2017/082424
§ 371 (c)(1),
(2) Date: Jun. 11, 2019

(87) PCT Pub. No.: WO2018/108910
PCT Pub. Date: Jun. 21, 2018

(65) Prior Publication Data
US 2020/0323869 A1    Oct. 15, 2020

(30) Foreign Application Priority Data
Dec. 12, 2016    (EP) .................................... 16203335

(51) Int. Cl.
*C07D 491/20*    (2006.01)
*A61K 31/55*    (2006.01)

(52) U.S. Cl.
CPC ............ *A61K 31/55* (2013.01); *C07D 491/20* (2013.01)

(58) Field of Classification Search
CPC ............................. C07D 491/20; A61K 31/55
USPC .................................... 540/521; 514/212.02
See application file for complete search history.

(56) References Cited

U.S. PATENT DOCUMENTS

2007/0254915 A1    11/2007    Leleti et al.

FOREIGN PATENT DOCUMENTS

| WO | WO 01/49689 A2 | 7/2001 |
| WO | WO 2004/098520 A2 | 11/2004 |
| WO | WO 2007/040435 A1 | 4/2007 |
| WO | WO 2008/060597 A2 | 5/2008 |

OTHER PUBLICATIONS

Holden, Colin A, B.Sc., et al., "Monocyte Localization of Elevated cAMP Phosphodiesterase Activity in Atopic Dermatitis," The Society for Investigative Dermatology, vol. 87, No. 3, pp. 372-376 (1986).
Houslay, Miles D. et al., "Phosphodiesterase-4 as a therapeutic target," Drug Discovery Today, vol. 1, No. 22, pp. 1503-1519 (2005).
Kroegel, Claus et al., "Phosphodiesterase-4 inhibitors as a novel approach for the treatment of respiratory disease: cilomilast," Exp. Opinion Investig. Drugs, vol. 16, No. 1, pp. 109-124 (2007).
Lipworth, Brian J, "Phosphodiesterase-4 inhibitors for asthma and chronic obstructive pulmonary disease," Lancet, vol. 265, pp. 167-175 (2005).
Smith, Victoria Boswell et la., "Selective phosphodiesterase 4 inhibitors in the treatment of allergy and inflammation," Curr. Opinion Investig. Drugs, vol. 6, No. 11, pp. 1136-1142 (2006).
International Search Report for International Application No. PCT/EP2016/082424, dated Feb. 19, 2018. (2 pages).
Written Opinion of the International Searching Authority for International Application No. PCT/EP2016/082424. (5 pages).

*Primary Examiner* — Jeffrey H Murray
(74) *Attorney, Agent, or Firm* — Finnegan, Henderson, Farabow, Garrett & Dunner, LLP

(57) ABSTRACT

The present invention relates to novel substituted pyrazoloazepin-4-ones with phosphodiesterase inhibitory activity, as well as to their use as therapeutic agents in the treatment of inflammatory diseases and conditions.

9 Claims, No Drawings

SUBSTITUTED PYRAZOLOAZEPIN-4-ONES AND THEIR USE AS PHOSPHODIESTERASE INHIBITORS

FIELD OF THE INVENTION

The present invention relates to novel substituted pyrazoloazepin-4-ones with phosphodiesterase inhibitory activity, and to their use as therapeutic agents in the treatment of inflammatory diseases and conditions.

BACKGROUND OF THE INVENTION

Phosphodiesterases are enzymes that catalyse the hydrolysis of cyclic AMP and/or cyclic GMP in cells to 5-AMP and 5-GMP, respectively, and as such they are critical to cellular regulation of cAMP or cGMP levels. Of the 11 phosphodiesterases identified so far, phosphodiesterase (PDE) 4, PDE7 and PDE8 are selective for cAMP. PDE4 is the most important modulator of cAMP expressed in immune and inflammatory cells such as neutrophils, macrophages and T-lymphocytes. As cAMP is a key second messenger in the modulation of inflammatory responses, PDE4 has been found to regulate inflammatory responses of inflammatory cells by modulating proinflammatory cytokines such as TNF-α, IL-2, IFN-γ, GM-CSF and LTB4. Inhibition of PDE4 has therefore become an attractive target for the therapy of inflammatory diseases such as asthma, chronic obstructive pulmonary disease (COPD), rheumatoid arthritis, atopic dermatitis, psoriasis, inflammatory bowel disease such as Crohn's disease etc. (M. D. Houslay et al., *Drug Discovery Today* 10 (22), 2005, pp. 1503-1519). As atopic dermatitis (AD) patients have increased PDE-activity, PDE4-inhibition would also appear to be a viable treatment of AD (Journal of Investigative Dermatology (1986), 87(3), 372-6).

The PDE4 gene family consists at least of four genes, A, B, C and D, which have a high degree of homology (V. Boswell Smith and D. Spina, *Curr. Opinion Investig. Drugs* 6(11), 2006, pp. 1136-1141). The four PDE4 isoforms are differentially expressed in different tissues and cell types. Thus, PDE4B is predominantly expressed in monocytes and neutrophils, but not in cortex and epithelial cells, while PDE4D is expressed in lung, cortex, cerebellum and T-cells (C. Kroegel and M. Foerster, *Exp. Opinion Investig. Drugs* 16(1), 2007, pp. 109-124). It has been speculated that inhibition of PDE4D in the brain is associated with the adverse effects found when administering PDE4 inhibitors clinically, primarily nausea and emesis, whereas inhibition of PDE4B is associated with anti-inflammatory effects (B. Lipworth, *Lancet* 365, 2005, pp. 167-175).

Numerous PDE4 inhibitors have been studied for their therapeutic effect on inflammatory diseases, primarily asthma and COPD.

WO 2007/040435 (Astrazeneca AB) discloses 5,6-dihydropyrazolo[3,4-e][1,4]diazepin-4(1H)-one derivatives for the treatment of asthma and chronic obstructive pulmonary disease. The compounds are stated to be selective inhibitors of PDE4 over other PDEs.

WO 2001/049689 (Warner-Lambert Company) discloses pyrazolo[3,4-e]diazepines. The compounds are stated to inhibit the PDE4 enzyme.

WO2008/060597 (Vertex Pharmaceuticals Inc) relates to compounds as protein kinase inhibitors.

WO2004/098520 (IRM LLC) relates to compounds as protein kinase inhibitors.

There is a continuous need for developing novel PDE4 inhibitors which have a more favourable therapeutic window, i.e. fewer adverse effects, while retaining their therapeutic effect.

SUMMARY OF THE INVENTION

It is an object of the present invention to provide novel compounds which are PDE4 inhibitors and thereby useful in therapy.

In one aspect the invention provides a compound of general formula (I)

wherein
$R_1$ and $R_4$ are independently selected from the group consisting of hydrogen and $(C_1$-$C_4)$alkyl;
$R_2$ and $R_3$ are independently selected from the group consisting of hydrogen and $(C_1$-$C_4)$alkyl; or
$R_2$ and $R_3$ together with the carbon atom to which they are attached form a cyclopropyl, cyclobutyl, cyclopentyl, oxetanyl, tetrahydrofuranyl, or tetrahydropyranyl ring;
n=0, 1 or 2; and when n is 0, $R_4$ does not exist;
Q is selected from the group consisting of —O—C(O)—$R_5$ and —O—C(O)—$(C_1$-$C_6)$alkyl-$R_5$;
$R_5$ is selected from the group consisting of heteroaryl and heterocycloalkyl, wherein said heteroaryl and heterocycloalkyl are optionally substituted with one or more substituents independently selected from $R_6$;
$R_6$ consists of halogen, cyano, hydroxyl, $(C_1$-$C_4)$alkyl, halo$(C_1$-$C_4)$alkyl, $(C_1$-$C_4)$alkyloxy, —S(O)$_2R_x$, —S(O)$_2$N$R_aR_b$, —O$R_x$, —C(O)NR$_aR_b$, —C(O)OR$_a$, —C(O)R$_a$, cycloalkyl, aryl and heteroaryl;
$R_x$ is $(C_1$-$C_4)$alkyl;
$R_a$ and $R_b$ are independently selected from the group consisting of hydrogen, $(C_1$-$C_4)$-alkyl, phenyl-$(C_1$-$C_4)$alkyl, or
$R_a$ and $R_b$ together with the nitrogen to which they are attached form a 4-6 membered heterocycloalkyl, wherein said heterocycloalkyl is optionally substituted with one or more $(C_1$-$C_4)$alkyl; or
pharmaceutically acceptable salts, hydrates or solvates thereof.

In another aspect, the invention provides pharmaceutical compositions comprising a compound of general formula (I) as defined above together with a pharmaceutically acceptable vehicle or excipient or pharmaceutically acceptable carrier(s), optionally together with one or more other therapeutically active compound(s).

In another aspect, the invention provides the use of a compound of the invention, for the manufacture of pharmaceutical compositions for the prophylaxis, treatment, prevention or amelioration of a disease, disorder or condition responsive to PDE4 inhibitory activity.

In yet another aspect the invention provides a method for treatment, prevention or alleviation of diseases, disorders or conditions responsive to PDE4 inhibitory activity, and which method comprises the step of administering to a living animal body a therapeutically effective amount of the compound of formula (I) of the invention.

Other objects of the invention will be apparent to the person skilled in the art from the following detailed description and examples.

DETAILED DESCRIPTION OF THE INVENTION

In one aspect the invention provides a compound of general formula (I)

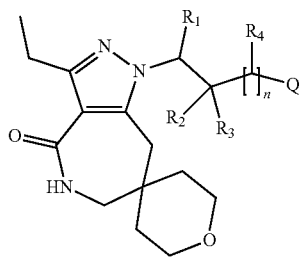

wherein $R_1$ and $R_4$ are independently selected from the group consisting of hydrogen and $(C_1-C_4)$alkyl;

$R_2$ and $R_3$ are independently selected from the group consisting of hydrogen and $(C_1-C_4)$alkyl; or $R_2$ and $R_3$ together with the carbon atom to which they are attached form a cyclopropyl, cyclobutyl, cyclopentyl, oxetanyl, tetrahydrofuranyl, or tetrahydropyranyl ring;

n=0, 1 or 2; and when n is 0, $R_4$ does not exist;

Q is selected from the group consisting of —O—C(O)—$R_5$ and —C(O)—$(C_1-C_6)$alkyl-$R_5$;

$R_5$ is selected from the group consisting of heteroaryl and heterocycloalkyl, wherein said heteroaryl and heterocycloalkyl are optionally substituted with one or more substituents independently selected from $R_6$;

$R_6$ consists of halogen, cyano, hydroxyl, $(C_1-C_4)$alkyl, halo$(C_1-C_4)$alkyl, $(C_1-C_4)$alkyloxy, —S(O)$_2$R$_x$, —S(O)$_2$NR$_a$R$_b$, —OR$_x$, —C(O)NR$_a$R$_b$, —C(O)OR$_a$, —C(O)R$_a$, cycloalkyl, aryl and heteroaryl;

$R_x$ is $(C_1-C_4)$alkyl;

$R_a$ and $R_b$ are independently selected from the group consisting of hydrogen, $(C_1-C_4)$alkyl, phenyl-$(C_1-C_4)$alkyl, or $R_a$ and $R_b$ together with the nitrogen to which they are attached form a 4-6 membered heterocycloalkyl, wherein said heterocycloalkyl is optionally substituted with one or more $(C_1-C_4)$alkyl; and pharmaceutically acceptable salts, hydrates or solvates thereof.

In another aspect the invention provides a compound of general formula (I), wherein $R_1$ and $R_4$ are independently selected from the group consisting of hydrogen and $(C_1-C_4)$alkyl;

$R_2$ and $R_3$ are independently selected from the group consisting of hydrogen and $(C_1-C_4)$alkyl;

n=0, 1 or 2; and when n is 0, $R_4$ does not exist;

Q is selected from the group consisting of —O—C(O)—$R_5$ and —O—C(O)—$(C_1-C_6)$alkyl-$R_5$;

$R_5$ is selected from the group consisting of a (5-6) membered heteroaryl, a (9-10) membered heteroaryl and a (4-6) membered heterocycloalkyl, wherein said heteroaryl and heterocycloalkyl are optionally substituted with one or more substituents independently selected from $R_6$;

$R_6$ consists of halogen, cyano, hydroxyl, $(C_1-C_4)$alkyl, halo$(C_1-C_4)$alkyl, $(C_1-C_4)$alkyloxy, —OR$_x$, —C(O)NR$_a$R$_b$, —C(O)OR$_a$, —C(O)R$_a$, and cycloalkyl;

$R_x$ is $(C_1-C_4)$alkyl;

$R_a$ and $R_b$ are independently selected from the group consisting of hydrogen and $(C_1-C_4)$alkyl, or pharmaceutically acceptable salts, hydrates or solvates thereof.

In another embodiment of the present invention, all of $R_1$, $R_2$, $R_3$ are hydrogen, n is 0, Q is selected from the group consisting of —O—C(O)—$R_5$ and —O—C(O)—$(C_1-C_6)$alkyl-$R_5$, wherein $R_5$ is selected from the group consisting of a (5-6) membered heteroaryl and a (4-6) membered heterocycloalkyl, wherein said heteroaryl and heterocycloalkyl are optionally substituted with one or more substituents independently selected from $(C_1-C_4)$alkyl, $(C_1-C_4)$alkyloxy, —C(O)R$_a$, and $(C_3-C_6)$cycloalkyl, wherein $R_a$ is $(C_1-C_4)$alkyl.

In another embodiment of the present invention, all of $R_1$, $R_2$, $R_3$ are hydrogen, n is 0, Q is —O—C(O)—$R_5$; wherein $R_5$ is a (5-6) membered heteroaryl optionally substituted with one or more of $(C_1-C_4)$alkyl.

In another embodiment of the present invention, all of $R_1$, $R_2$, $R_3$ are hydrogen, n is 0, Q is —O—C(O)—$R_5$; wherein $R_5$ is selected from the group consisting of isoxazolyl, oxazolyl, pyrazolyl, thiazolyl, isothiazolyl, all of which are optionally substituted with one or more of $(C_1-C_4)$alkyl.

In another embodiment of the present invention, all of $R_1$, $R_2$, $R_3$ are hydrogen, n is 0, Q is —O—C(O)—$R_5$; wherein $R_5$ is a (4-6) membered heterocycloalkyl optionally substituted with one or more of —C(O)R$_a$; wherein $R_a$ is $(C_1-C_4)$alkyl.

In another embodiment of the present invention, all of $R_1$, $R_2$, $R_3$ are hydrogen, n is 0, Q is —O—C(O)—$R_5$; wherein $R_5$ is selected from the group consisting of tetrahydropyranyl and piperidinyl, optionally substituted with —C(O)R$_a$; wherein $R_a$ is $(C_1-C_4)$alkyl.

In another embodiment of the present invention, all of $R_1$, $R_2$, $R_3$ are hydrogen, n is 0, Q is —O—C(O)—$(C_1-C_6)$alkyl-$R_5$, wherein $R_5$ is a (5-6) membered heteroaryl optionally substituted with one or more of $(C_1-C_4)$alkyl.

In another embodiment of the present invention, all of $R_1$, $R_2$, $R_3$ are hydrogen, n is 0, Q is —O—C(O)—$(C_1-C_6)$alkyl-$R_5$; wherein $R_5$ is selected from the group consisting of pyrrolyl, isoxazolyl and thiazolyl, all of which are optionally substituted with one or more of $(C_1-C_4)$alkyl.

In another embodiment of the present invention, all of $R_1$, $R_2$, $R_3$, $R_4$ are hydrogen, n is 1, Q is —O—C(O)—$R_5$; wherein $R_5$ is selected from the group consisting of a (5-6) membered heteroaryl, a (9-10) membered heteroaryl, and a (4-6) membered heterocycloalkyl, wherein said heteroaryl and heterocycloalkyl are optionally substituted with one or more substituents independently selected from $R_6$, wherein $R_6$ consists of hydroxyl, $(C_1-C_4)$alkyl, $(C_1-C_4)$alkyloxy, —OR$_x$, —C(O)NR$_a$R$_b$, —C(O)OR$_a$, —C(O)R$_a$, and $(C_3-C_6)$cycloalkyl, wherein $R_x$, $R_a$, $R_b$ are all $(C_1-C_4)$alkyl.

In another embodiment of the present invention, all of $R_1$, $R_2$, $R_3$, $R_4$ are hydrogen, n is 1, Q is —O—C(O)—$R_5$; wherein $R_5$ is a (5-6) membered or a (9-10) membered heteroaryl optionally substituted with one or more substituents independently selected from $R_6$, wherein $R_6$ consists of hydroxyl, $(C_1-C_4)$alkyl, $(C_1-C_4)$alkyloxy, —OR$_x$, —C(O)

$NR_aR_b$, —C(O)OR$_a$, —C(O)R$_a$, and (C$_3$-C$_6$)cycloalkyl, wherein R$_x$, R$_a$, R$_b$ are all (C$_1$-C$_4$)alkyl.

In another embodiment of the present invention, all of R$_1$, R$_2$, R$_3$, R$_4$ are hydrogen, n is 1, Q is —O—C(O)—R$_5$; wherein R$_5$ is selected from the group consisting of imidazolyl, pyrazolyl, isoxazolyl, oxazolyl, triazolyl, oxadiazolyl, pyridazinyl, pyrimidinyl, pyridinyl, isothiazolyl, thiazolyl, thiadiazolyl, benzimidazolyl, all of which are optionally substituted with one or more substituents independently selected from R$_6$; wherein R$_6$ consists of hydroxyl, (C$_1$-C$_4$) alkyl, (C$_1$-C$_4$)alkyloxy, (C$_3$-C$_6$)cycloalkyl and —OR$_x$, wherein R$_x$ is (C$_1$-C$_4$)alkyl.

In another embodiment of the present invention, all of R$_1$, R$_2$, R$_3$, R$_4$ are hydrogen, n is 1, Q is —C(O)—R$_5$; wherein R$_5$ is a (4-6) membered heterocycloalkyl, optionally substituted with one or more substituents independently selected from R$_6$; wherein R$_6$ consists of hydroxyl, (C$_1$-C$_4$)alkyl, (C$_1$-C$_4$)alkyloxy, —OR$_x$, —C(O)NR$_a$R$_b$, —C(O)OR$_a$, —C(O)R$_a$, and (C$_3$-C$_6$)cycloalkyl, R$_x$, R$_a$, R$_b$ are all (C$_1$-C$_4$)alkyl.

In another embodiment of the present invention, all of R$_1$, R$_2$, R$_3$, R$_4$ are hydrogen, n is 1, Q is —O—C(O)—R$_5$; wherein R$_5$ is selected from the group consisting of pyrrolidinyl, piperidinyl, tetrahydrofuranyl, tetrahydropyranyl, azetidinyl, tetrahydrothiopyranyl, dioxothiolanyl and dioxothianyl, all of which are optionally substituted with —C(O)NR$_a$R$_b$, —C(O)OR$_a$, and —C(O)R$_a$, wherein R$_a$, R$_b$ are (C$_1$-C$_4$)alkyl.

In another embodiment of the present invention, R$_1$ and R$_4$ are both hydrogen, one of R$_2$ and R$_3$ is hydrogen and the other one of R$_2$ and R$_3$ is (C$_1$-C$_4$)alkyl; n is 1, Q is —O—C(O)—R$_5$, wherein R$_5$ is a (4-6) membered heterocycloalkyl.

In another embodiment of the present invention, R$_1$ and R$_4$ are both hydrogen, one of R$_2$ and R$_3$ is hydrogen and the other one of R$_2$ and R$_3$ is (C$_1$-C$_4$)alkyl; n is 1, Q is —O—C(O)—R$_5$, wherein R is selected from the group consisting of tetrahydrofuranyl or tetrahydropyranyl.

In another embodiment of the present invention, R$_1$ and R$_4$ are both hydrogen, R$_2$ and R$_3$ are both (C$_1$-C$_4$)alkyl; n is 1, Q is —O—C(O)—R$_5$, wherein R is a (4-6) membered heterocycloalkyl.

In another embodiment of the present invention, R$_1$ and R$_4$ are both hydrogen, R$_2$ and R$_3$ are both (C$_1$-C$_4$)alkyl; n is 1, Q is —O—C(O)—R$_5$, wherein R is selected from the group consisting of tetrahydrofuranyl or tetrahydropyranyl.

In another embodiment of the present invention, all of R$_1$, R$_2$, R$_3$, R$_4$ are hydrogen, n is 2, Q is —O—C(O)—R$_5$, wherein R is selected from the group consisting of a (5-6) membered heteroaryl and a (4-6) membered heterocycloalkyl, wherein said heteroaryl is optionally substituted with one or more of (C$_1$-C$_4$)alkyl.

In another embodiment of the present invention, all of R$_1$, R$_2$, R$_3$, R$_4$ are hydrogen, n is 2, Q is —O—C(O)—R$_5$, wherein R$_5$ is a (5-6) membered heteroaryl optionally substituted with one or more of (C$_1$-C$_4$)alkyl.

In another embodiment of the present invention, all of R$_1$, R$_2$, R$_3$, R$_4$ are hydrogen, n is 2, Q is —O—C(O)—R$_5$; wherein R$_5$ is selected from the group consisting of oxazolyl, isothiazolyl and thiazolyl, all of which are optionally substituted with one or more of (C$_1$-C$_4$)alkyl.

In another embodiment of the present invention, all of R$_1$, R$_2$, R$_3$, R$_4$ are hydrogen, n is 2, Q is —C(O)—R$_5$; wherein R$_5$ is a (4-6) membered heterocycloalkyl.

In another embodiment of the present invention, all of R$_1$, R$_2$, R$_3$, R$_4$ are hydrogen, n is 2, Q is —O—C(O)—R$_5$; wherein R$_5$ is tetrahydropyranyl.

In another embodiment of the present invention, R$_1$ is hydrogen.

In another embodiment of the present invention, R$_1$ and R$_4$ are both hydrogen.

In another embodiment of the present invention, one of R$_2$ and R$_3$ is hydrogen and the other one of R$_2$ and R$_3$ is (C$_1$-C$_4$)alkyl.

In another embodiment of the present invention, R$_2$ and R$_3$ are both hydrogen.

In another embodiment of the present invention, R$_2$ and R$_3$ are both (C$_1$-C$_4$)alkyl, e.g. both methyl.

In another embodiment of the present invention, n is 0.
In another embodiment of the present invention, n is 1.
In another embodiment of the present invention, n is 2.
In another embodiment of the present invention, Q is —O—C(O)—R$_5$.

In another embodiment of the present invention, Q is -O—C(O)—(C$_1$-C$_6$)alkyl-R$_5$.

In another embodiment of the present invention, R$_5$ is heteroaryl optionally substituted with one or more substituents independently selected from R$_6$.

In another embodiment of the present invention, R$_5$ is a (5-6) membered heteroaryl optionally substituted with one or more substituents independently selected from R$_6$.

In another embodiment of the present invention, R$_5$ is a (9-10) membered heteroaryl optionally substituted with one or more substituents independently selected from R$_6$.

In another embodiment of the present invention, R$_5$ is heterocycloalkyl optionally substituted with one or more substituents independently selected from R$_6$.

In another embodiment of the present invention, R$_5$ is a (4-6) membered heterocycloalkyl optionally substituted with one or more substituents independently selected from R$_6$.

In another embodiment of the present invention, R$_6$ consists of hydroxyl, (C$_1$-C$_4$)alkyl, (C$_1$-C$_4$)alkyloxy, —OR$_x$, —C(O)NR$_a$R$_b$, —C(O)OR$_a$, —C(O)R$_a$, and cycloalkyl, wherein all of R$_x$, R$_a$, R$_b$ are (C$_1$-C$_4$)alkyl.

In another embodiment of the present invention, R$_6$ is hydroxyl.

In another embodiment of the present invention, R$_6$ is (C$_1$-C$_4$)alkyl, e.g. methyl or ethyl.

In another embodiment of the present invention, R$_6$ is (C$_1$-C$_4$)alkyloxy.

In another embodiment of the present invention, R$_6$ is —OR$_x$, wherein R$_x$ is (C$_1$-C$_4$)alkyl.

In another embodiment of the present invention, R$_6$ is —C(O)NR$_a$R$_b$, wherein R$_a$, R$_b$ are (C$_1$-C$_4$)alkyl.

In another embodiment of the present invention, R$_6$ is —C(O)OR$_a$, wherein R$_a$ is (C$_1$-C$_4$)alkyl.

In another embodiment of the present invention, R$_6$ is C(O)R$_a$, wherein R$_a$ is (C$_1$-C$_4$)-alkyl, e.g. C(O)CH$_3$.

In another embodiment of the present invention, R$_6$ is cycloalkyl, e.g. (C$_3$-C$_6$)cycloalkyl, e.g. cyclopropyl.

Specific examples of compounds of formula (I) may be selected from the group consisting of:

2-(3-ethyl-4-oxo-spiro[6,8-dihydro-5H-pyrazolo[4,3-c] azepine-7,4'-tetrahydropyran]-1-yl)ethyl isoxazole-5-carboxylate;

2-(3-ethyl-4-oxo-spiro[6,8-dihydro-5H-pyrazolo[4,3-c] azepine-7,4'-tetrahydropyran]-1-yl)ethyl oxazole-4-carboxylate;

2-(3-ethyl-4-oxo-spiro[6,8-dihydro-5H-pyrazolo[4,3-c] azepine-7,4'-tetrahydropyran]-1-yl)ethyl 1-methylpyrazole-4-carboxylate;

2-(3-ethyl-4-oxo-spiro[6,8-dihydro-5H-pyrazolo[4,3-c]
  azepine-7,4'-tetrahydropyran]-1-yl)ethyl 5-methylisoxazole-3-carboxylate;
2-(3-ethyl-4-oxo-spiro[6,8-dihydro-5H-pyrazolo[4,3-c]
  azepine-7,4'-tetrahydropyran]-1-yl)ethyl 2-methyloxazole-4-carboxylate;
2-(3-ethyl-4-oxo-spiro[6,8-dihydro-5H-pyrazolo[4,3-c]
  azepine-7,4'-tetrahydropyran]-1-yl)ethyl 2-methyloxazole-5-carboxylate;
2-(3-ethyl-4-oxo-spiro[6,8-dihydro-5H-pyrazolo[4,3-c]
  azepine-7,4'-tetrahydropyran]-1-yl)ethyl thiazole-4-carboxylate;
2-(3-ethyl-4-oxo-spiro[6,8-dihydro-5H-pyrazolo[4,3-c]
  azepine-7,4'-tetrahydropyran]-1-yl)ethyl tetrahydropyran-4-carboxylate;
2-(3-ethyl-4-oxo-spiro[6,8-dihydro-5H-pyrazolo[4,3-c]
  azepine-7,4'-tetrahydropyran]-1-yl)ethyl 2-(1-methylpyrrol-2-yl)acetate;
2-(3-ethyl-4-oxo-spiro[6,8-dihydro-5H-pyrazolo[4,3-c]
  azepine-7,4'-tetrahydropyran]-1-yl)ethyl 1,5-dimethylpyrazole-3-carboxylate;
2-(3-ethyl-4-oxo-spiro[6,8-dihydro-5H-pyrazolo[4,3-c]
  azepine-7,4'-tetrahydropyran]-1-yl)ethyl 2-(5-methylisoxazol-3-yl)acetate;
2-(3-ethyl-4-oxo-spiro[6,8-dihydro-5H-pyrazolo[4,3-c]
  azepine-7,4'-tetrahydropyran]-1-yl)ethyl 2-(3-methylisoxazol-5-yl)acetate;
2-(3-ethyl-4-oxo-spiro[6,8-dihydro-5H-pyrazolo[4,3-c]
  azepine-7,4'-tetrahydropyran]-1-yl)ethyl 3-methylisothiazole-5-carboxylate;
2-(3-ethyl-4-oxo-spiro[6,8-dihydro-5H-pyrazolo[4,3-c]
  azepine-7,4'-tetrahydropyran]-1-yl)ethyl 4-methylthiazole-2-carboxylate;
2-(3-ethyl-4-oxo-spiro[6,8-dihydro-5H-pyrazolo[4,3-c]
  azepine-7,4'-tetrahydropyran]-1-yl)ethyl 2-(2-methylthiazol-4-yl)acetate;
2-(3-ethyl-4-oxo-spiro[6,8-dihydro-5H-pyrazolo[4,3-c]
  azepine-7,4'-tetrahydropyran]-1-yl)ethyl 1-acetylpiperidine-4-carboxylate;
3-(3-ethyl-4-oxo-spiro[6,8-dihydro-5H-pyrazolo[4,3-c]
  azepine-7,4'-tetrahydropyran]-1-yl)propyl 1H-imidazole-4-carboxylate;
3-(3-ethyl-4-oxo-spiro[6,8-dihydro-5H-pyrazolo[4,3-c]
  azepine-7,4'-tetrahydropyran]-1-yl)propyl 1H-pyrazole-3-carboxylate;
3-(3-ethyl-4-oxo-spiro[6,8-dihydro-5H-pyrazolo[4,3-c]
  azepine-7,4'-tetrahydropyran]-1-yl)propyl 1H-imidazole-2-carboxylate;
3-(3-ethyl-4-oxo-spiro[6,8-dihydro-5H-pyrazolo[4,3-c]
  azepine-7,4'-tetrahydropyran]-1-yl)propyl 1H-pyrazole-4-carboxylate;
3-(3-ethyl-4-oxo-spiro[6,8-dihydro-5H-pyrazolo[4,3-c]
  azepine-7,4'-tetrahydropyran]-1-yl)propyl isoxazole-3-carboxylate;
3-(3-ethyl-4-oxo-spiro[6,8-dihydro-5H-pyrazolo[4,3-c]
  azepine-7,4'-tetrahydropyran]-1-yl)propyl isoxazole-5-carboxylate;
3-(3-ethyl-4-oxo-spiro[6,8-dihydro-5H-pyrazolo[4,3-c]
  azepine-7,4'-tetrahydropyran]-1-yl)propyl oxazole-4-carboxylate;
3-(3-ethyl-4-oxo-spiro[6,8-dihydro-5H-pyrazolo[4,3-c]
  azepine-7,4'-tetrahydropyran]-1-yl)propyl oxazole-5-carboxylate;
3-(3-ethyl-4-oxo-spiro[6,8-dihydro-5H-pyrazolo[4,3-c]
  azepine-7,4'-tetrahydropyran]-1-yl)propyl 1H-triazole-4-carboxylate;
3-(3-ethyl-4-oxo-spiro[6,8-dihydro-5H-pyrazolo[4,3-c]
  azepine-7,4'-tetrahydropyran]-1-yl)propyl 1H-1,2,4-triazole-3-carboxylate;
3-(3-ethyl-4-oxo-spiro[6,8-dihydro-5H-pyrazolo[4,3-c]
  azepine-7,4'-tetrahydropyran]-1-yl)propyl 1,2,5-oxadiazole-3-carboxylate;
3-(3-ethyl-4-oxo-spiro[6,8-dihydro-5H-pyrazolo[4,3-c]
  azepine-7,4'-tetrahydropyran]-1-yl)propyl tetrahydrofuran-3-carboxylate;
3-(3-ethyl-4-oxo-spiro[6,8-dihydro-5H-pyrazolo[4,3-c]
  azepine-7,4'-tetrahydropyran]-1-yl)propyl pyridazine-3-carboxylate;
3-(3-ethyl-4-oxo-spiro[6,8-dihydro-5H-pyrazolo[4,3-c]
  azepine-7,4'-tetrahydropyran]-1-yl)propyl pyridazine-4-carboxylate;
3-(3-ethyl-4-oxo-spiro[6,8-dihydro-5H-pyrazolo[4,3-c]
  azepine-7,4'-tetrahydropyran]-1-yl)propyl pyrimidine-2-carboxylate;
3-(3-ethyl-4-oxo-spiro[6,8-dihydro-5H-pyrazolo[4,3-c]
  azepine-7,4'-tetrahydropyran]-1-yl)propyl 1-methylpyrazole-3-carboxylate;
3-(3-ethyl-4-oxo-spiro[6,8-dihydro-5H-pyrazolo[4,3-c]
  azepine-7,4'-tetrahydropyran]-1-yl)propyl 5-methyl-1H-pyrazole-3-carboxylate;
3-(3-ethyl-4-oxo-spiro[6,8-dihydro-5H-pyrazolo[4,3-c]
  azepine-7,4'-tetrahydropyran]-1-yl)propyl 3-methyl-1H-pyrazole-5-carboxylate;
3-(3-ethyl-4-oxo-spiro[6,8-dihydro-5H-pyrazolo[4,3-c]
  azepine-7,4'-tetrahydropyran]-1-yl)propyl 2-methylpyrazole-3-carboxylate;
3-(3-ethyl-4-oxo-spiro[6,8-dihydro-5H-pyrazolo[4,3-c]
  azepine-7,4'-tetrahydropyran]-1-yl)propyl 2-methyl-1H-imidazole-4-carboxylate;
3-(3-ethyl-4-oxo-spiro[6,8-dihydro-5H-pyrazolo[4,3-c]
  azepine-7,4'-tetrahydropyran]-1-yl)propyl 2-methyl-1H-imidazole-5-carboxylate;
3-(3-ethyl-4-oxo-spiro[6,8-dihydro-5H-pyrazolo[4,3-c]
  azepine-7,4'-tetrahydropyran]-1-yl)propyl 1-methylpyrazole-4-carboxylate;
3-(3-ethyl-4-oxo-spiro[6,8-dihydro-5H-pyrazolo[4,3-c]
  azepine-7,4'-tetrahydropyran]-1-yl)propyl 1-methylimidazole-4-carboxylate;
3-(3-ethyl-4-oxo-spiro[6,8-dihydro-5H-pyrazolo[4,3-c]
  azepine-7,4'-tetrahydropyran]-1-yl)propyl 1-methylimidazole-2-carboxylate;
3-(3-ethyl-4-oxo-spiro[6,8-dihydro-5H-pyrazolo[4,3-c]
  azepine-7,4'-tetrahydropyran]-1-yl)propyl 3-methylimidazole-4-carboxylate;
3-(3-ethyl-4-oxo-spiro[6,8-dihydro-5H-pyrazolo[4,3-c]
  azepine-7,4'-tetrahydropyran]-1-yl)propyl 4-methylisoxazole-5-carboxylate;
3-(3-ethyl-4-oxo-spiro[6,8-dihydro-5H-pyrazolo[4,3-c]
  azepine-7,4'-tetrahydropyran]-1-yl)propyl 3-methylisoxazole-5-carboxylate;
3-(3-ethyl-4-oxo-spiro[6,8-dihydro-5H-pyrazolo[4,3-c]
  azepine-7,4'-tetrahydropyran]-1-yl)propyl 5-methylisoxazole-3-carboxylate;
3-(3-ethyl-4-oxo-spiro[6,8-dihydro-5H-pyrazolo[4,3-c]
  azepine-7,4'-tetrahydropyran]-1-yl)propyl 3-methylisoxazole-4-carboxylate;
3-(3-ethyl-4-oxo-spiro[6,8-dihydro-5H-pyrazolo[4,3-c]
  azepine-7,4'-tetrahydropyran]-1-yl)propyl 2-methyloxazole-4-carboxylate;
3-(3-ethyl-4-oxo-spiro[6,8-dihydro-5H-pyrazolo[4,3-c]
  azepine-7,4'-tetrahydropyran]-1-yl)propyl 4-methyloxazole-5-carboxylate;

3-(3-ethyl-4-oxo-spiro[6,8-dihydro-5H-pyrazolo[4,3-c]azepine-7,4'-tetrahydropyran]-1-yl)propyl 2-methyloxazole-5-carboxylate;

3-(3-ethyl-4-oxo-spiro[6,8-dihydro-5H-pyrazolo[4,3-c]azepine-7,4'-tetrahydropyran]-1-yl)propyl 3-methyltriazole-4-carboxylate;

3-(3-ethyl-4-oxo-spiro[6,8-dihydro-5H-pyrazolo[4,3-c]azepine-7,4'-tetrahydropyran]-1-yl)propyl 5-methyl-4H-1,2,4-triazole-3-carboxylate;

3-(3-ethyl-4-oxo-spiro[6,8-dihydro-5H-pyrazolo[4,3-c]azepine-7,4'-tetrahydropyran]-1-yl)propyl 4-methyl-1,2,5-oxadiazole-3-carboxylate;

3-(3-ethyl-4-oxo-spiro[6,8-dihydro-5H-pyrazolo[4,3-c]azepine-7,4'-tetrahydropyran]-1-yl)propyl 3-hydroxyisoxazole-5-carboxylate;

3-(3-ethyl-4-oxo-spiro[6,8-dihydro-5H-pyrazolo[4,3-c]azepine-7,4'-tetrahydropyran]-1-yl)propyl isothiazole-3-carboxylate;

3-(3-ethyl-4-oxo-spiro[6,8-dihydro-5H-pyrazolo[4,3-c]azepine-7,4'-tetrahydropyran]-1-yl)propyl isothiazole-5-carboxylate;

3-(3-ethyl-4-oxo-spiro[6,8-dihydro-5H-pyrazolo[4,3-c]azepine-7,4'-tetrahydropyran]-1-yl)propyl isothiazole-4-carboxylate;

3-(3-ethyl-4-oxo-spiro[6,8-dihydro-5H-pyrazolo[4,3-c]azepine-7,4'-tetrahydropyran]-1-yl)propyl thiazole-5-carboxylate;

3-(3-ethyl-4-oxo-spiro[6,8-dihydro-5H-pyrazolo[4,3-c]azepine-7,4'-tetrahydropyran]-1-yl)propyl thiadiazole-4-carboxylate;

3-(3-ethyl-4-oxo-spiro[6,8-dihydro-5H-pyrazolo[4,3-c]azepine-7,4'-tetrahydropyran]-1-yl)propyl tetrahydropyran-3-carboxylate;

3-(3-ethyl-4-oxo-spiro[6,8-dihydro-5H-pyrazolo[4,3-c]azepine-7,4'-tetrahydropyran]-1-yl)propyl tetrahydropyran-4-carboxylate;

3-(3-ethyl-4-oxo-spiro[6,8-dihydro-5H-pyrazolo[4,3-c]azepine-7,4'-tetrahydropyran]-1-yl)propyl tetrahydrothiophene-3-carboxylate;

3-(3-ethyl-4-oxo-spiro[6,8-dihydro-5H-pyrazolo[4,3-c]azepine-7,4'-tetrahydropyran]-1-yl)propyl 5-methylpyridine-2-carboxylate;

3-(3-ethyl-4-oxo-spiro[6,8-dihydro-5H-pyrazolo[4,3-c]azepine-7,4'-tetrahydropyran]-1-yl)propyl 3-methylpyridine-2-carboxylate;

3-(3-ethyl-4-oxo-spiro[6,8-dihydro-5H-pyrazolo[4,3-c]azepine-7,4'-tetrahydropyran]-1-yl)propyl 4-methylpyridine-2-carboxylate;

3-(3-ethyl-4-oxo-spiro[6,8-dihydro-5H-pyrazolo[4,3-c]azepine-7,4'-tetrahydropyran]-1-yl)propyl 6-methylpyridine-2-carboxylate;

3-(3-ethyl-4-oxo-spiro[6,8-dihydro-5H-pyrazolo[4,3-c]azepine-7,4'-tetrahydropyran]-1-yl)propyl 2-methylpyridine-3-carboxylate;

3-(3-ethyl-4-oxo-spiro[6,8-dihydro-5H-pyrazolo[4,3-c]azepine-7,4'-tetrahydropyran]-1-yl)propyl 5-methylpyrimidine-2-carboxylate;

3-(3-ethyl-4-oxo-spiro[6,8-dihydro-5H-pyrazolo[4,3-c]azepine-7,4'-tetrahydropyran]-1-yl)propyl 3-methylpyridazine-4-carboxylate;

3-(3-ethyl-4-oxo-spiro[6,8-dihydro-5H-pyrazolo[4,3-c]azepine-7,4'-tetrahydropyran]-1-yl)propyl 2-methylpyrimidine-4-carboxylate;

3-(3-ethyl-4-oxo-spiro[6,8-dihydro-5H-pyrazolo[4,3-c]azepine-7,4'-tetrahydropyran]-1-yl)propyl 4-methylpyrimidine-2-carboxylate;

3-(3-ethyl-4-oxo-spiro[6,8-dihydro-5H-pyrazolo[4,3-c]azepine-7,4'-tetrahydropyran]-1-yl)propyl 2-methylpyrimidine-5-carboxylate;

3-(3-ethyl-4-oxo-spiro[6,8-dihydro-5H-pyrazolo[4,3-c]azepine-7,4'-tetrahydropyran]-1-yl)propyl 2,5-dimethylpyrazole-3-carboxylate;

3-(3-ethyl-4-oxo-spiro[6,8-dihydro-5H-pyrazolo[4,3-c]azepine-7,4'-tetrahydropyran]-1-yl)propyl 1,5-dimethylpyrazole-3-carboxylate;

3-(3-ethyl-4-oxo-spiro[6,8-dihydro-5H-pyrazolo[4,3-c]azepine-7,4'-tetrahydropyran]-1-yl)propyl 2,3-dimethylimidazole-4-carboxylate;

3-(3-ethyl-4-oxo-spiro[6,8-dihydro-5H-pyrazolo[4,3-c]azepine-7,4'-tetrahydropyran]-1-yl)propyl 4,5-dimethylisoxazole-3-carboxylate;

3-(3-ethyl-4-oxo-spiro[6,8-dihydro-5H-pyrazolo[4,3-c]azepine-7,4'-tetrahydropyran]-1-yl)propyl 3,5-dimethylisoxazole-4-carboxylate;

3-(3-ethyl-4-oxo-spiro[6,8-dihydro-5H-pyrazolo[4,3-c]azepine-7,4'-tetrahydropyran]-1-yl)propyl 2,5-dimethyloxazole-4-carboxylate;

3-(3-ethyl-4-oxo-spiro[6,8-dihydro-5H-pyrazolo[4,3-c]azepine-7,4'-tetrahydropyran]-1-yl)propyl 1-acetylazetidine-3-carboxylate;

3-(3-ethyl-4-oxo-spiro[6,8-dihydro-5H-pyrazolo[4,3-c]azepine-7,4'-tetrahydropyran]-1-yl)propyl 3-methylisothiazole-5-carboxylate;

3-(3-ethyl-4-oxo-spiro[6,8-dihydro-5H-pyrazolo[4,3-c]azepine-7,4'-tetrahydropyran]-1-yl)propyl 5-methylisothiazole-4-carboxylate;

3-(3-ethyl-4-oxo-spiro[6,8-dihydro-5H-pyrazolo[4,3-c]azepine-7,4'-tetrahydropyran]-1-yl)propyl 5-methylthiazole-4-carboxylate;

3-(3-ethyl-4-oxo-spiro[6,8-dihydro-5H-pyrazolo[4,3-c]azepine-7,4'-tetrahydropyran]-1-yl)propyl 4-methylthiazole-5-carboxylate;

3-(3-ethyl-4-oxo-spiro[6,8-dihydro-5H-pyrazolo[4,3-c]azepine-7,4'-tetrahydropyran]-1-yl)propyl 2-methylthiazole-5-carboxylate;

3-(3-ethyl-4-oxo-spiro[6,8-dihydro-5H-pyrazolo[4,3-c]azepine-7,4'-tetrahydropyran]-1-yl)propyl 4-methylthiadiazole-5-carboxylate;

3-(3-ethyl-4-oxo-spiro[6,8-dihydro-5H-pyrazolo[4,3-c]azepine-7,4'-tetrahydropyran]-1-yl)propyl tetrahydrothiopyran-3-carboxylate;

3-(3-ethyl-4-oxo-spiro[6,8-dihydro-5H-pyrazolo[4,3-c]azepine-7,4'-tetrahydropyran]-1-yl)propyl tetrahydrothiopyran-4-carboxylate;

3-(3-ethyl-4-oxo-spiro[6,8-dihydro-5H-pyrazolo[4,3-c]azepine-7,4'-tetrahydropyran]-1-yl)propyl 2,6-dimethylpyridine-4-carboxylate;

3-(3-ethyl-4-oxo-spiro[6,8-dihydro-5H-pyrazolo[4,3-c]azepine-7,4'-tetrahydropyran]-1-yl)propyl 2,6-dimethylpyridine-3-carboxylate;

3-(3-ethyl-4-oxo-spiro[6,8-dihydro-5H-pyrazolo[4,3-c]azepine-7,4'-tetrahydropyran]-1-yl)propyl 3,6-dimethylpyridazine-4-carboxylate;

3-(3-ethyl-4-oxo-spiro[6,8-dihydro-5H-pyrazolo[4,3-c]azepine-7,4'-tetrahydropyran]-1-yl)propyl 2-cyclopropyloxazole-4-carboxylate;

3-(3-ethyl-4-oxo-spiro[6,8-dihydro-5H-pyrazolo[4,3-c]azepine-7,4'-tetrahydropyran]-1-yl)propyl 2-ethyl-5-methyl-pyrazole-3-carboxylate;

3-(3-ethyl-4-oxo-spiro[6,8-dihydro-5H-pyrazolo[4,3-c]azepine-7,4'-tetrahydropyran]-1-yl)propyl 1,3,5-trimethylpyrazole-4-carboxylate;

3-(3-ethyl-4-oxo-spiro[6,8-dihydro-5H-pyrazolo[4,3-c]azepine-7,4'-tetrahydropyran]-1-yl)propyl 3-ethyl-5-methyl-isoxazole-4-carboxylate;

3-(3-ethyl-4-oxo-spiro[6,8-dihydro-5H-pyrazolo[4,3-c]azepine-7,4'-tetrahydropyran]-1-yl)propyl 1-acetylpyrrolidine-3-carboxylate;

3-(3-ethyl-4-oxo-spiro[6,8-dihydro-5H-pyrazolo[4,3-c]azepine-7,4'-tetrahydropyran]-1-yl)propyl 4,5-dimethyl-thiazole-2-carboxylate;

3-(3-ethyl-4-oxo-spiro[6,8-dihydro-5H-pyrazolo[4,3-c]azepine-7,4'-tetrahydropyran]-1-yl)propyl 2,4-dimethyl-thiazole-5-carboxylate;

3-(3-ethyl-4-oxo-spiro[6,8-dihydro-5H-pyrazolo[4,3-c]azepine-7,4'-tetrahydropyran]-1-yl)propyl 1,1-dioxothiolane-3-carboxylate;

3-(3-ethyl-4-oxo-spiro[6,8-dihydro-5H-pyrazolo[4,3-c]azepine-7,4'-tetrahydropyran]-1-yl)propyl 3,5-diethyl-isoxazole-4-carboxylate;

3-(3-ethyl-4-oxo-spiro[6,8-dihydro-5H-pyrazolo[4,3-c]azepine-7,4'-tetrahydropyran]-1-yl)propyl 1-acetylpiperidine-3-carboxylate;

3-(3-ethyl-4-oxo-spiro[6,8-dihydro-5H-pyrazolo[4,3-c]azepine-7,4'-tetrahydropyran]-1-yl)propyl 1-acetylpiperidine-4-carboxylate;

3-(3-ethyl-4-oxo-spiro[6,8-dihydro-5H-pyrazolo[4,3-c]azepine-7,4'-tetrahydropyran]-1-yl)propyl 2-methoxy-4-methyl-thiazole-5-carboxylate;

3-(3-ethyl-4-oxo-spiro[6,8-dihydro-5H-pyrazolo[4,3-c]azepine-7,4'-tetrahydropyran]-1-yl)propyl 3-methylbenzimidazole-5-carboxylate;

3-(3-ethyl-4-oxo-spiro[6,8-dihydro-5H-pyrazolo[4,3-c]azepine-7,4'-tetrahydropyran]-1-yl)propyl 1,1-dioxothiane-3-carboxylate;

3-(3-ethyl-4-oxo-spiro[6,8-dihydro-5H-pyrazolo[4,3-c]azepine-7,4'-tetrahydropyran]-1-yl)propyl 1,1-dioxothiane-4-carboxylate;

O3-[3-(3-ethyl-4-oxo-spiro[6,8-dihydro-5H-pyrazolo[4,3-c]azepine-7,4'-tetrahydropyran]-1-yl)propyl] O1-methyl piperidine-1,3-dicarboxylate;

O4-[3-(3-ethyl-4-oxo-spiro[6,8-dihydro-5H-pyrazolo[4,3-c]azepine-7,4'-tetrahydropyran]-1-yl)propyl] O1-methyl piperidine-1,4-dicarboxylate;

3-(3-ethyl-4-oxo-spiro[6,8-dihydro-5H-pyrazolo[4,3-c]azepine-7,4'-tetrahydropyran]-1-yl)propyl 1-(dimethylcarbamoyl)piperidine-3-carboxylate;

3-(3-ethyl-4-oxo-spiro[6,8-dihydro-5H-pyrazolo[4,3-c]azepine-7,4'-tetrahydropyran]-1-yl)propyl 1-(dimethylcarbamoyl)piperidine-4-carboxylate;

[(2R)-3-(3-ethyl-4-oxo-spiro[6,8-dihydro-5H-pyrazolo[4,3-c]azepine-7,4'-tetrahydropyran]-1-yl)-2-methyl-propyl] tetrahydrofuran-3-carboxylate;

[(2R)-3-(3-ethyl-4-oxo-spiro[6,8-dihydro-5H-pyrazolo[4,3-c]azepine-7,4'-tetrahydropyran]-1-yl)-2-methyl-propyl] tetrahydropyran-4-carboxylate;

[3-(3-ethyl-4-oxo-spiro[6,8-dihydro-5H-pyrazolo[4,3-c]azepine-7,4'-tetrahydropyran]-1-yl)-2,2-dimethyl-propyl] tetrahydrofuran-3-carboxylate;

[3-(3-ethyl-4-oxo-spiro[6,8-dihydro-5H-pyrazolo[4,3-c]azepine-7,4'-tetrahydropyran]-1-yl)-2,2-dimethyl-propyl] tetrahydropyran-4-carboxylate;

4-(3-ethyl-4-oxo-spiro[6,8-dihydro-5H-pyrazolo[4,3-c]azepine-7,4'-tetrahydropyran]-1-yl)butyl 2-methyloxazole-5-carboxylate;

4-(3-ethyl-4-oxo-spiro[6,8-dihydro-5H-pyrazolo[4,3-c]azepine-7,4'-tetrahydropyran]-1-yl)butyl isothiazole-4-carboxylate;

4-(3-ethyl-4-oxo-spiro[6,8-dihydro-5H-pyrazolo[4,3-c]azepine-7,4'-tetrahydropyran]-1-yl)butyl thiazole-4-carboxylate;

4-(3-ethyl-4-oxo-spiro[6,8-dihydro-5H-pyrazolo[4,3-c]azepine-7,4'-tetrahydropyran]-1-yl)butyl tetrahydropyran-4-carboxylate; or a pharmaceutically acceptable salt, hydrate or solvate thereof.

Definitions

As used throughout the present specification and appended claims, the following terms have the indicated meaning:

The term "alkyl" is intended to indicate a radical obtained when one hydrogen atom is removed from a branched or linear hydrocarbon. Said alkyl comprises 1-6, such as 1-4, such as 1-3, such as 2-3 or such as 1-2 carbon atoms. The term includes the subclasses normal alkyl (n-alkyl), secondary and tertiary alkyl, such as methyl, ethyl, n-propyl, isopropyl, n-butyl, isobutyl, sec.-butyl, tert.-butyl, n-pentyl, isopentyl, neopentyl, n-hexyl and isohexyl.

The terms "alkyloxy" and "alkoxy" are intended to indicate a radical of the formula —OR', wherein R' is alkyl as indicated herein, wherein the alkyl group is appended to the parent molecular moiety through an oxygen atom, e.g. methoxy (—OCH$_3$), ethoxy (—OCH$_2$CH$_3$), n-propoxy, isopropoxy, butoxy, tert-butoxy, and the like.

The term alkoxyalkyl is intended to indicate an alkyl group as defined above substituted with one or more alkoxy groups as defined above, e.g. methoxymethyl, ethoxymethyl, 2-methoxyethyl, 2-ethoxyethyl, 3-methoxyprop-1-yl, and the like The term "haloalkyl" is intended to indicate an alkyl group as defined herein substituted with one or more halogen atoms as defined herein, e.g. fluoro or chloro, such as fluoromethyl, difluoromethyl or trifluoromethyl.

The terms "haloalkyloxy" and "haloalkoxy" are intended to indicate a haloalkyl group as defined herein which is appended to the parent molecular moiety through an oxygen atom, such as difluoromethoxy or trifluoromethoxy.

The term "halogen" is intended to indicate a substituent from the 7$^{th}$ main group of the periodic table, such as fluoro, chloro and bromo.

The term "alkylthio" is intended to indicate a radical of the formula —S—R', wherein R' is alkyl as indicated herein, wherein the alkyl group is appended to the parent molecular moiety through a sulphur atom, e.g. —S—CH$_3$ (methylthio) or —S—CH$_2$CH$_3$ (ethylthio).

The term "cyano" is intended to indicate a —CN group attached to the parent molecular moiety through the carbon atom.

The term "cycloalkyl" is intended to indicate a saturated cycloalkane hydrocarbon radical, comprising 3-7 carbon atoms, 3-6 carbon atoms, 3-5 carbon atoms, 3-4 carbon atoms, e.g. cyclopropyl, cyclobutyl, cyclopentyl and cyclohexyl.

The term "aryl" is intended to indicate a radical of aromatic carbocyclic rings comprising 6-13 carbon atoms, 6-9 carbon atoms, such as 6 carbon atoms, in particular 5- or 6-membered rings, including fused carbocyclic rings with at least one aromatic ring. If the aryl group is a fused carbocyclic ring, the point of attachment of the aryl group to the parent molecular moiety may be through an aromatic or through an alifatic carbon atom within the aryl group. Representative examples of aryl include, but are not limited to phenyl, naphthyl, indenyl, indanyl, dihydronaphtyl, tetrahydronaphtyl and fluorenyl.

The term "heteroaryl" is intended to indicate radicals of monocyclic heteroaromatic rings comprising 5- or 6-membered ring which contains from 1-5 carbon atoms and from 1-4 heteroatoms selected from oxygen, sulphur and nitrogen. The heteroaryl radical may be connected to the parent molecular moiety through a carbon atom or a nitrogen atom contained anywhere within the heteroaryl group. Representative examples of heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, tetrazolyl, thiadiazolyl, thiazolyl, thienyl, triazolyl.

The term "heteroaryl" is also intended to include bicyclic heterocyclic aromatic rings containing one or more heteroatoms selected from nitrogen, oxygen and sulfur. Representative examples are indolyl, isoindolyl, benzofuranyl, indazolyl, benzopyranyl, benzimidazolyl.

The term "(5-6) membered heteroaryl" is intended to indicate radicals of monocyclic heteroaromatic rings comprising 5- or 6-membered ring which contains from 1-5 carbon atoms e.g. 2-5 or 2-4 carbon atoms, and from 1-4 heteroatoms, preferably 1 to 3 heteroatoms, e.g. 1-2 heteroatoms selected from oxygen, sulphur and nitrogen. The heteroaryl radical may be connected to the parent molecular moiety through a carbon atom or a nitrogen atom contained anywhere within the heteroaryl group. Representative examples of heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, tetrazolyl, thiadiazolyl, thiazolyl, thienyl, triazolyl.

The term "(9-10) membered heteroaryl" is intended to indicate radicals of bicyclic heteroaromatic rings comprising 9- or 10-membered ring which contains from 1-9 carbon atoms e.g. 4-7 or 4-6 carbon atoms, and from 1-6 heteroatoms, preferably 1 to 3 heteroatoms, e.g. 1-2 heteroatoms selected from oxygen, sulphur and nitrogen. Representative examples are indolyl, isoindolyl, benzofuranyl, indazolyl, benzopyranyl, benzimidazolyl, benzothiazolyl, benzisothiazolyl, benzoxazolyl, benzotriazolyl.

The term "heterocycloalkyl" is intended to indicate a cycloalkane radical as described herein, wherein one or more carbon atoms are replaced by heteroatoms, comprising 1-6 carbon atoms, e.g. 2-5 or 2-4 carbon atoms, further comprising 1-3 heteroatoms, preferably 1 to 2 heteroatoms, selected from O, N, or S, S($=$O) or S($=$O)$_2$. The heterocycloalkyl radical may be connected to the parent molecular moiety through a carbon atom or a nitrogen atom contained anywhere within the heterocycloalkyl group. Representative examples of heterocycloalkyl groups include, but are not limited to azepanyl, azetidinyl, aziridinyl, dioxanyl, dioxolanyl, dioxolyl, imidazolidinyl, morpholinyl, thiomorpholinyl, thiomorpholinyl-1-oxide, thiomorpholinyl-1,1-dioxide, oxetanyl, piperazinyl, piperidinyl, pyrrolidinyl, tetrahydrofuranyl, tetrahydrothiophene, tetrahydropyranyl, tetrahydrothiophenyl, tetrahydrothiopyranyl.

The term "(4-6) membered heterocycloalkyl" is intended to indicate a heterocyloalkyl as defined herein, comprising 4-6 ring-atoms, and comprising 1-5 carbon atoms, e.g. 2-5 or 2-4 carbon atoms, further comprising 1-3 heteroatoms, preferably 1 to 2 heteroatoms, selected from O, N, S, S($=$O) or S($=$O)$_2$. Representative examples of (4-6) membered heterocycloalkyl groups include azetidinyl, dioxanyl, dioxolanyl, imidazole-dinyl, morpholinyl, thiomorpholinyl, thiomorpholinyl-1-oxide, thiomorpholinyl-1,1-dioxide, oxetanyl, piperazinyl, piperidinyl, pyrrolidinyl, tetrahydrofuranyl, tetrahydropyranyl, tetrahydrothiophene, tetrahydrothiopyranyl, tetrahydrothiophenyl, thietanyl.

The term "hydrocarbon radical" is intended to indicate a radical containing only hydrogen and carbon atoms, it may contain one or more double and/or triple carbon-carbon bonds, and it may comprise cyclic moieties in combination with branched or linear moieties. Said hydrocarbon comprises 1-6 carbon atoms, and preferably comprises 1-5, e.g. 1-4, e.g. 1-3, e.g. 1-2 carbon atoms. The term includes alkyl, cycloalkyl and aryl, as indicated herein.

In some instances, the number of carbon atoms in a hydrocarbon radical (e.g. alkyl, cycloalkyl and aryl) is indicated by the prefix "($C_a$-$C_b$)", wherein a is the minimum number and b is the maximum number of carbons in the hydrocarbon radical. Thus, for example ($C_1$-$C_4$)alkyl is intended to indicate an alkyl radical comprising from 1 to 4 carbon atoms, and ($C_3$-$C_6$)cycloalkyl is intended to indicate a cycloalkyl radical comprising from 3 to 5 carbon ring atoms.

The term "hydroxyalkyl" is intended to indicate an alkyl group as defined above substituted with one or more hydroxy, e.g. hydroxymethyl, hydroxyethyl, hydroxypropyl.

The term "hydroxyl" is intended to indicate an —OH group.

The term "oxo" is intended to indicate an oxygen atom which is connected to the parent molecular moiety via a double bond ($=$O).

The term "thioxo" is intended to indicate a sulfur atom which is connected to the parent molecular moiety via a double bond ($=$S).

The group C(O) is intended to represent a carbonyl group (C$=$O).

The term "pharmaceutically acceptable salt" is intended to indicate salts prepared by reacting a compound of formula I, which comprise a basic moiety, with a suitable inorganic or organic acid, such as hydrochloric, hydrobromic, hydroiodic, sulfuric, nitric, phosphoric, formic, acetic, 2,2-dichloroaetic, adipic, ascorbic, L-aspartic, L-glutamic, galactaric, lactic, maleic, L-malic, phthalic, citric, propionic, benzoic, glutaric, gluconic, D-glucuronic, methanesulfonic, salicylic, succinic, malonic, tartaric, benzenesulfonic, ethane-1,2-disulfonic, 2-hydroxy ethanesulfonic acid, toluenesulfonic, sulfamic or fumaric acid. Further examples of pharmaceutical acceptable salts are listed in Berge, S. M.; J. Pharm. Sci.; (1977), 66(1), 1-19, which is incorporated herein by reference.

The term "solvate" is intended to indicate a species formed by interaction between a compound, e.g. a compound of formula I, and a solvent, e.g. alcohol, glycerol or water, wherein said species are in a crystalline form. When water is the solvent, said species is referred to as a hydrate.

The term "treatment" as used herein means the management and care of a patient for the purpose of combating a disease, disorder or condition. The term is intended to include the delaying of the progression of the disease, disorder or condition, the amelioration, alleviation or relief of symptoms and complications, and/or the cure or elimination of the disease, disorder or condition. The term may also include prevention of the condition, wherein prevention is to be understood as the management and care of a patient for the purpose of combating the disease, condition or disorder and includes the administration of the active compounds to prevent the onset of the symptoms or complications. Nonetheless, prophylactic (preventive) and therapeutic (curative) treatments are two separate aspects.

The terms "disease", "condition" and "disorder" as used herein are used interchangeably to specify a state of a patient which is not the normal physiological state of man.

The term "medicament" as used herein means a pharmaceutical composition suitable for administration of the pharmaceutically active compound to a patient.

The term "pharmaceutically acceptable" as used herein means suited for normal pharmaceutical applications, i.e. giving rise to no adverse events in patients etc.

The compounds of the invention may be obtained in crystalline form either directly by concentration from an organic solvent or by crystallisation or re-crystallisation from an organic solvent or mixture of said solvent and a co-solvent that may be organic or inorganic, such as water. The crystals may be isolated in essentially solvent-free form or as a solvate, such as a hydrate. The invention covers all crystalline modifications and forms and also mixtures thereof.

Compounds of formula (I) may or may not comprise asymmetrically substituted (chiral) carbon atoms which give rise to the existence of isomeric forms, e.g. enantiomers and possibly diastereomers. The present invention relates to all such isomers, either in optically pure form or as mixtures thereof (e.g. racemic mixtures or partially purified optical mixtures). Pure stereoisomeric forms of the compounds and the intermediates of this invention may be obtained by the application of procedures known in the art. The various isomeric forms may be separated by physical separation methods such as selective crystallization and chromatographic techniques, e.g. high pressure liquid chromatography using chiral stationary phases. Enantiomers may be separated from each other by selective crystallization of their diastereomeric salts which may be formed with optically active amines, such as I-ephedrine, or with optically active acids. Optically purified compounds may subsequently be liberated from said purified diastereomeric salts. Enantiomers may also be resolved by the formation of diastereomeric derivatives. Alternatively, enantiomers may be separated by chromatographic techniques using chiral stationary phases. Pure stereoisomeric forms may also be derived from the corresponding pure stereoisomeric forms of the appropriate starting materials, provided that the reaction occur stereoselectively or stereospecifically. If a specific stereoisomer is desired, said compound will be synthesized by stereoselective or stereospecific methods of preparation. These methods will advantageously employ chiral pure starting materials.

Furthermore, when a double bond or a fully or partially saturated ring system is present in the molecule geometric isomers may be formed. It is intended that any geometric isomer, as separated, pure or partially purified geometric isomers or mixtures thereof are included within the scope of the invention.

Medical Use

As the compounds of the invention exhibit PDE4 inhibitory activity, the compounds may be useful as therapeutic agents for inflammatory allergic diseases such as bronchial asthma, COPD, allergic rhinitis, and nephritis; autoimmune diseases such as rheumatoid arthritis, multiple sclerosis, Crohn's disease, and systemic lupus erythematosus; acute or chronic cutaneous wound disorders; diseases of the central nervous system such as depression, amnesia, and dementia; organopathy associated with ischemic reflux caused by cardiac failure, shock, and cerebrovascular diseases, and the like; insulin-resistant diabetes; wounds; AIDS, and the like.

In one embodiment, the compounds of the present invention are considered useful for the treatment, prevention or alleviation of dermal diseases or conditions.

In another embodiment, the compounds of the present invention are considered useful for the treatment, prevention or alleviation of dermal diseases or conditions selected from the group consisting of proliferative and inflammatory skin disorders, dermatitis, atopic dermatitis, seborrheic dermatitis, contact dermatitis, psoriasis, cancer, epidermal inflammation, alopecia, alopecia areata, skin atrophy, steroid induced skin atrophy, skin ageing, photo skin ageing, acne, urticaria, pruritis, and eczema.

In another embodiment, the compounds of the present invention are considered useful for the treatment or alleviation of atopic dermatitis.

In another embodiment, the compounds of the present invention are considered useful for the treatment or alleviation of psoriasis.

In another embodiment, the compounds of the present invention are considered useful for the treatment or alleviation of alopecia areata.

In another embodiment, the compounds of the present invention are considered useful for the treatment or alleviation of acne.

In another embodiment, the compounds of the present invention are considered useful for the treatment or alleviation of pruritis.

In another embodiment, the compounds of the present invention are considered useful for the treatment or alleviation of eczema.

Compounds of the invention, optionally in combination with other active compounds, may be useful for the treatment of dermal diseases or conditions, in particular for the treatment of proliferative and inflammatory skin disorders, dermatitis, atopic dermatitis, seborrheic dermatitis, contact dermatitis, psoriasis, cancer, epidermal inflammation, alopecia, alopecia areata, skin atrophy, steroid induced skin atrophy, skin ageing, photo skin ageing, acne, urticaria, pruritis, and eczema.

Besides being useful for human treatment, the compounds of the present invention may also be useful for veterinary treatment of animals including mammals such as horses, cattle, sheep, pigs, dogs, and cats.

For use in therapy, compounds of the present invention are typically in the form of a pharmaceutical composition. The invention therefore relates to a pharmaceutical composition comprising a compound of formula (I), optionally together with one or more other therapeutically active compound(s), together with a pharmaceutically acceptable excipient or vehicle. The excipient must be "acceptable" in the sense of being compatible with the other ingredients of the composition and not deleterious to the recipient thereof.

In the form of a dosage unit, the compound may be administered one or more times a day at appropriate intervals, always depending, however, on the condition of the patient, and in accordance with the prescription made by the medical practitioner. Conveniently, a dosage unit of a topical formulation contain between 0.001 mg and 1000 mg, preferably between 0.01 mg and 100 mg, such as 0.1-50 mg of a compound of formula (I).

A suitable dosage of the compound of the invention will depend, inter alia, on the age and condition of the patient, the severity of the disease to be treated and other factors well known to the practising physician. The compound may be administered either orally, parenterally or topically according to different dosing schedules, e.g. daily or with weekly intervals. In general a single dose will be in the range from 0.0001 to 10 mg/kg body weight, e.g. in the range from 0.001 to 5 mg/kg body weight. The compound may be administered as a bolus (i.e. the entire daily dosis is administered at once) or in divided doses two or more times a day.

In the context of topical treatment it may be more appropriate to refer to a "usage unit", which denotes unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers. A "usage unit" is capable of being administered topically to a patient in an application per square centimetre of the skin of from 0.1 mg to 50 mg and preferably from 0.2 mg to 5 mg of the final formulation in question.

It is also envisaged that in certain treatment regimes, administration with longer intervals, e.g. every other day, every week, or even with longer intervals may be beneficial.

If the treatment involves administration of another therapeutically active compound it is recommended to consult Goodman & Gilman's The Pharmacological Basis of Therapeutics, 9$^{th}$ Ed., J. G. Hardman and L. E. Limbird (Eds.), McGraw-Hill 1995, for useful dosages of said compounds.

The administration of a compound of the present invention with one or more other active compounds may be either concomitantly or sequentially.

The formulations include e.g. those in a form suitable for oral (including sustained or timed release), rectal, parenteral (including subcutaneous, intraperitoneal, intramuscular, intraarticular and intravenous), transdermal, ophthalmic, topical, dermal, nasal or buccal administration. Topical administration of the claimed formulation is particularly suitable.

The formulations may conveniently be presented in dosage unit form and may be prepared by but not restricted to any of the methods well known in the art of pharmacy, e.g. as disclosed in Remington, *The Science and Practice of Pharmacy*, 21ed ed., 2005. All methods include the step of bringing the active ingredient into association with the carrier, which constitutes one or more accessory ingredients. In general, the formulations are prepared by uniformly and intimately bringing the active ingredient into association with a liquid carrier, semisolid carrier or a finely divided solid carrier or combinations of these, and then, if necessary, shaping the product into the desired formulation.

Formulations of the present invention suitable for oral and buccal administration may be in the form of discrete units as capsules, sachets, tablets, chewing gum or lozenges, each containing a predetermined amount of the active ingredient; in the form of a powder, granules or pellets; in the form of a solution or a suspension in an aqueous liquid or non-aqueous liquid, such as ethanol or glycerol; or in the form of a gel, a nano- or microemulsion, an oil-in-water emulsion, a water-in-oil emulsion or other dispensing systems. The oils may be edible oils, such as but not restricted to e.g. cottonseed oil, sesame oil, coconut oil or peanut oil. Suitable dispersing or suspending agents for aqueous suspensions include synthetic or natural surfactants and viscosifying agents such as but not restricted to tragacanth, alginate, acacia, dextran, sodium carboxymethylcellulose, gelatin, methylcellulose, hydroxypropylmethylcellulose, hydroxypropylcelulose, carbomers, polyvinylpyrrolidone, polysorbates, sorbitan fatty acid esters. The active ingredients may also be administered in the form of a bolus, electuary or paste.

A tablet may be made by compressing, moulding or freeze drying the active ingredient optionally with one or more accessory ingredients. Compressed tablets may be prepared by compressing, in a suitable machine, the active ingredient(s) in a free-flowing form such as a powder or granules, optionally mixed by a binder and/or filler, such as e.g. lactose, glucose, mannitol starch, gelatine, acacia gum, tragacanth gum, sodium alginate, calcium phosphates, microcrystalline cellulose, carboxymethyl-cellulose, methylcellulose, hydroxypropylcellulose, hydroxypropylmethylcellulose, ethylcellulose, hydroxyethylcellulose, polyethylene glycol, waxes or the like; a lubricant such as e.g. sodium oleate, sodium stearate, magnesium stearate, sodium benzoate, sodium acetate, sodium chloride or the like; a disintegrating agent such as e.g. starch, methylcellulose, agar, bentonite, croscarmellose sodium, sodium starch glycollate, crospovidone or the like or a dispersing agent, such as polysorbate 80. Moulded tablets may be made by moulding, in a suitable machine, a mixture of the powdered active ingredient and suitable carrier moistened with an inert liquid diluent. Freeze dried tablets may be formed in a freeze-dryer from a solution of the drug substance. A suitable filler can be included.

Formulations for rectal administration may be in the form of suppositories in which the compound of the present invention is admixed with low melting point, water soluble or insoluble solids such as cocoa butter, hydrogenated vegetable oils, polyethylene glycol or fatty acids esters of polyethylene glycols, while elixirs may be prepared using myristyl palmitate.

Formulations suitable for parenteral administration conveniently comprise a sterile oily or aqueous preparation of the active ingredients, which is preferably isotonic with the blood of the recipient, e.g. isotonic saline, isotonic glucose solution or buffer solution. Furthermore, the formulation may contain cosolvent, solubilising agent and/or complexation agents. The formulation may be conveniently sterilised by for instance filtration through a bacteria retaining filter, addition of sterilising agent to the formulation, irradiation of the formulation or heating of the formulation. Liposomal formulations as disclosed in e.g. Encyclopedia of Pharmaceutical Technology, vol. 9, 1994, are also suitable for parenteral administration.

Alternatively, the compounds of formula (I) may be presented as a sterile, solid preparation, e.g. a freeze-dried powder, which is readily dissolved in a sterile solvent immediately prior to use.

Transdermal formulations may be in the form of a plaster, patch, microneedles, liposomal or nanoparticulate delivery systems or other cutaneous formulations applied to the skin.

Formulations suitable for ophthalmic administration may be in the form of a sterile aqueous preparation of the active ingredients, which may be in microcrystalline form, for example, in the form of an aqueous microcrystalline suspension. Liposomal formulations or biodegradable polymer systems e.g. as disclosed in Encyclopedia of Pharmaceutical Technology, vol. 2, 1989, may also be used to present the active ingredient for ophthalmic administration.

Formulations suitable for topical, such as dermal, intradermal or ophthalmic administration include liquid or semisolid preparations such as liniments, lotions, gels, applicants, sprays, foams, filmforming systems, microneedles, micro- or nano-emulsions, oil-in-water or water-in-oil emulsions such as creams, ointments or pastes; or solutions or suspensions such as drops. Compositions for ophthalmic treatment may additionally contain cyclodextrin.

For topical administration, the compound of formula (I) may typically be present in an amount of from 0.001 to 20% by weight of the composition, such as 0.01% to about 10%, but may also be present in an amount of up to about 100% of the composition.

Formulations suitable for nasal or buccal administration include powder, self-propelling and spray formulations, such as aerosols and atomisers. Such formulations are disclosed in greater detail in e.g. Modern Pharmaceutics, $2^{nd}$ ed., G. S. Banker and C. T.

Rhodes (Eds.), page 427-432, Marcel Dekker, New York; Modern Pharmaceutics, $3^{th}$ ed., G. S. Banker and C. T. Rhodes (Eds.), page 618-619 and 718-721, Marcel Dekker, New York and Encyclopedia of Pharmaceutical Technology, vol. 10, J. Swarbrick and J. C. Boylan (Eds), page 191-221, Marcel Dekker, New York.

In addition to the aforementioned ingredients, the formulations of a compound of formula (I) may include one or more additional ingredients such as diluents, buffers, flavouring agents, colourant, surface active agents, thickeners, penetration enhancing agents, solubility enhancing agents preservatives, e.g. methyl hydroxybenzoate (including antioxidants), emulsifying agents and the like.

When the active ingredient is administered in the form of salts with pharmaceutically acceptable non-toxic acids or bases, preferred salts are for instance easily water-soluble or slightly soluble in water, in order to obtain a particular and appropriate rate of absorption.

The pharmaceutical composition may additionally comprise one or more other active components conventionally used in the treatment of dermal disease or conditions, e.g. selected from the group consisting of glucocorticoids, vitamin D and vitamin D analogues, antihistamines, platelet activating factor (PAF) antagonists, anticholinergic agents, methylxanthines, β-adrenergic agents, COX-2 inhibitors, JAK inhibitors, other PDEs, salicylates, indomethacin, flufenamate, naproxen, timegadine, gold salts, penicillamine, serum cholesterol lowering agents, retinoids, zinc salts, salicylazosulfapyridine and calcineurin inhibitors.

Methods of Preparation

The compounds of the present invention can be prepared in a number of ways well known to those skilled in the art of synthesis. The compounds of formula (I) may for example be prepared using the reactions and techniques outlined below together with methods known in the art of synthetic organic chemistry, or variations thereof as appreciated by those skilled in the art. Preferred methods include, but are not limited to, those described below. The reactions are carried out in solvents appropriate to the reagents and materials employed and suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognized by one skilled in the art. Not all compounds falling into a given class may be compatible with some of the reaction conditions required in some of the methods described. Such restrictions to the substituents which are compatible with the reaction conditions will be readily apparent to one skilled in the art and alternative methods can be used.

The compounds of the present invention or any intermediate may be purified if required using standard methods well known to a synthetic organist chemist, e.g. methods described in "Purification of Laboratory Chemicals", $6^{th}$ ed. 2009, W. Amarego and C. Chai, Butterworth-Heinemann.

Starting materials are either known or commercially available compounds or can be prepared by routine synthetic methods well known to a person skilled in the art.

$^1$H nuclear magnetic resonance (NMR) spectra were recorded at 300 or 600 MHz unless otherwise specified. Chemical shift values (δ, in ppm) are quoted relative to internal tetramethylsilane (δ=0.00) standards. The value of a multiplet, either defined doublet (d), triplet (t), quartet (q) or (m) at the approximate midpoint is given unless a range is quoted. (br) indicates a broad peak, whilst (s) indicates a singlet. The organic solvents used were usually anhydrous. Chromatography was performed on Merck silica gel 60 (0.040-0-063 mm). The solvent ratios indicated refer to v:v unless otherwise noted. All NMR spectra are recorded in DMSO-$d_6$ unless another solvent is stated.

Analytical UPLC/MS

Analytical UPLC/MS is performed on a Waters Acquity UPLC-system and SQD-MS. Column: Waters Acquity HSS T3 1.8 μm, 2.1×50 mm; solvent system: A=10 mM Ammonium acetate in water+0.1% HCOOH and B=acetonitrile+ 0.1% HCOOH; flow rate=1.2 mL/min; method (1.4 min): Linear gradient method from 5% B to 95% B over 0.9 minutes then 95% B for 0.3 minutes. Column temperature is 60° C.

Preparative Purification HPLC/MS:

Preparative HPLC/MS was performed on a Waters AutoPurification system with a Waters SQD2 mass spectrometer. This includes three steps, pre-analysis, preparative purification and re-analysis on the purified compound.

Solvent: A=0.1% formic acid and solvent B=acetonitrile with 0.1% formic acid.

Analytical pre-analysis using the following method:
Column: Waters SUNFIRE C-18, 100 mm×4.6 mm, 5 μm
Flow rate=1.2 mL/min. (method 10 min)
Method: Linear gradient method going from 10% B to 95% B in 6.5 minutes and staying at 95% B for another 1.5 minutes to obtain the retention time of the compounds provides the following four different preparative gradient methods:

Preparative Methods:
Column: Waters SUNFIRE C-18, 100 mm×19 mm, 5 μm
Flow rate=20 mL/min. (method 8 min)
0-3 min: 5% B for 2 minutes followed by a linear gradient method going from 5% B to 35% B in 3 minutes and going to 100% B and staying at 100% B for another 1.4 minutes.

3.01-5 min: 15% B for 1 minutes followed by a linear gradient method going from 15% B to 55% B in 4 minutes and going to 100% B and staying at 100% B for another 1.4 minutes.

5.01-7.5 min: 30% B for 1 minutes followed by a linear gradient method going from 30% B to 70% B in 4 minutes and going to 100% B and staying at 100% B for another 1.4 minutes.

7.51-10 min: 50% B for 1 minutes followed by a linear gradient method going from 50% B to 100% B in 4 minutes and staying at 100% B for another 1.5 minutes.

The fractions were collected based on ion traces of relevant ions and PDA signal (240-400 nm).

Re-Analysis Method for Fractions:
Column: Waters Xselect C18; 50×3.0 mm 5 μm
Flow rate=1.2 mL/min. (method 5 min)
Method: Linear gradient method going from 10% B to 95% B in 3 minutes and staying at 95% B for another 0.5 min.

Instruments:
Waters 2767 Sample Manager
Waters 2545 Binary Gradient Module

Waters SFO System Fluidics Organizer
Waters 515 HPLC Pump
Waters 2998 Photodiode Array Detector
Waters SQDetector 2
LCMS Method "XE Metode 7 CM"

A quality check was performed on a Waters LCT Premier MS instrument and a Waters Aquity UPLC.

Column: Waters Aquity UPLC HSS T3 1.8 μm, 2.1×50 mm, at 40° C.

Solvents: A=10 mM ammonium acetate+0.1% HCOOH, B=ACN+0.1% HCOOH.

Flow: 0.7 ml/min. Injection volume 2 μl. UV detection range 240-400 nm.

| Gradient: | | |
|---|---|---|
| Time | % A | % B |
| 0.00 min | 99 | 1 |
| 0.50 min | 94 | 6 |
| 1.00 min | 94 | 6 |
| 2.60 min | 5 | 95 |
| 3.80 min | 5 | 95 |
| 3.81 min | 99 | 1 |
| 4.80 min | 99 | 1 |

The MW confirmation and purity was extracted and checked with OpenLynx.

The following abbreviations have been used throughout:
ACN acetonitrile
BOC tert-butyloxycarbonyl
DCC N,N'-dicyclohexylcarbodiimide
DCE 1,2-dichloroethane
DCM dichloromethane
DMAP N,N-dimethylpyridin-4-amine
DMF N,N-dimethylformamide
DMSO dimethylsulfoxide
EDAC (3-dimethylamino-propyl)-ethyl-carbodiimide
EtOH ethanol
EtOAc ethyl acetate
EtONa sodium ethoxide
$Et_3N$ triethylamine
h hour
KOH potassium hydroxide
L litre
LAH lithium aluminium hydride
Me methyl
MeOH methanol
min minutes
$NaN_3$ natriumazid
NMR nuclear magnetic resonance
PG protecting group
PPTS pyridinium p-toluenesulfonate
rt room temperature
TBME tert-butyl methyl ether
TFA trifluoroacetic acid
THF tetrahydrofuran General Methods Compounds of general formula (I) of the invention may for example be prepared according to the following non-limiting general methods and examples. $R_1$, $R_2$, $R_3$, $R_4$, Q and n are as previously defined for the compounds of general formula (I):

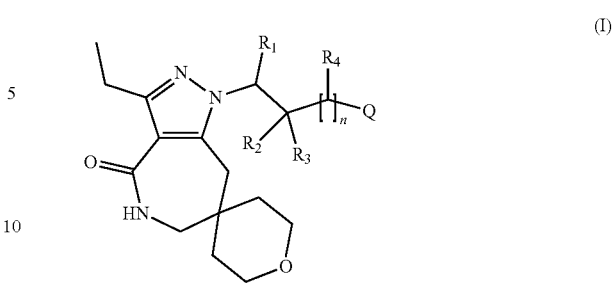

(I)

a) Synthesis of Compound 004 is outlined in Scheme 1

Compound 004 is prepared as described in WO 2008/110308 in three steps.

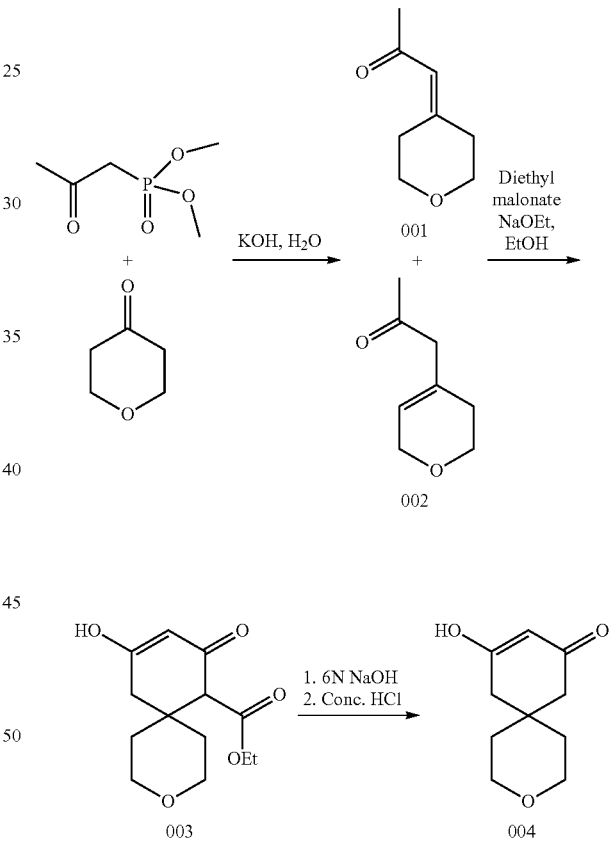

b) Synthesis of compound 006 is outlined in Scheme 2

Compound 006 is prepared according to standard procedures known to a chemist skilled in the art of organic synthesis. Reaction of compound 004 with propionyl chloride or propionic anhydride in the presence of a base such as pyridine, triethylamine, or diisopropylethylamine in a solvent such as DCM, THF gives compound 005. Treatment of acetone cyanohydrin, $Et_3N$ delivers compound 006.

Scheme 2

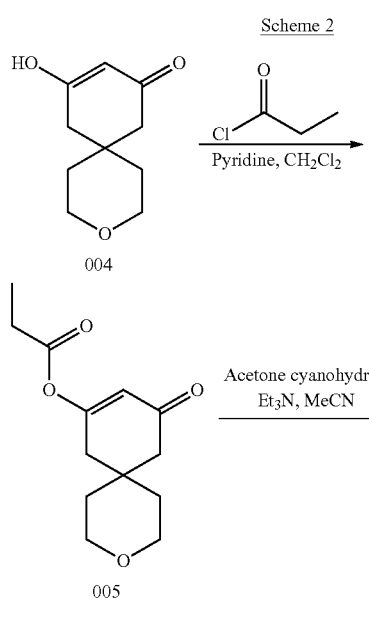

c) Synthesis of a compound of general formula (V) is outlined in Scheme 3

A compound of general formula (II) may be prepared by treatment of compound 006 with a compound of general formula (III) in the presence of a suitable acid such as acetic acid and 4-toluenesulphonic acid or in the absence of an acid in a suitable solvent such as methanol, ethanol, propanol, isopropanol, butanol, and THF at suitable temperature between rt and 150° C. (preferably 50° C. to 120° C.).

A compound of general formula (II) may also be prepared by treatment of compound 006 with a compound of formula (III) in the presence of a suitable base such as triethylamine, $K_2CO_3$, $Bu_4NOH$, KOH in a suitable solvent such as methanol, ethanol, propanol, isopropanol, butanol, and THF at suitable temperature between rt and 150° C. (preferably 50° C. to 120° C.), especially when a compound of general formula (II) is in a salt form such as hydrochloride and oxalate.

A compound of general formula (III) may be commercially available or prepared according to standard procedures known to a chemist skilled in the art of organic synthesis (for examples, see: Gever, Gabriel, J. Am. Chem. Soc. (1954), 76, 1283-1285; Ghali, N. I. J. Org. Chem. (1981), 46 (26), 5413-14; Kim, Yongju, ACS Medicinal Chemistry Letters (2012), 3 (2), 151-154). The protecting group may be acyl such as acetyl and benzoyl or tetrahydrapyranyl, but not limited to these.

A compound of general formula (IV) may be prepared by procedures similar to those described, for example, by Bardakos, Vasilios et al. Chem Ber. (1976), 109, 1898-1910; Wang, Xiao-Feng et al. J. Med. Chem. (2014), 57 (4), 1390-1402. Typically, a compound of general formula (IV) may be prepared by treatment of formula (II) with hydrazoic acid, sodium azide or trimethylsilyl azide in the presence of a suitable Brønsted-Lowry acid such as hydrochloride, sulfuric acid, methanesulfonic acid, trifluoroacetic acid, phosphoric acid, trifluoromethanesulfonic acid, and trifluoroborane etherate or a mixture of two or more of these in the presence of a suitable Lewis acid such as trifluoroborane etherate in a suitable solvent such as water, dichloromethane, chloroform, acetic acid, methanesulfonic acid, toluene, and benzene or a mixture of two or more of these at a suitable temperature between 0° C. to 100° C.

A compound of formula (V) represents a protected alcohol. A compound of general formula (IV) may be prepared by removal of a protecting group according to standard procedures known to a chemist skilled in the art of organic synthesis (for a review on protecting group, see: Kocienski, Philip J. Protecting groups, Georg Thieme Verlag, Stuttgart, New York, 2004).

Scheme 3

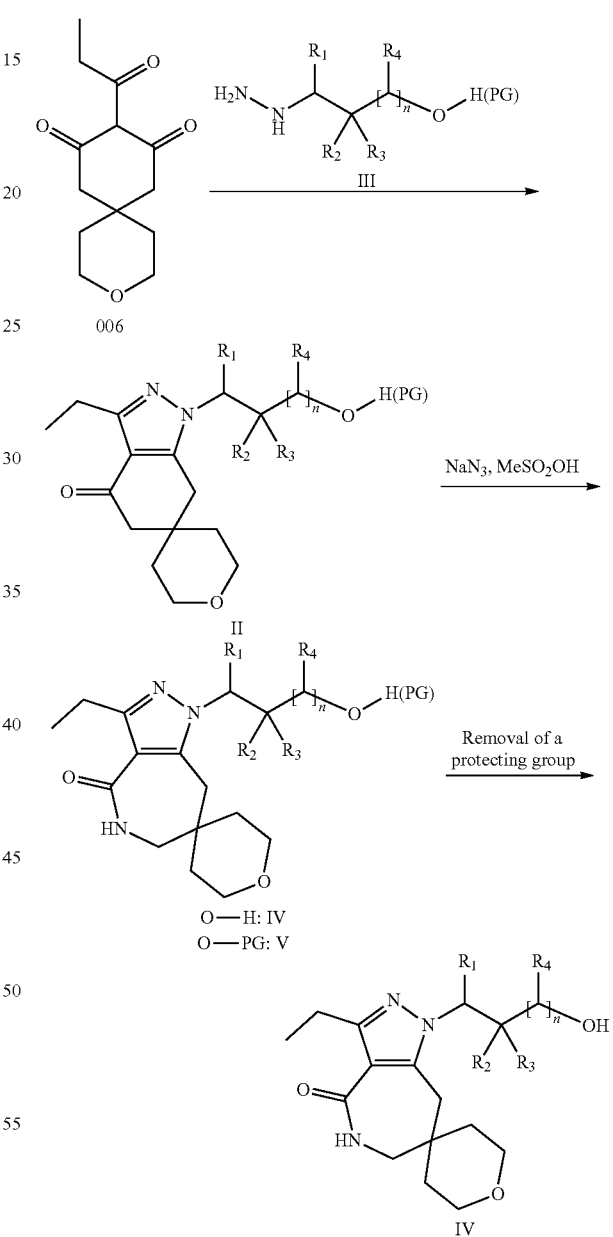

PG = Protecting group d) Synthesis of a compound of general formula I where Q represents —O—C(O)—$R_5$, wherein $R_5$ is as previous defined, is outlined in Scheme 4

A compound of general formula (I) where Q represents —O—C(O)—$R_5$ may be prepared from a compound of formula (IV) according to standard procedures known to a chemist skilled in the art of organic synthesis (for ester formation, see: Junzo Otera, Esterification: Methods, Reactions, and Applications, Wiley-VCH, Weinheim (2004)).

For example, a compound of general formula (I) may be prepared by reaction of a compound of general formula (IV) with HO—(CO)—R$_5$ in the presence of a suitable couplings reagent such as DCC, EDAC and a suitable catalyst such as DMAP in a suitable solvent such dichloromethane, dichloroethane, acetonitrile and ethyl acetate.

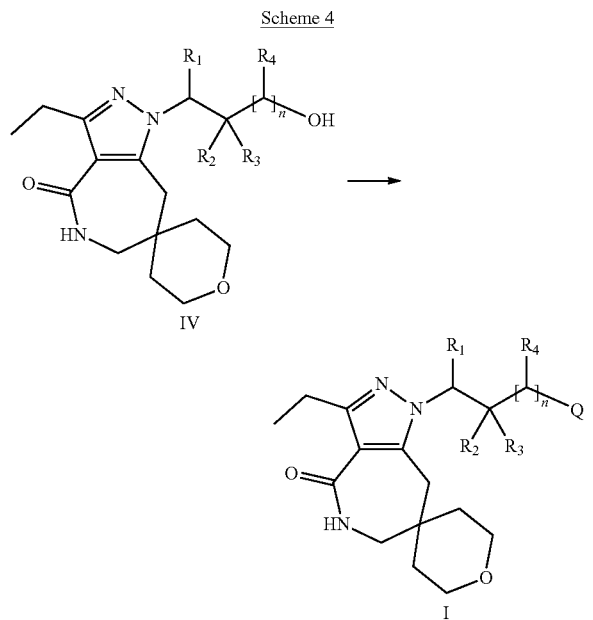

Scheme 4

PREPARATIONS AND EXAMPLES

Preparation 1 (Compounds 001 and 002)

1-Tetrahydropyran-4-ylidenepropan-2-one and 1-(3,6-dihydro-2H-pyran-4-yl)propan-2-one

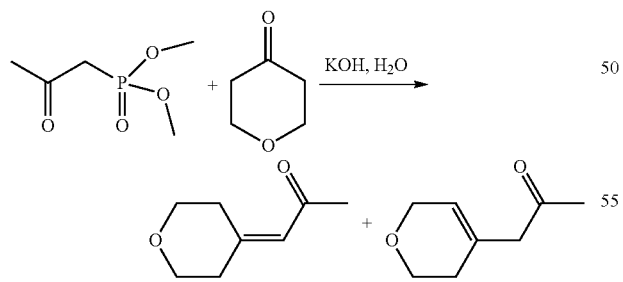

To a solution of KOH (40 g, 722.9 mmol) in H$_2$O (200 mL) and EtOH (800 mL) at 0° C., 1-dimethoxyphosphoryl-propan-2-one (100 g, 602.04 mmol) in EtOH (100 mL) and tetrahydropyran-4-one (60 g, 602.04 mmol) in EtOH (100 mL) were added and stirred at 26° C. for 4 h. On completion of the reaction, excess solvent was evaporated under vacuum and the resulting residue was treated with water (200 mL) and extracted with diethyl ether (2×200 mL). The combined organic layers were washed with brine (200 mL), dried over Na$_2$SO$_4$ and concentrated in vacuum to afford the title compounds as pale yellow liquid (crude). The crude was used in the next step without any further purification.

Preparation 2 (Compound 003)

Ethyl 8-hydroxy-10-oxo-3-oxaspiro[5.5]undec-8-ene-11-carboxylate

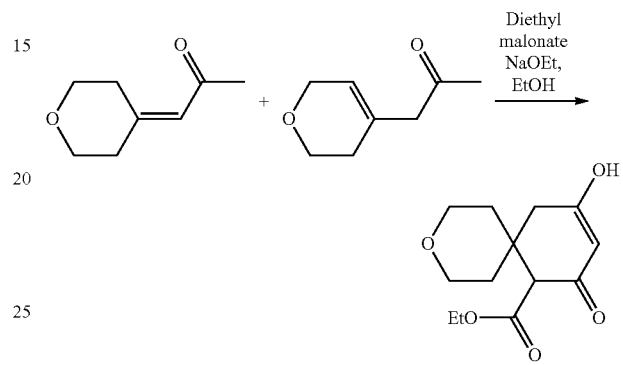

To a solution of EtONa (97.14 g, 1428 mmol) in ethanol (800 mL), diethyl malonate (114 g, 714.28 mmol) and 1-tetrahydropyran-4-ylidenepropan-2-one and 1-(3,6-dihydro-2H-pyran-4-yl)propan-2-one (100 g, 713.3 mmol) in EtOH (200 mL) were added slowly and stirred at reflux temperature for 16 h. On completion excess solvent was evaporated under vacuum to afford the title compound as brown solid (crude). The crude was used in the next step without any further purification.

Preparation 3 (Compound 004)

8-Hydroxy-3-oxaspiro[5.5]undec-8-en-10-one

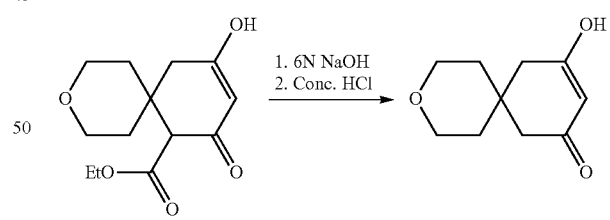

To ethyl 8-hydroxy-10-oxo-3-oxaspiro[5.5]undec-8-ene-11-carboxylate (100 g, 393.3 mmol), 6N NaOH (1 L) was added and stirred for 16 h at 26° C. Then conc.HCl (500 mL) was added slowly at 0° C. to adjust the pH to ~2 and refluxed for 4 h. On completion of the reaction, the reaction mixture was treated with water and extracted twice with EtOAc (2×500 mL). The combined organic layers were washed with brine (500 mL), dried over Na$_2$SO$_4$, concentrated in vacuo and purified by washings with diethyl ether to afford the title compound as a brown solid.

$^1$H NMR (300 MHz, DMSO-d$_6$) δ 11.02 (s, 1H), 5.19 (s, 1H), 3.71-3.45 (m, 4H), 2.29 (s, 4H), 1.45 (t, J=5.4 Hz, 4H).

Preparation 4 (Compound 005)

(10-Oxo-3-oxaspiro[5.5]undec-8-en-8-yl) Propanoate

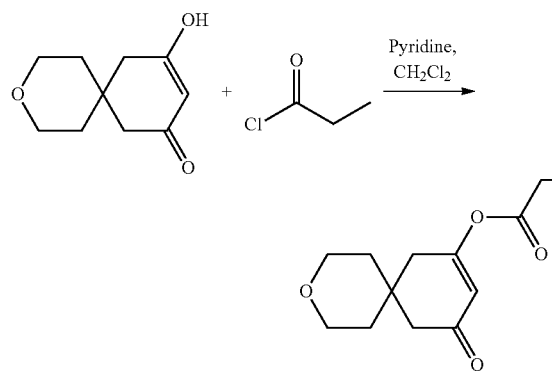

To a solution of 8-hydroxy-3-oxaspiro[5.5]undec-8-en-10-one (90 g, 494.5 mmol) in DCM (1.5 L), pyridine (58.6 g, 741.7 mmol) and propionyl chloride (45.5 g, 494.5 mmol) were added slowly at 0° C. and the reaction mixture was subsequently stirred for 4 h at 26° C. On completion the reaction mixture was treated with 1N.HCl and the organic layer was washed with brine (700 mL), dried over $Na_2SO_4$ and concentrated to afford the title compound as brown liquid.

$^1$H NMR (300 MHz, $CDCl_3$) δ 5.91 (d, J=1.2 Hz, 1H), 3.68 (t, J=5.4 Hz, 4H), 2.56 (d, J=1.3 Hz, 2H), 2.51 (q, J=7.5, 2H), 2.44 (s, 2H), 1.73-1.49 (m, 4H), 1.22 (t, J=7.5, 3H).

Preparation 5 (Compound 006)

9-Propanoyl-3-oxaspiro[5.5]undecane-8,10-dione

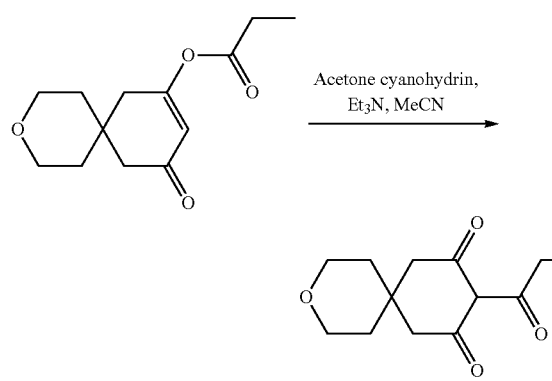

To a solution of (10-oxo-3-oxaspiro[5.5]undec-8-en-8-yl) propanoate (90 g, 378.15 mmol) in ACN (1500 mL), $Et_3N$ (38.2 g, 378.15 mmol) and acetone cyanohydrin (48 g, 567.22 mmol) were added at 0° C. and stirred for 3 h at 26° C. On completion excess solvent was evaporated under vacuum and the resulting residue was purified by silica gel column chromatography (1% MeOH in DCM as eluent) to afford the title compound as a pale yellow liquid.

$^1$H NMR (300 MHz, $CDCl_3$) δ 3.77-3.58 (m, 4H), 3.06 (q, J=7.2 Hz, 2H), 2.67 (s, 2H), 2.51 (s, 2H), 1.62-1.47 (m, 4H), 1.13 (t, J=7.3 Hz, 3H).

Preparation 6 (Compound 007)

Ethyl 2-(3-ethyl-4-oxo-spiro[5,7-dihydroindazole-6,4'-tetrahydropyran]-1-yl)acetate

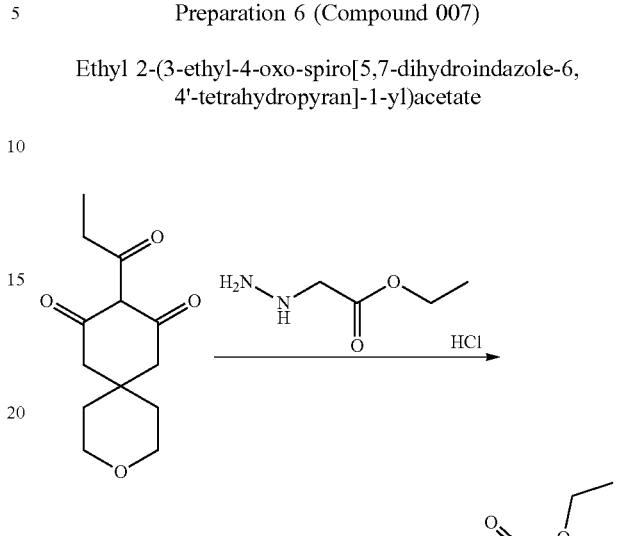

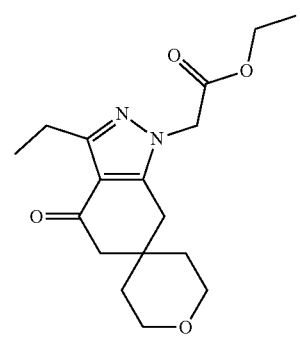

A mixture of 9-propanoyl-3-oxaspiro[5.5]undecane-8,10-dione (218 mg, 0.91 mmol), triethylamine (0.255 mL, 1.83 mmol) and ethyl 2-hydrazinoacetate hydrochloride (141 mg, 0.91 mmol) was stirred at 80° C. for 1 hour. The reaction mixture was concentrated in vacuo. Column chromatography (25-66% of EtOAc in heptane as eluent) afforded the title compound (278 mg, 95% yield) as pale yellow oil.

$^1$H NMR (300 MHz, $CDCl_3$) δ 4.81 (s, 2H), 4.25 (q, J=7.1 Hz, 2H), 3.79-3.59 (m, 4H), 2.86 (q, J=7.5 Hz, 2H), 2.73 (s, 2H), 2.53 (s, 2H), 1.72-1.52 (m, 4H), 1.38-1.16 (m, 6H).

Preparation 7 (Compound 008)

Ethyl 2-(3-ethyl-4-oxo-spiro[6,8-dihydro-5H-pyrazolo[4,3-c]azepine-7,4'-tetrahydropyran]-1-yl)acetate

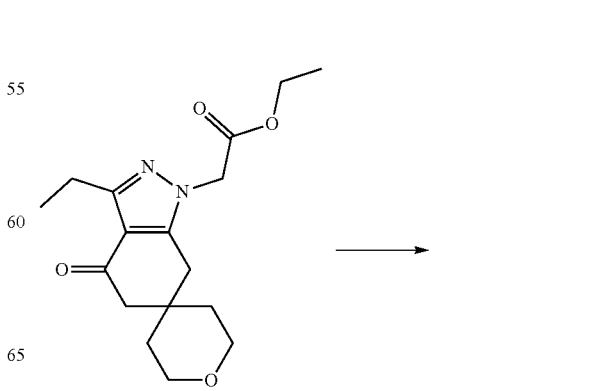

-continued

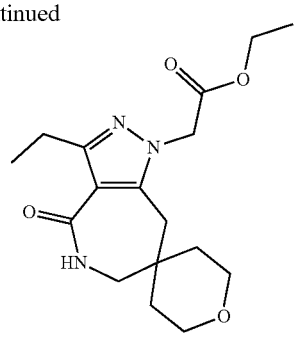

Methanesulfonic acid (1 mL) was added to a mixture of ethyl 2-(3-ethyl-4-oxo-spiro[5,7-dihydroindazole-6,4'-tetrahydropyran]-1-yl)acetate (1.4 g, 4.37 mmol) and sodium azide (0.85 g, 13.1 mmol) in dry chloroform. The mixture was stirred at rt for 15 minutes before additional methane sulfonic acid (2 mL) was added. The mixture was stirred at rt for another 15 minutes before additional methane sulfonic acid (2 mL) was added. The mixture was stirred at rt for 45 minutes. Finally, additional sodium azide (852 mg, 13.1 mmol) and methanesulfonic acid (2 mL) was added. The mixture was stirred at rt for 1 hour. The reaction was quenched with saturated, aqueous NaHCO$_3$ (120 mL) and extracted three times with DCM (3×50 mL). The combined organic phases were concentrated in vacuo. Column chromatography (20-100% EtOAc in heptane as eluent) gave the title compound (550 mg, 38% yield).

$^1$H NMR (300 MHz, CDCl$_3$) δ 5.74 (t, J=5.8 Hz, 1H), 4.81 (s, 2H), 4.24 (q, J=7.1 Hz, 2H), 3.79-3.60 (m, 4H), 3.21 (d, J=5.8 Hz, 2H), 2.91 (q, J=7.5 Hz, 2H), 2.69 (s, 2H), 1.68-1.54 (m, 4H), 1.33-1.21 (m, 6H).

Preparation 8 (Compound 009)

3-Ethyl-1-(2-hydroxyethyl)spiro[6,8-dihydro-5H-pyrazolo[4,3-c]azepine-7,4'-tetrahydropyran]-4-one

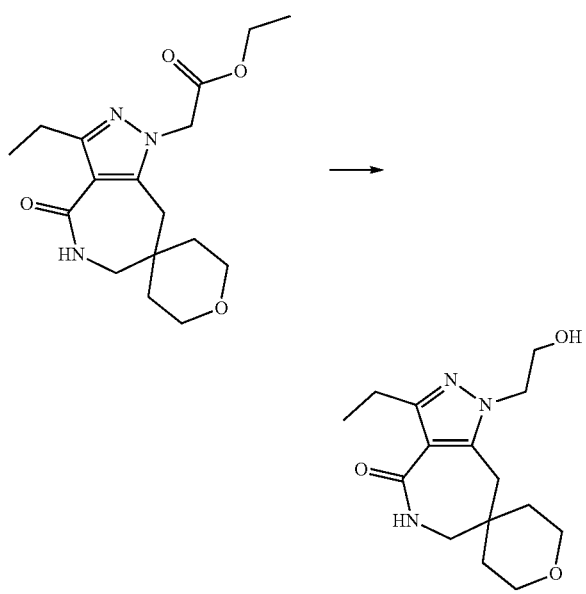

To a solution of ethyl 2-(3-ethyl-4-oxo-spiro[6,8-dihydro-5H-pyrazolo[4,3-c]azepine-7,4'-tetrahydropyran]-1-yl)acetate (546 mg, 1.63 mmol) in THF:H$_2$O (2:1, 12 mL) was added lithium borohydride (185 mg, 4.88 mmol). The mixture was stirred at rt for 1 hour. Saturated, aqueous NH$_4$Cl (10 mL) was added. The obtained mixture was stirred at rt for 5 minutes and extracted 10 times with DCM (10×20 mL) (Note that the product was very soluble in water). The combined organic phases were dried over MgSO$_4$ and filtered. Evaporation to dryness afforded the title compound (422 mg, 88% yield).

$^1$H NMR (300 MHz, DMSO-d6) δ 7.37 (t, J=5.7 Hz, 1H), 4.01 (t, J=5.6 Hz, 2H), 3.75-3.46 (m, 6H), 3.00 (d, J=5.7 Hz, 2H), 2.82 (s, 2H), 2.73 (q, J=7.5 Hz, 2H), 1.56-1.32 (m, 4H), 1.12 (t, J=7.5 Hz, 3H).

HPLC-Retention time (XE Metode 7 CM): 1.57 minutes. Detected "M+1"-mass: 294.18.

Preparation 9 (Compound 010)

3-Hydrazinopropan-1-ol

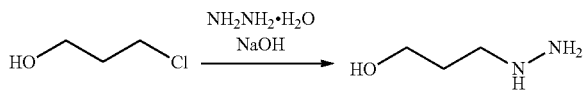

A solution of NaOH (42.5 g, 1063 mmol) and N$_2$H$_4$.H$_2$O (269.5 g, 5319 mmol) was heated up to 100° C., 3-chloropropan-1-ol (100 g, 1063 mmol) was added at same temperature and stirred for 5 h. On completion excess solvent was evaporated under vacuum. The resulting residue was treated with EtOH and the resulting solid was filtered off. The filtrate was concentrated and the excess N$_2$H$_4$.H$_2$O was removed under downward distillation, to afford the title compound as a colorless liquid (crude), which was used in the next step without any further purification.

Preparation 10 (Compound 011)

3-Ethyl-1-(3-hydroxypropyl)spiro[5,7-dihydroindazole-6,4'-tetrahydropyran]-4-one

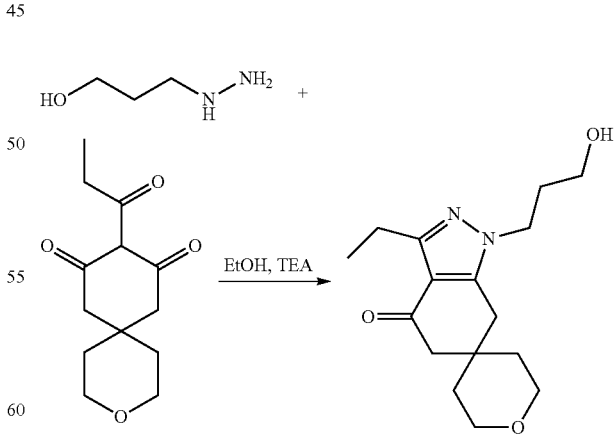

To a solution of 9-propanoyl-3-oxaspiro[5.5]undecane-8,10-dione (160 g, 671.7 mmol) in ethanol (1.6 L), Et$_3$N (135.7 g, 1344.5 mmol) and 3-hydrazinopropan-1-ol (72.6 g, 806 mmol) were added slowly and stirred at 80° C. for 16 hours. On completion excess solvent was evaporated under vacuum and the resulting residue was purified by silica gel (100-200 mesh) column chromatography (5% MeOH in DCM as eluent) to afford the title compound as a yellow liquid.

$^1$H NMR (300 MHz, CDCl$_3$) δ 4.24-4.13 (m, 2H), 3.71 (t, J=5.4 Hz, 4H), 3.61 (td, J=5.8, 2.2 Hz, 2H), 2.95-2.76 (m, 4H), 2.52 (s, 2H), 2.13-1.95 (m, 2H), 1.73-1.50 (m, 4H), 1.23 (t, J=7.5 Hz, 3H).

HPLC-Retention time (XE Metode 7 CM): 1.59 minutes.

Detected "M+1"-mass: 308.19.

Preparation 11 (Compound 012)

3-(3-Ethyl-4-oxo-spiro[5,7-dihydroindazole-6,4'-tetrahydropyran]-1-yl)propyl Benzoate

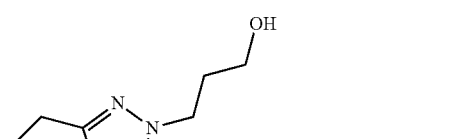

To a solution of 3-ethyl-1-(3-hydroxypropyl)spiro[5,7-dihydroindazole-6,4'-tetrahydropyran]-4-one (160 g, 547.9 mmol) in DCM (1.6 L), Et$_3$N (138.3 g, 1369.8 mmol) and benzoyl chloride (153.4 g, 1095.9 mmol) were added slowly at 0° C. and stirred for 16 h at 26° C. On completion of the reaction, volatiles were evaporated under vacuum and the resulting residue was treated with water. The organic layer was washed with brine (500 mL), dried over Na$_2$SO$_4$, concentrated and purified by silica gel (100-200 mesh) column chromatography (70% EtOAc in heptane as eluent) to afford the title compound as a pale yellow liquid, which was used directly in the next step.

Preparation 12 (Compound 013)

3-(3-Ethyl-4-oxo-spiro[6,8-dihydro-5H-pyrazolo[4,3-c]azepine-7,4'-tetrahydropyran]-1-yl)propyl Benzoate

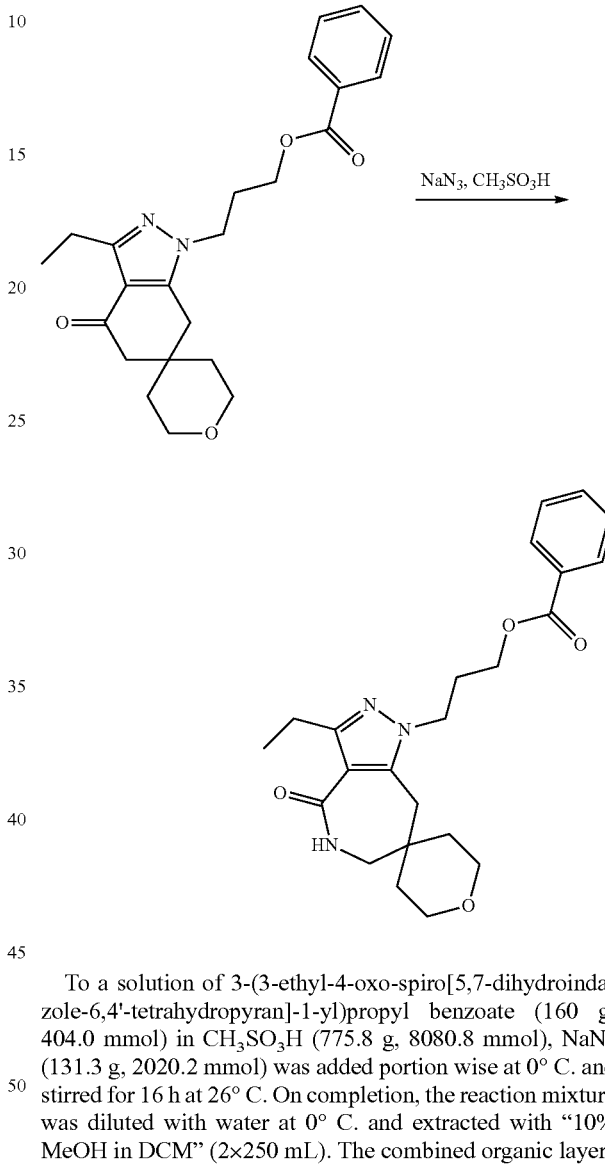

To a solution of 3-(3-ethyl-4-oxo-spiro[5,7-dihydroindazole-6,4'-tetrahydropyran]-1-yl)propyl benzoate (160 g, 404.0 mmol) in CH$_3$SO$_3$H (775.8 g, 8080.8 mmol), NaN$_3$ (131.3 g, 2020.2 mmol) was added portion wise at 0° C. and stirred for 16 h at 26° C. On completion, the reaction mixture was diluted with water at 0° C. and extracted with "10% MeOH in DCM" (2×250 mL). The combined organic layers were dried over Na$_2$SO$_4$, concentrated and purified by silica gel (100-200 mesh) column chromatography (5% MeOH in DCM as eluent) to afford the title compound as pale yellow liquid.

$^1$H NMR (600 MHz, DMSO-d$_6$) δ 7.99-7.86 (m, 2H), 7.75-7.59 (m, 1H), 7.52 (t, J=7.8 Hz, 2H), 7.40 (t, J=5.8 Hz, 1H), 4.27 (t, J=5.9 Hz, 2H), 4.16 (t, J=6.7 Hz, 2H), 3.57 (dt, J=12.0, 4.9 Hz, 2H), 3.49 (ddd, J=11.7, 6.8, 4.7 Hz, 2H), 2.98 (d, J=5.8 Hz, 2H), 2.75 (s, 2H), 2.72 (q, J=7.5 Hz, 2H), 2.20 (p, J=6.5 Hz, 2H), 1.44-1.30 (m, 4H), 1.09 (t, J=7.5 Hz, 3H).

HPLC-Retention time (XE Metode 7 CM): 2.04 minutes.

Detected "M+1"-mass: 412.23.

Preparation 13 (Compound 014)

3-Ethyl-1-(3-hydroxypropyl)spiro[6,8-dihydro-5H-pyrazolo[4,3-c]azepine-7,4'-tetrahydropyran]-4-one

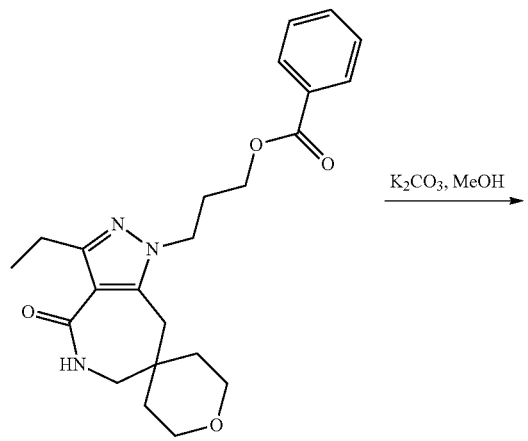

To a solution of 3-(3-ethyl-4-oxo-spiro[6,8-dihydro-5H-pyrazolo[4,3-c]azepine-7,4'-tetrahydropyran]-1-yl)propyl benzoate (85 g, 207 mmol) in MeOH (850 mL), K$_2$CO$_3$ (57 g, 414 mmol) was added at 0° C. and stirred for 3 h at 26° C. On completion, the reaction was filtered. The solid was washed with MeOH. The filtrate was concentrated and purified by Neutral Alumina column chromatography (5% MeOH in DCM as eluent) to afford the title compound as off-white solid.

$^1$H NMR (400 MHz, DMSO-d$_6$) δ 7.39 (t, J=5.7 Hz, 1H), 4.58 (s, 1H), 4.01 (t, J=7.1 Hz, 2H), 3.77-3.46 (m, 4H), 3.38 (t, J=6.0 Hz, 2H), 3.01 (d, J=5.7 Hz, 2H), 2.85-2.66 (m, 4H), 1.84 (p, J=6.5 Hz, 2H), 1.44 (t, J=5.6 Hz, 4H), 1.11 (t, J=7.5 Hz, 3H).

HPLC-Retention time (XE Metode 7 CM): 1.59 minutes.
Detected "M+1"-mass: 308.19.

Preparation 14 (Compound 015)

Methyl (2S)-2-methyl-3-tetrahydropyran-2-yloxy-propanoate

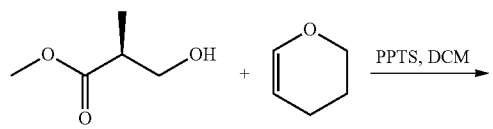

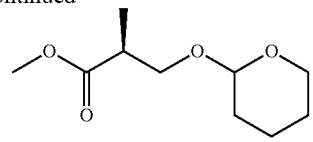

Methyl (2S)-3-hydroxy-2-methyl-propanoate (30 g, 356 mmol) was added to a solution of 3,4-dihydro-2H-pyran (16 g, 135 mmol) and PPTS (2 g, 8 mmol) in DCM (50 mL) at rt. After 2 h, the reaction was washed with H$_2$O (100 mL), saturated aqueous NaHCO$_3$ (100 mL) and with brine (100 mL). The organic phase was dried over MgSO$_4$ and concentrated in vacuo to afford the title compound as a colorless liquid, which was used in the next step without characterization.

Preparation 15 (Compound 016)

(2R)-2-Methyl-3-tetrahydropyran-2-yloxy-propan-1-ol

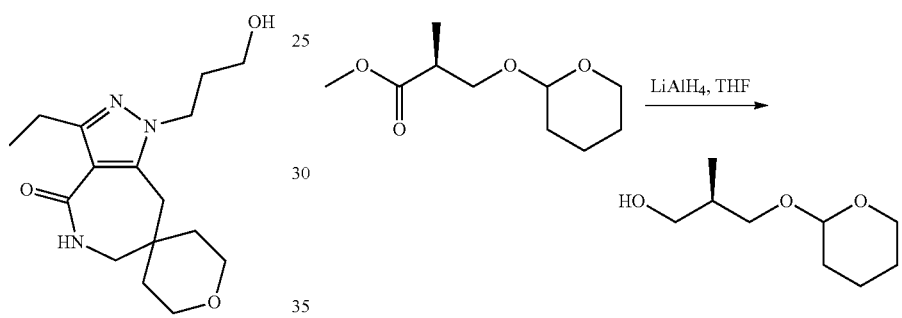

Methyl (2S)-2-methyl-3-tetrahydropyran-2-yloxy-propanoate (31 g, 153 mmol) was cooled to 0° C. and treated dropwise with 1 M LAH in THF (200 mL, 200 mmol). The solution was stirred at rt for 1 h. Under ice-bath cooling, to the solution was dropwise added 2N NaOH (40 m). The mixture was filtered. The filtrate was concentrated. The residue was purified by chromatography (heptane/ethyl acetate 4:1 (R$_f$=0.1) to heptane/ethyl acetate 0:1), giving the title compound as a colorless oil.

$^1$H NMR (300 Hz, CDCl$_3$) δ 4.58 (1H, br), 3.93-3.29 (m, 6H), 2.67-2.49 (m, 1H), 2.13-1.94 (m, 1H), 1.90-1.42 (m, 6H), 0.98-0.83 (m, 3H).

Preparation 16 (Compound 017)

[(2S)-2-Methyl-3-tetrahydropyran-2-yloxy-propyl] Methanesulfonate

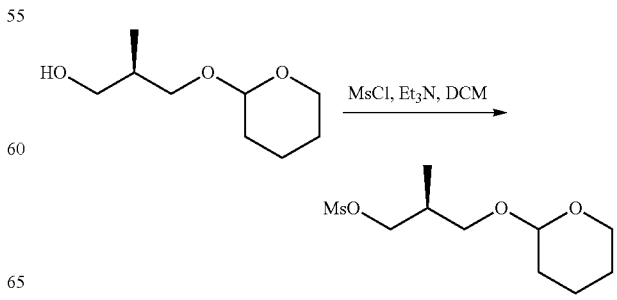

To a solution of (2R)-2-methyl-3-tetrahydropyran-2-yloxy-propan-1-ol (18 g, 103 mmol) and Et₃N (27.6 mL, 198 mmol) in DCM (100 mL) was dropwise added methanesulfonyl chloride (14.2 g, 124 mmol) at 0° C. The obtained mixture was stirred at rt for 0.5 h and washed with H₂, 1 N HCl and NaHCO₃ solution. The organic phase was dried over Na₂SO₄ and concentrated in vacuo, giving the title compound as brown syrup.

$^1$H NMR (300 MHz, CDCl₃) δ 4.62-4.50 (m, 1H), 4.35-4.09 (m, 2H), 3.83 (ddt, J=11.1, 7.4, 3.7 Hz, 1H), 3.73 (dd, J=9.8, 5.2 Hz, 0.5H), 3.67 (dd, J=9.9, 7.0 Hz, 0.5H), 3.56-3.46 (m, 1H), 3.37 (dd, J=9.8, 5.0 Hz, 0.5H), 3.30 (dd, J=9.8, 7.1 Hz, 0.5H), 3.01/3.01 (s, 3H), 2.31-2.10 (m, 1H), 1.93-1.45 (m, 6H), 1.04 (dd, J=6.9, 2.8 Hz, 3H).

Preparation 17 (Compound 018)

[(2R)-2-Methyl-3-tetrahydropyran-2-yloxy-propyl]hydrazine

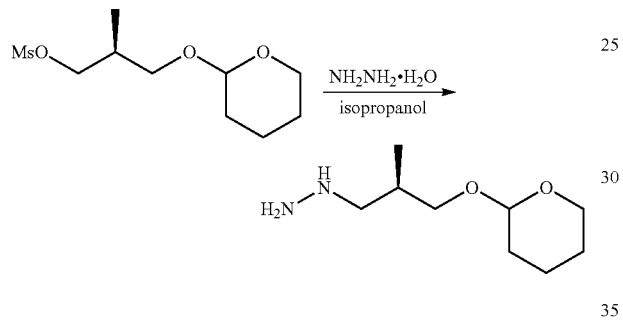

A solution of [(2S)-2-methyl-3-tetrahydropyran-2-yloxy-propyl] methanesulfonate (26 g, 103 mmol) and hydrazine monohydrate (30 mL) in isopropanol (100 mL) was heated to reflux for 2 h. The mixture was then concentrated in vacuo. The residue was taken up in DCM and washed with brine. The aqueous phase was extracted twice with DCM. The combined organic phases were dried over Na₂SO₄ and concentrated in vacuo, giving the title compound (crude). The crude was used directly in the next step without further purification.

Preparation 18 (Compound 019)

3-Ethyl-1-[(2R)-2-methyl-3-tetrahydropyran-2-yloxy-propyl]spiro[5,7-dihydroindazole-6,4'-tetrahydropyran]-4-one

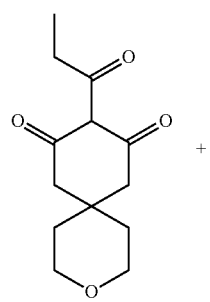

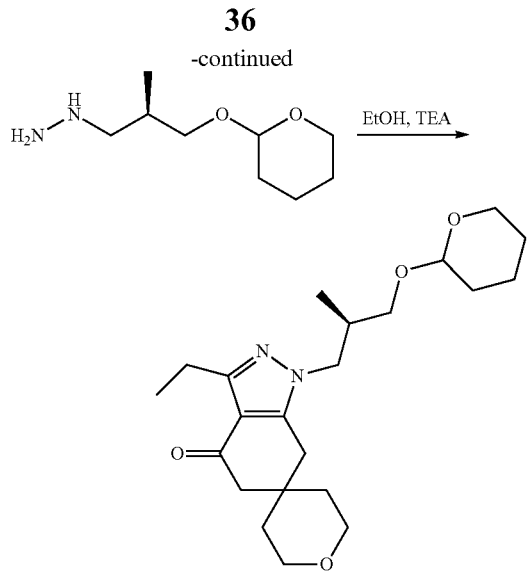

A solution of 9-propanoyl-3-oxaspiro[5.5]undecane-8,10-dione (15 g, 63 mmol) and [(2R)-2-methyl-3-tetrahydropyran-2-yloxy-propyl]hydrazine (15 g, 80 mmol) in isopropanol (100 mL) was heated reflux for 5 h. The solution was concentrated in vacuo. The residue was purified by chromatography (ethyl acetate, R$_f$=0.41), giving 25 g of product as an oil. The compound was used in the next step without characterization.

Preparation 19 (Compound 020)

3-Ethyl-1-[(2R)-3-hydroxy-2-methyl-propyl]spiro[5,7-dihydroindazole-6,4'-tetrahydropyran]-4-one

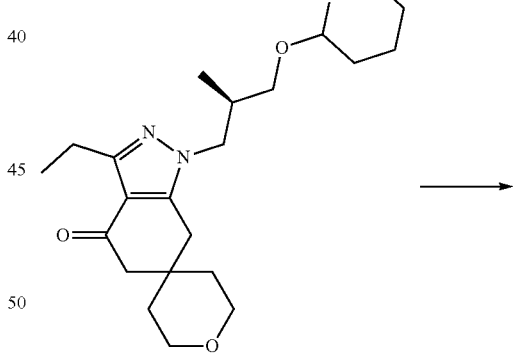

To a solution of 3-ethyl-1-[(2R)-2-methyl-3-tetrahydropyran-2-yloxy-propyl]spiro[5,7-dihydroindazole-6,4'-tetrahydropyran]-4-one (27 g, 69 mmol) in MeOH/H₂O (3:1, 200 mL) was added methanesulfonic acid (2 mL) at rt. The solution was stirred at 50° C. for 1 h and concentrated in vacuo in order to remove MeOH. The aqueous mixture was diluted with water and extracted three times with DCM. The combined organic phases were dried and concentrated in vacuo. The residue was purified by chromatography (ethyl acetate/MeOH 20:1), giving the title compound as an oil.

¹H NMR (300 MHz, DMSO-d₆) δ 4.63 (t, J=5.2 Hz, 1H), 4.05 (dd, J=13.7, 6.5 Hz, 1H), 3.81 (dd, J=13.7, 7.7 Hz, 1H), 3.68-3.50 (m, 4H), 3.37-3.15 (m, 2H), 2.95-2.82 (m, 2H), 2.80-2.65 (m, 2H), 2.41 (s, 2H), 2.15-2.00 (m, 1H), 1.53-1.39 (m, 4H), 1.13 (t, J=7.5 Hz, 3H), 0.80 (d, J=6.8 Hz, 3H).

Preparation 20 (Compound 021)

3-Ethyl-1-[(2R)-3-hydroxy-2-methyl-propyl]spiro[6,8-dihydro-5H-pyrazolo[4,3-c]azepine-7,4'-tetrahydropyran]-4-one

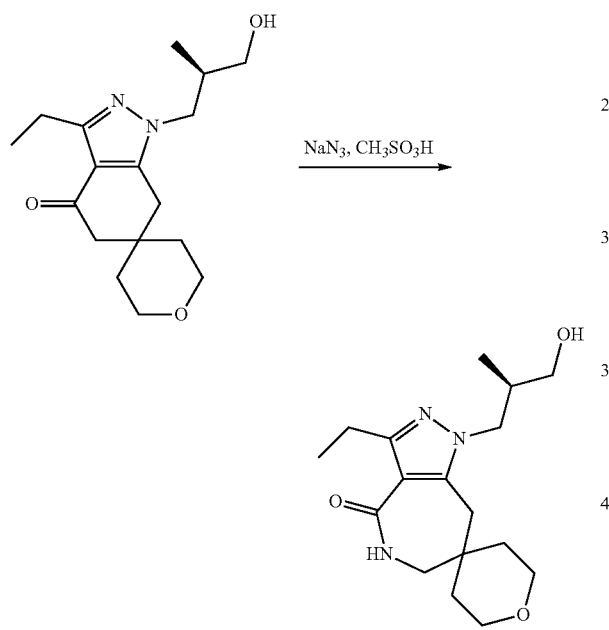

To a solution of 3-ethyl-1-[(2R)-3-hydroxy-2-methyl-propyl]spiro[5,7-dihydroindazole-6,4'-tetrahydropyran]-4-one (17 g, 55.5 mmol) in methanesulfonic acid (100 mL) was added sodium azide (7.2 g, 111 mmol) in portion at rt (exothermic). The obtained reaction mixture was stirred at rt for 2 h. Water (400 mL) was added to the mixture before it was neutralized with NaOH and concentrated. The residue was taken up in EtOH (400 mL). The precipitate was filtered off and washed with EtOH. The filtrate was concentrated in vacuo. The residue was taken up in DCM. The precipitate was filtered off and washed with DCM. The filtrate was concentrated in vacuo. The residue was purified twice by chromatography (DCM/MeOH 10:1), giving the title compound as colorless solid.

¹H NMR (600 MHz, DMSO-d₆) δ 7.41 (t, J=5.7 Hz, 1H), 4.64 (t, J=5.1 Hz, 1H), 4.00 (dd, J=13.9, 6.5 Hz, 1H), 3.73 (dd, J=13.9, 7.8 Hz, 1H), 3.69-3.60 (m, 2H), 3.58-3.50 (m, 2H), 3.30-3.20 (m, 2H), 3.01 (d, J=5.8 Hz, 2H), 2.81-2.79 (m, 4H), 2.16-2.01 (m, 1H), 1.50-1.40 (m, 4H), 1.11 (t, J=7.5 Hz, 3H), 0.81 (d, J=6.8 Hz, 3H).

HPLC-Retention time (XE Metode 7 CM): 1.67 minutes. Detected "M+1"-mass: 321.21.

Preparation 21 (Compound 022)

(3-Hydroxy-2,2-dimethyl-propyl) Benzoate

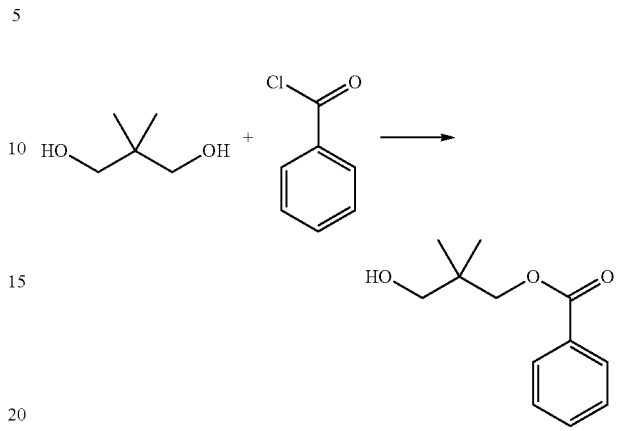

3-Hydroxy-2,2-dimethylpropanol (93.4 g, 900 mmol) was dissolved in DCM (600 mL), cooled in an ice bath under argon. DMAP (7.3 g, 60 mmol) and pyridine (48.3 mL, 600 mmol) was added, followed by dropwise addition of benzoyl chloride (34.9 mL, 300 mmol) over 15 min. The mixture was stirred at rt for 3 days and quenched with 4N HCl (90 mL). After phase separation, the organic phase was washed with sat. NaHCO₃ (50 mL), water (50 mL) and brine (50 mL), dried over MgSO₄, filtered and concentrated in vacuo. Column chromatography (10% EtOAc in heptane) afforded the title compound (47.7 g, 76% yield).

Preparation 22 (Compound 023)

(2,2-Dimethyl-3-oxo-propyl) Benzoate

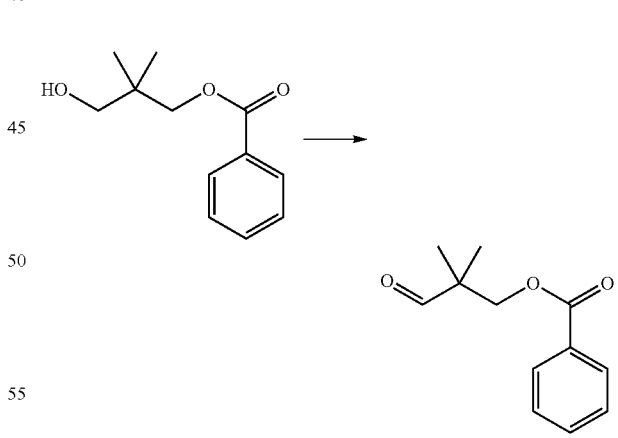

DMSO (17.9 mL, 251 mmol) in DCM (229 mL) was cooled to −70° C. in a 2 necked bottle equipped with thermometer, addition funnel and argon flow. Oxalyl chloride (25.5 mL, 297 mmol) in DCM (114 mL) was added slowly while maintaining temperature between −60 to −70° C. The mixture was stirred at −70° C. for 0.5 hour before (3-hydroxy-2,2-dimethyl-propyl) benzoate (47.6 g, 229 mmol) in DCM (229 mL) was added slowly while maintaining temperature between −60 and −70° C. The reaction mixture was stirred at −70° C. for 0.5 h. Triethylamine (127 mL, 914 mmol) was added slowly while maintaining temperature between −60 and −70° C. The mixture was stirred for 2 hours. Water (100 mL) was added and the mixture was phase separated. The aqueous phase was extracted with three times with DCM (3×50 mL) and the combined organic phases were washed with water (50 mL), brine (50 mL), dried over MgSO₄ and filtered. Evaporation to dryness afforded approx. 60 g of reddish oil with precipitation. This mixture was suspended in DCM (20 mL) and filtered. Column chromatography (10 to 35% EtOAc in heptane) afforded the title compound.

$^1$H NMR (300 MHz, CDCl$_3$) δ 9.64 (s, 1H), 8.22-7.79 (m, 2H), 7.64-7.50 (m, 1H), 7.50-7.35 (m, 2H), 4.37 (s, 2H), 1.21 (s, 6H).

Preparation 23 (Compound 024)

[3-(2-Tert-butoxycarbonylhydrazino)-2,2-dimethyl-propyl] Benzoate

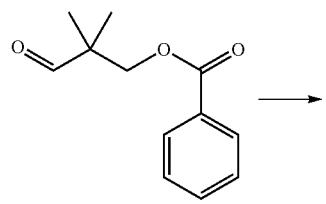

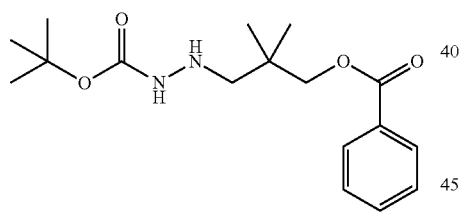

BOC—NHNH$_2$ (21.8 g, 165 mmol) and AcOH (28.3 mL, 495 mmol) was added to a solution of (2,2-dimethyl-3-oxo-propyl) benzoate (34.0 g, 165 mmol) in MeOH (200 mL). The reaction mixture was stirred at rt for 30 minutes before it was cooled to 0° C. Sodium cyanoborohydride (15.5 g, 247 mmol) was added portion wise over 5 minutes and the mixture was stirred for an additional 45 minutes at 0° C. The reaction was quenched with water (100 mL), and the mixture was extracted twice with DCM (2×200 mL). The combined organic phases were washed with water (100 mL), dried over MgSO$_4$, filtered and concentrated in vacuo. Column chromatography (heptane/ethyl acetate 9:1 to 1:1) afforded the title compound (37.7 g, 71% yield) as an oil.

$^1$H NMR (300 MHz, CDCl$_3$) δ 8.20-7.99 (m, 2H), 7.63-7.50 (m, 1H), 7.50-7.37 (m, 2H), 6.13 (s, 1H), 4.23-4.15 (m, 1H), 4.14 (s, 2H), 2.86 (s, 2H), 1.42 (s, 9H), 1.04 (s, 6H).

Preparation 24 (Compound 025)

(3-Hydrazino-2,2-dimethyl-propyl) Benzoate Ditrifluoroacetic Acid Salt

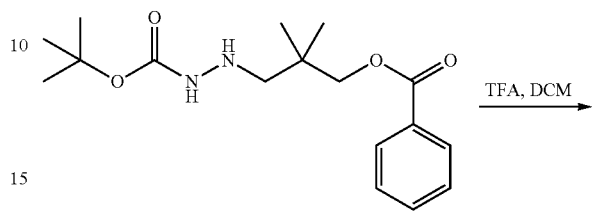

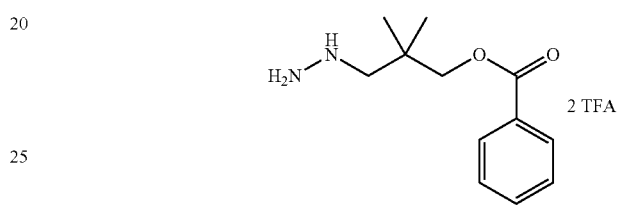

[3-(2-Tert-butoxycarbonylhydrazino)-2,2-dimethyl-propyl] benzoate (40 g, 124 mmol) was dissolved in DCM. TFA (50 mL) was added and the obtained solution was stirred at rt for 1 hour. Concentrated in vacuo gave the title compound (27.6 g, quantitative yield).

$^1$H NMR (300 MHz, CDCl$_3$) δ 8.03-7.96 (m, 2H), 7.64-7.53 (m, 1H), 7.50-7.40 (m, 2H), 4.20 (s, 2H), 3.09 (s, 2H), 1.16 (s, 6H).

Preparation 25 (Compound 026)

[3-(3-Ethyl-4-oxo-spiro[5,7-dihydroindazole-6,4'-tetrahydropyran]-1-yl)-2,2-dimethyl-propyl] Benzoate

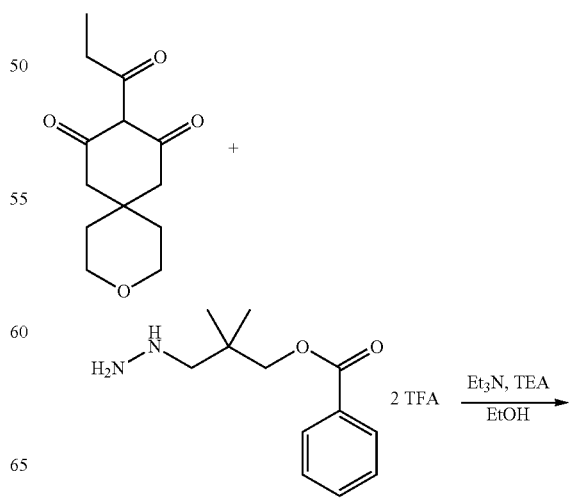

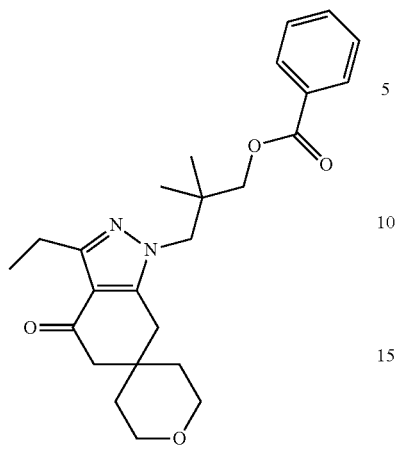

A mixture of 9-propanoyl-3-oxaspiro[5.5]undecane-8,10-dione (15 g, 63.0 mmol), (3-hydrazino-2,2-dimethyl-propyl)benzoate.2TFA (33.6 g, 74.6 mmol) and Et₃N (35 mL, 252 mmol) in ethanol (200 mL) was stirred at rt for 10 minutes before it was heated to reflux for 2 hours. The mixture was then concentrated in vacuo. Water (100 mL) was added and the aqueous mixture was extracted three times with DCM (3×100 mL). The combined organic phases were dried over MgSO₄, filtered and concentrated in vacuo. Chromatography (heptane/ethyl acetate 9:1 to 1:9) gave the title product (15.8 g, 59% yield) as an oil.

¹H NMR (300 MHz, CDCl₃) δ: 8.07-8.00 (m, 2H), 7.63-7.56 (m, 1H), 7.50-7.43 (m, 2H), 4.13 (s, 2H), 4.00 (s, 2H), 3.73-3.53 (m, 4H), 2.83 (q, J=7.5 Hz, 2H), 2.68 (s, 2H), 2.46 (s, 2H), 1.66-1.52 (m, 3H), 1.52-1.40 (m, 2H), 1.22 (t, J=7.5 Hz, 3H), 1.13 (s, 6H).

Preparation 26 (Compound 027)

[3-(3-Ethyl-4-oxo-spiro[6,8-dihydro-5H-pyrazolo[4,3-c]azepine-7,4'-tetrahydropyran]-1-yl)-2,2-dimethyl-propyl] Benzoate

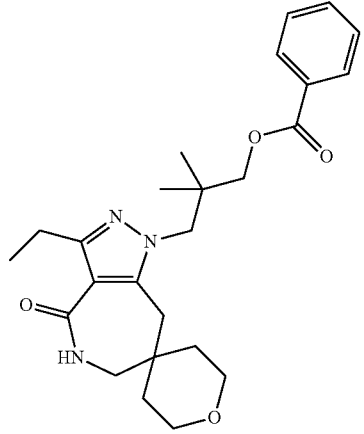

To a solution of [3-(3-ethyl-4-oxo-spiro[5,7-dihydroindazole-6,4'-tetrahydropyran]-1-yl)-2,2-dimethyl-propyl] benzoate (15 g, 35.3 mmol) in methanesulfonic acid (30 mL) and DCM (50 mL) was added sodium azide (11.5 g, 176.7 mmol) in portions at rt over 1 hour. Then the mixture was stirred at rt for 2 hours. The reaction was not complete. Ethanol (500 mL) was added to the mixture before it was neutralized with solid sodium hydroxide. The solid material was filtered off. The filtrate was concentrated in vacuo. The residue was taken up in chloroform (100 mL). The mixture was left standing for 30 minutes. The solid material was filtered off again. The filtrate was concentrated in vacuo. The residue was purified three times by chromatography (CHCl₃/MeOH 10:1, R$_f$=0.17), giving the title compound (7.0 g, 45% yield) as a solid.

¹H NMR (600 MHz, DMSO-d6) δ 7.98 (t, J=7.7 Hz, 2H), 7.67 (t, J=7.7 Hz, 1H), 7.54 (t, J=7.7 Hz, 2H), 7.42 (t, J=5.7 Hz, 1H), 4.10 (s, 2H), 4.01 (s, 2H), 3.60-3.55 (m, 2H), 3.52-3.45 (m, 2H), 2.97 (d, J=5.7 Hz, 2H), 2.75 (s, 2H), 2.71 (q, J=7.5 Hz, 2H), 1.37 (t, J=5.4 Hz, 4H), 1.09 (t, J=7.5 Hz, 3H), 1.04 (s, 6H).

HPLC-Retention time (XE Metode 7 CM): 2.25 minutes. Detected "M+1"-mass: 440.25.

Preparation 27 (Compound 028)

3-Ethyl-1-(3-hydroxy-2,2-dimethyl-propyl)spiro[6,8-dihydro-5H-pyrazolo[4,3-c]azepine-7,4'-tetrahydropyran]-4-one

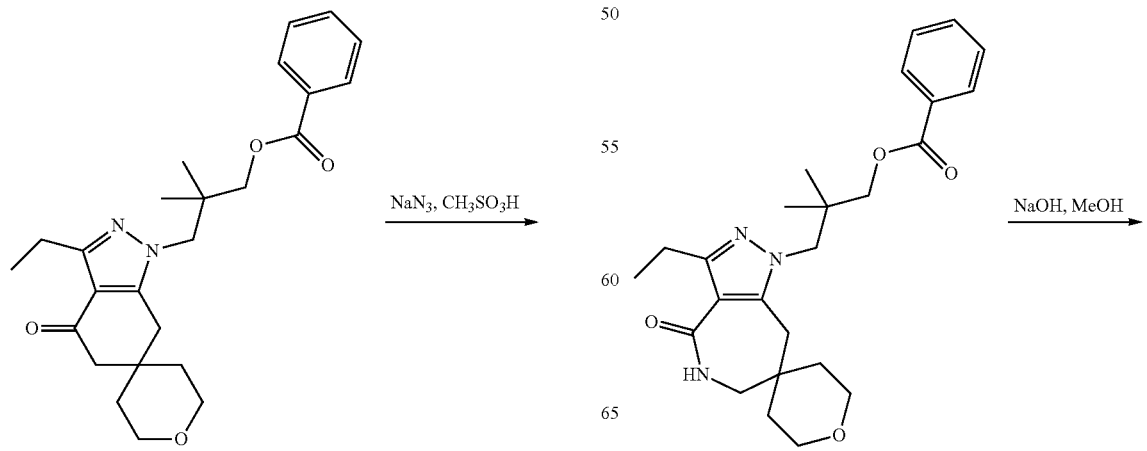

43
-continued

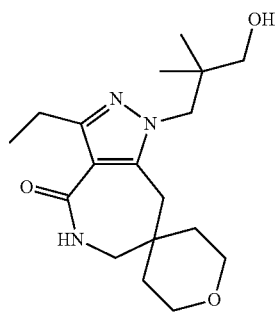

To a mixture of [3-(3-ethyl-4-oxo-spiro[6,8-dihydro-5H-pyrazolo[4,3-c]azepine-7,4'-tetrahydropyran]-1-yl)-2,2-dimethyl-propyl] benzoate (7.0 g, 15.9 mmol) in MeOH (50 mL) was added NaOH (1 g) at rt. The mixture was stirred at 50° C. for 0.5 h until starting material disappeared. Then the solution was neutralized by using 4N HCl and concentrated in vacuo. The residue was taken up in EtOH. The insoluble was filtered off. The filtrate was concentrated in vacuo. The residue was purified by chromatography (MeOH/DCM 1:10, $R_f$=0.36). Recrystallized in TBME/heptane gave the title compound (5.06 g, 95% yield) as colorless crystals.

$^1$H NMR (300 MHz, DMSO-d6) δ 7.40 (t, J=5.7 Hz, 1H), 4.75 (t, J=5.3 Hz, 1H), 3.82 (s, 2H), 3.74-3.45 (m, 4H), 3.13 (d, J=5.2 Hz, 2H), 2.99 (d, J=5.6 Hz, 2H), 2.79 (s, 2H), 2.72 (d, J=7.5 Hz, 2H), 1.50-1.35 (m, 4H), 1.11 (t, J=7.5 Hz, 3H), 0.83 (s, 6H).

HPLC-Retention time (XE Metode 7 CM): 1.78 minutes.

Detected "M+1"-mass: 336.22.

Preparation 28 (Compound 029)

4-Hydrazinobutan-1-ol

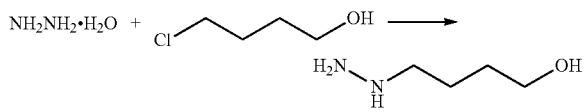

To hydrazine monohydrate (20 mL) was added 4-chlorobutanol (10.8 g, 99.5 mmol) at 0° C. The solution was stirred at rt for 2 days. To the solution was added NaOH (4 g, 99.5 mmol). The mixture was stirred for 1 hour and concentrated in vacuo. The residue was taken up in isopropanol (50 mL). The precipitate was filtered off over celite. The filtrate was concentrated in vacuo, giving an oil (5.5 g), which was used without further purification.

44

Preparation 29 (Compound 030)

3-Ethyl-1-(4-hydroxybutyl)spiro[5,7-dihydroindazole-6,4'-tetrahydropyran]-4-one

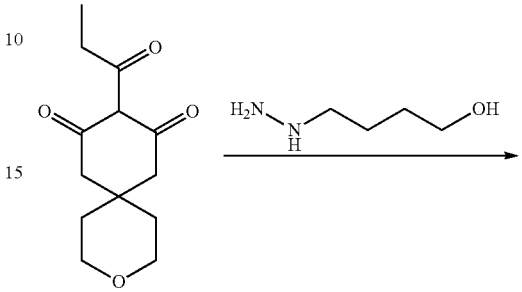

A mixture of 9-propanoyl-3-oxaspiro[5.5]undecane-8,10-dione (1.2 g, 5.0 mmol), 4-hydrazinobutan-1-ol (0.8 g, 8 mmol) and triethylamine (2 mL) in EtOH (20 mL) was heated to 100° C. for 1 hour. The solution was concentrated in vacuo. Column chromatography (ethyl acetate/MeOH 9:1, $R_f$=0.2), gave the title compound as an orange oil (1.09 g, 71% yield).

$^1$H NMR (300 MHz, CDCl$_3$) δ 4.07 (t, J=7.0 Hz, 2H), 3.78-3.59 (m, 6H), 2.85 (q, J=7.5 Hz, 2H), 2.75 (s, 2H), 2.52 (s, 2H), 2.01-1.86 (m, 2H), 1.75-1.45 (m, 7H), Preparation 30 (Compound 031)

3-Ethyl-1-(4-hydroxybutyl)spiro[6,8-dihydro-5H-pyrazolo[4,3-c]azepine-7,4'-tetrahydropyran]-4-one

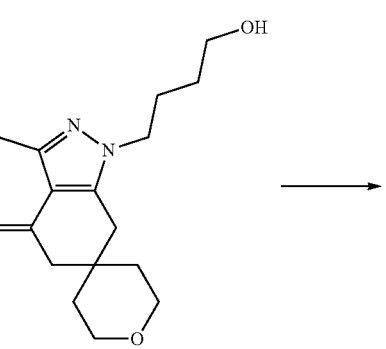

-continued

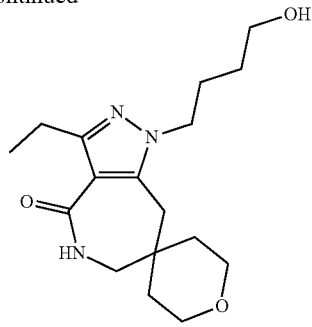

To a mixture of 3-ethyl-1-(4-hydroxybutyl)spiro[5,7-dihydroindazole-6,4'-tetrahydropyran]-4-one (1.09 g, 3.56 mmol) and sodium azide (1.2 g, 18 mmol) in CHCl₃ (5 mL) was added methanesulfonic acid (3.4 g, 35.6 mmol). The obtained mixture was stirred at rt overnight. The mixture was then diluted with water and neutralized by addition of NaOH. The mixture was extracted three times with ethyl acetate. The combined organic phases were dried and concentrated in vacuo. Column chromatography (ethyl acetate/ MeOH10:1) afforded the title compound (319 mg, 28% yield) as an oil.

$^1$H NMR (DMSO-d6) δ: 7.39 (t, J=5.7 Hz, 1H), 4.43 (t, J=5.1 Hz, 1H), 3.96 (t, J=7.3 Hz, 2H), 3.69-3.60 (m, 2H), 3.60-3.49 (m, 2H), 3.43-3.36 (m, 2H), 3.01 (d, J=5.7 Hz, 2H), 2.77-2.67 (m, 4H), 1.80-1.66 (m, 2H), 1.51-1.35 (m, 6H), 1.10 (t, J=7.5 Hz, 3H).

HPLC-Retention time (XE Metode 7 CM): 1.63 minutes. Detected "M+1"-mass: 322.21.

General Procedure 1: Esterification

To a solution of an acid (2 equiv) in DMF (0.1 mL) were added a solution of an alcohol (0.013 mmol) in DMF (0.1 mL) and a solution of DMAP (2 equiv) in DMF (0.1 ML). To this resulting solution was added a suspension of EDAC (2.7 equiv) in DMF (0.1 mL). The mixture was shaken at 50° C. overnight. The crude was subjected to preparative LCMS purification, giving an ester.

General Procedure 2: Esterification

An alcohol (0.013 mmol) was dissolved in DCE (0.15 mL). A solution of an acid (2 equiv) in DCE (0.2 mL) and a solution of DMAP (1 equiv) in DCE (0.1 mL) were added. To the resulting mixture was added EDAC (2 equiv). The mixture was then shaken at 50° C. overnight and concentrated in vacuo. The residue was redissolved in DMF (0.3 mL) and subjected to preparative LCMS purification, giving an ester.

PDE4 Assay

The human PDE4D catalytic domain (UniProt no. Q08499 [S380-L740]) was incubated with a mixture of non-labelled cAMP (cyclic adenosine monophosphate) and fluorescein amidite (FAM) conjugated cAMP and titrated test or reference compound. Following brief incubation the enzymatic reaction was stopped by addition of binding buffer containing nanoparticles with immobilized trivalent metal ions capable of binding 1) AMP phospho groups and 2) terbium (Tb) donor fluorophores. Subsequent excitation of the Tb donor triggers time-resolved FRET to adjacent FAM acceptor molecules resulting in light emission. In the presence of a PDE4 inhibitor, AMP generation was reduced resulting in a lower fluorescence signal. The cAMP phosphodiester is not bound by the detection system.

The results were calculated as the molar concentrations resulting in 50% inhibition of the substrate cleavage compared to controls samples, and are expressed as a range of $IC_{50}$ (nM).

PDE4 $IC_{50}$ ranges
* indicates that $IC_{50}$ values are >500 nM
** indicates that $IC_{50}$ values are >100 and <500 nM
*** indicates that $IC_{50}$ values are <100 nM The Examples 1-16 shown in Table 1 were prepared by reacting Compound 009 as described in General Procedure 1 with the appropriate acid:

TABLE 1

| Ex. | Cmpd | Structure | IUPAC Name | HPLC Rt (min) | PDE4 Potency Range |
|---|---|---|---|---|---|
| 1 | 100 | 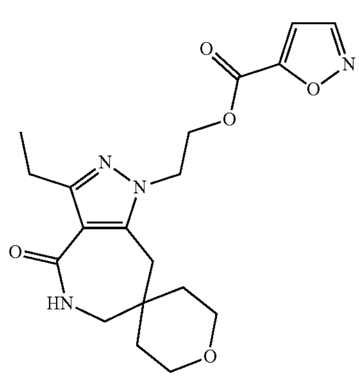 [SMILES: CCc1nn(CCOC(=O)c2ccno2)c2c1C(=O)NCC1(CCOCC1)C2] | 2-(3-ethyl-4-oxo-spiro[6,8-dihydro-5H-pyrazolo[4,3-c]azepine-7,4'-tetrahydropyran]-1-yl)ethyl isoxazole-5-carboxylate | 1.78 | ** |

TABLE 1-continued

| Ex. | Cmpd | Structure | IUPAC Name | HPLC Rt (min) | PDE4 Potency Range |
|---|---|---|---|---|---|
| 2 | 101 | 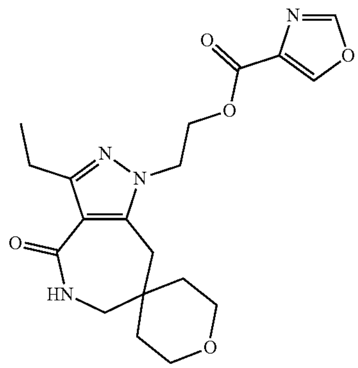 [SMILES: CCc1nn(CCOC(=O)c2cocn2)c2c1C(=O)NCC1(CCOCC1)C2] | 2-(3-ethyl-4-oxo-spiro[6,8-dihydro-5H-pyrazolo[4,3-c]azepine-7,4'-tetrahydropyran]-1-yl)ethyl oxazole-4-carboxylate | 1.68 | * |
| 3 | 102 | 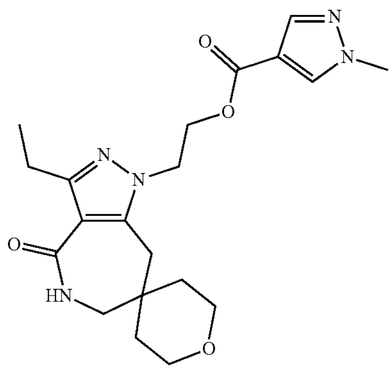 [SMILES: CCc1nn(CCOC(=O)c2cnn(C)c2)c2c1C(=O)NCC1(CCOCC1)C2] | 2-(3-ethyl-4-oxo-spiro[6,8-dihydro-5H-pyrazolo[4,3-c]azepine-7,4'-tetrahydropyran]-1-yl)ethyl 1-methylpyrazole-4-carboxylate | 1.71 | * |
| 4 | 103 | 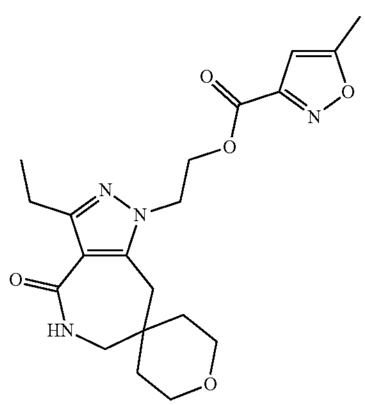 [SMILES: CCc1nn(CCOC(=O)c2cc(C)on2)c2c1C(=O)NCC1(CCOCC1)C2] | 2-(3-ethyl-4-oxo-spiro[6,8-dihydro-5H-pyrazolo[4,3-c]azepine-7,4'-tetrahydropyran]-1-yl)ethyl 5-methylisoxazole-3-carboxylate | 1.85 | ** |
| 5 | 104 | 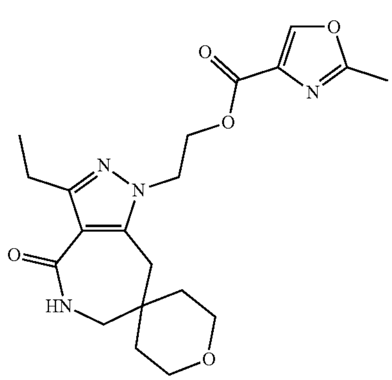 [SMILES: CCc1nn(CCOC(=O)c2coc(C)n2)c2c1C(=O)NCC1(CCOCC1)C2] | 2-(3-ethyl-4-oxo-spiro[6,8-dihydro-5H-pyrazolo[4,3-c]azepine-7,4'-tetrahydropyran]-1-yl)ethyl 2-methyloxazole-4-carboxylate | 1.73 | * |

TABLE 1-continued

| Ex. | Cmpd | Structure | IUPAC Name | HPLC Rt (min) | PDE4 Potency Range |
|---|---|---|---|---|---|
| 6 | 105 | 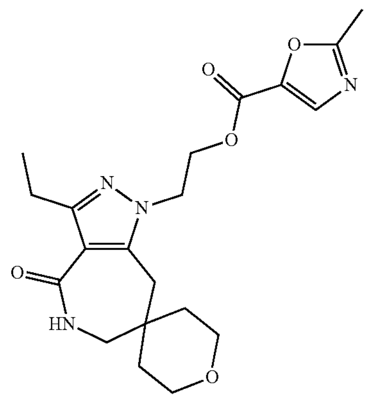 [SMILES: CCc1nn(CCOC(=O)c2cnc(C)o2)c2c1C(=O)NCC1(CCOCC1)C2] | 2-(3-ethyl-4-oxo-spiro[6,8-dihydro-5H-pyrazolo[4,3-c]azepine-7,4'-tetrahydropyran]-1-yl)ethyl 2-methyloxazole-5-carboxylate | 1.74 | * |
| 7 | 106 | 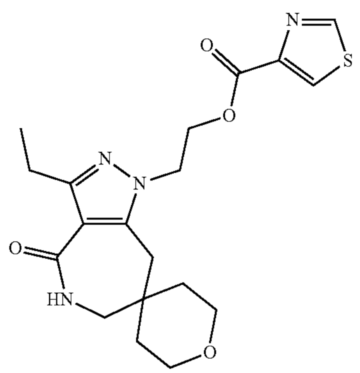 [SMILES: CCc1nn(CCOC(=O)c2cscn2)c2c1C(=O)NCC1(CCOCC1)C2] | 2-(3-ethyl-4-oxo-spiro[6,8-dihydro-5H-pyrazolo[4,3-c]azepine-7,4'-tetrahydropyran]-1-yl)ethyl thiazole-4-carboxylate | 1.71 | * |
| 8 | 107 | 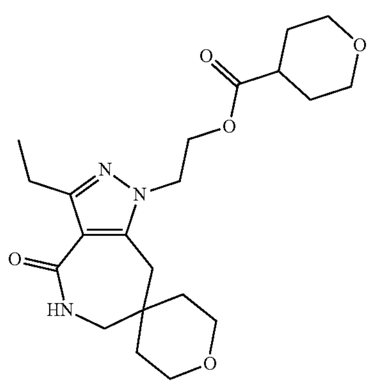 [SMILES: CCc1nn(CCOC(=O)C2CCOCC2)c2c1C(=O)NCC1(CCOCC1)C2] | 2-(3-ethyl-4-oxo-spiro[6,8-dihydro-5H-pyrazolo[4,3-c]azepine-7,4'-tetrahydropyran]-1-yl)ethyl tetrahydropyran-4-carboxylate | 1.77 | * |
| 9 | 108 | 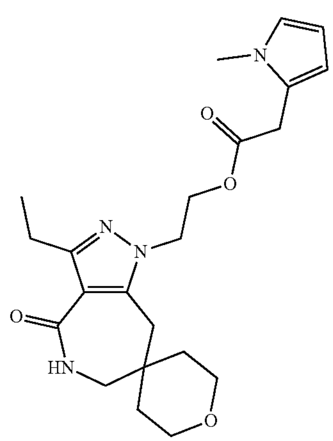 [SMILES: CCc1nn(CCOC(=O)Cc2cccn2C)c2c1C(=O)NCC1(CCOCC1)C2] | 2-(3-ethyl-4-oxo-spiro[6,8-dihydro-5H-pyrazolo[4,3-c]azepine-7,4'-tetrahydropyran]-1-yl)ethyl 2-(1-methylpyrrol-2-yl)acetate | 1.91 | * |

TABLE 1-continued

| Ex. | Cmpd | Structure | IUPAC Name | HPLC Rt (min) | PDE4 Potency Range |
|---|---|---|---|---|---|
| 10 | 109 | 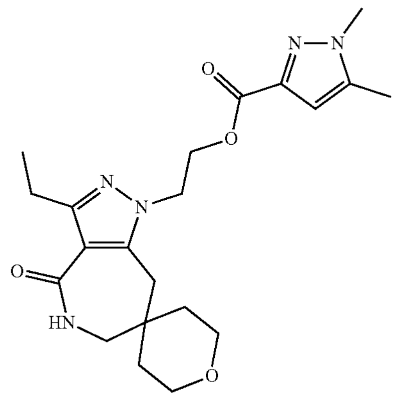 [SMILES: CCc1nn(CCOC(=O)c2cc(C)n(C)n2)c2c1C(=O)NCC1(CCOCC1)C2] | 2-(3-ethyl-4-oxo-spiro[6,8-dihydro-5H-pyrazolo[4,3-c]azepine-7,4'-tetrahydropyran]-1-yl)ethyl 1,5-dimethylpyrazole-3-carboxylate | 1.77 | * |
| 11 | 110 | 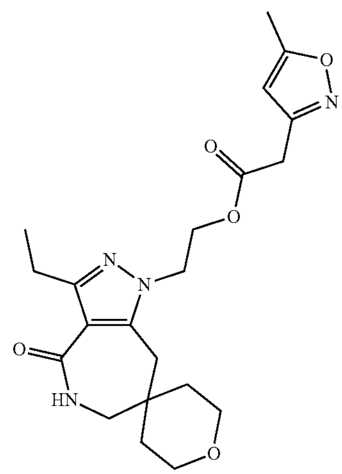 [SMILES: CCc1nn(CCOC(=O)Cc2cc(C)on2)c2c1C(=O)NCC1(CCOCC1)C2] | 2-(3-ethyl-4-oxo-spiro[6,8-dihydro-5H-pyrazolo[4,3-c]azepine-7,4'-tetrahydropyran]-1-yl)ethyl 2-(5-methylisoxazol-3-yl)acetate | 1.82 | * |
| 12 | 111 | 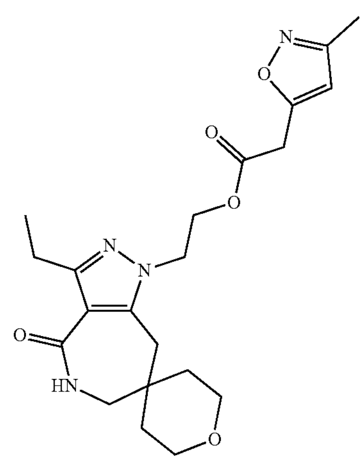 [SMILES: CCc1nn(CCOC(=O)Cc2cc(C)no2)c2c1C(=O)NCC1(CCOCC1)C2] | 2-(3-ethyl-4-oxo-spiro[6,8-dihydro-5H-pyrazolo[4,3-c]azepine-7,4'-tetrahydropyran]-1-yl)ethyl 2-(3-methylisoxazol-5-yl)acetate | 1.80 | * |

TABLE 1-continued

| Ex. | Cmpd | Structure | IUPAC Name | HPLC Rt (min) | PDE4 Potency Range |
|---|---|---|---|---|---|
| 13 | 112 | 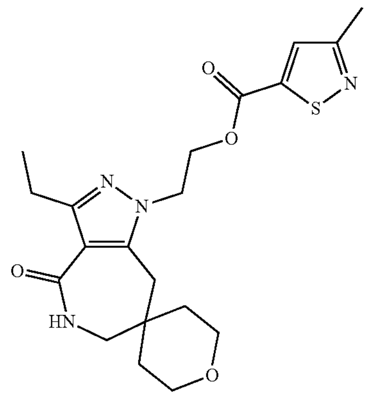 [SMILES: CCc1nn(CCOC(=O)c2cc(C)ns2)c2c1C(=O)NCC1(CCOCC1)C2] | 2-(3-ethyl-4-oxo-spiro[6,8-dihydro-5H-pyrazolo[4,3-c]azepine-7,4'-tetrahydropyran]-1-yl)ethyl 3-methylisothiazole-5-carboxylate | 1.90 | ** |
| 14 | 113 | 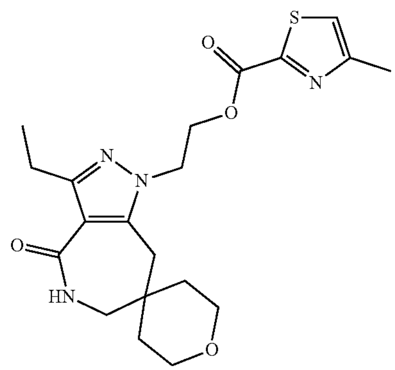 [SMILES: CCc1nn(CCOC(=O)c2nc(C)cs2)c2c1C(=O)NCC1(CCOCC1)C2] | 2-(3-ethyl-4-oxo-spiro[6,8-dihydro-5H-pyrazolo[4,3-c]azepine-7,4'-tetrahydropyran]-1-yl)ethyl 4-methylthiazole-2-carboxylate | 1.82 | ** |
| 15 | 114 | 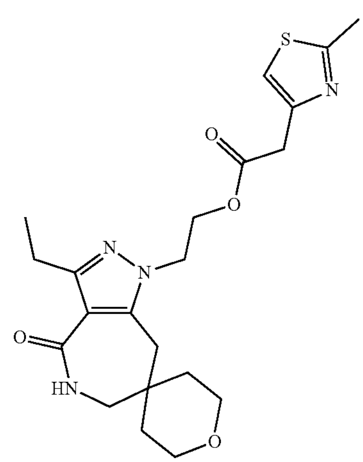 [SMILES: CCc1nn(CCOC(=O)Cc2csc(C)n2)c2c1C(=O)NCC1(CCOCC1)C2] | 2-(3-ethyl-4-oxo-spiro[6,8-dihydro-5H-pyrazolo[4,3-c]azepine-7,4'-tetrahydropyran]-1-yl)ethyl 2-(2-methylthiazol-4-yl)acetate | 1.79 | * |

TABLE 1-continued

| Ex. | Cmpd | Structure | IUPAC Name | HPLC Rt (min) | PDE4 Potency Range |
|---|---|---|---|---|---|
| 16 | 115 | 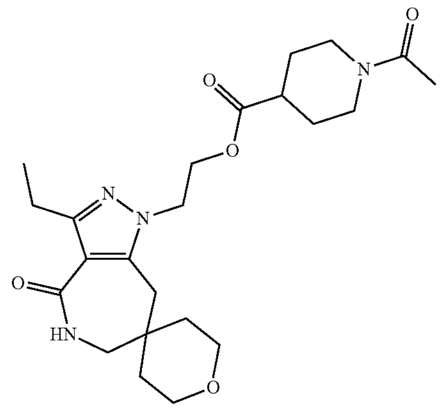 [SMILES: CCc1nn(CCOC(=O)C2CCN(C(C)=O)CC2)c2c1C(=O)NCC1(CCOCC1)C2] | 2-(3-ethyl-4-oxo-spiro[6,8-dihydro-5H-pyrazolo[4,3-c]azepine-7,4'-tetrahydropyran]-1-yl)ethyl 1-acetylpiperidine-4-carboxylate | 1.70 | * |

The Examples 17-107 shown in Table 2 were prepared by reacting Compound 014 as described in General Procedure 1 with the appropriate acid:

TABLE 2

| Ex. | Cmpd | Structure | IUPAC Name | HPLC Rt (min) | PDE4 Potency Range |
|---|---|---|---|---|---|
| 17 | 116 | 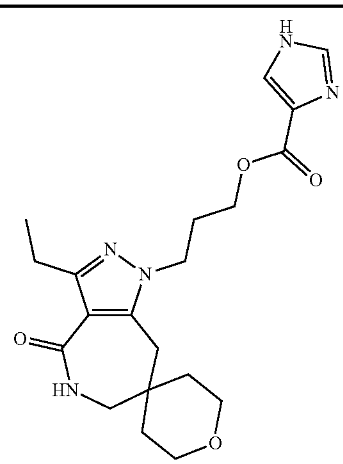 | 3-(3-ethyl-4-oxo-spiro[6,8-dihydro-5H-pyrazolo[4,3-c]azepine-7,4'-tetrahydropyran]-1-yl)propyl 1H-imidazole-4-carboxylate | 1.62 | * |
| 18 | 117 | 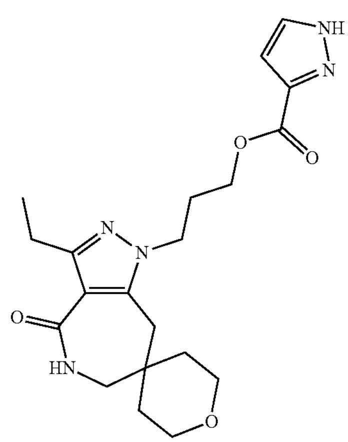 [SMILES: CCc1nn(CCCOC(=O)c2cc[nH]n2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 1H-pyrazole-3-carboxylate | 1.73 | ** |

TABLE 2-continued

| Ex. | Cmpd | Structure | IUPAC Name | HPLC Rt (min) | PDE4 Potency Range |
|---|---|---|---|---|---|
| 19 | 118 | 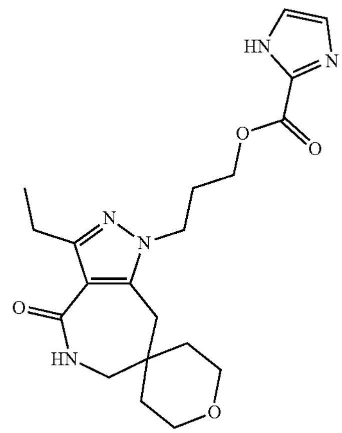 [SMILES: CCc1nn(CCCOC(=O)c2ncc[nH]2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 1H-imidazole-2-carboxylate | 1.64 | * |
| 20 | 119 | 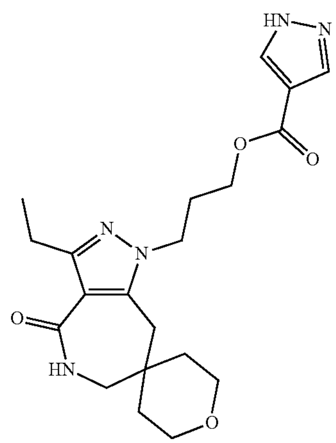 [SMILES: CCc1nn(CCCOC(=O)c2cn[nH]c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 1H-pyrazole-4-carboxylate | 1.71 | ** |
| 21 | 120 | 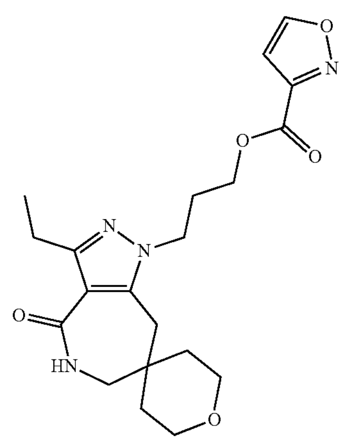 [SMILES: CCc1nn(CCCOC(=O)c2ccon2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl isoxazole-3-carboxylate | 1.83 | * |

TABLE 2-continued

| Ex. | Cmpd | Structure | IUPAC Name | HPLC Rt (min) | PDE4 Potency Range |
|---|---|---|---|---|---|
| 22 | 121 | 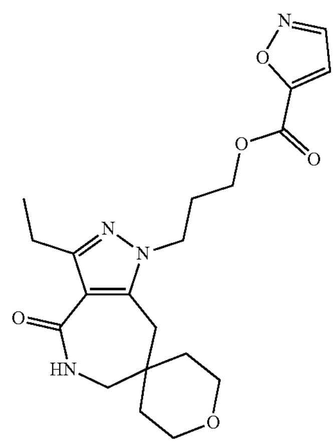 [SMILES: CCc1nn(CCCOC(=O)c2ccno2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl isoxazole-5-carboxylate | 1.84 | ** |
| 23 | 122 | 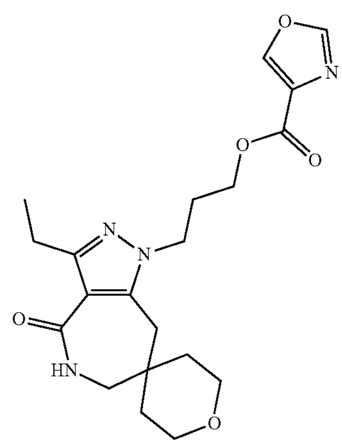 [SMILES: CCc1nn(CCCOC(=O)c2cocn2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl oxazole-4-carboxylate | 1.73 | * |
| 24 | 123 | 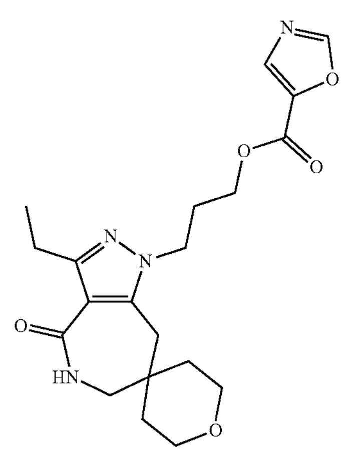 [SMILES: CCc1nn(CCCOC(=O)c2cnco2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl oxazole-5-carboxylate | 1.76 | * |

TABLE 2-continued

| Ex. | Cmpd | Structure | IUPAC Name | HPLC Rt (min) | PDE4 Potency Range |
|---|---|---|---|---|---|
| 25 | 124 | 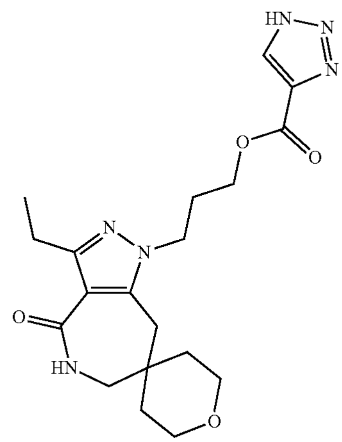 [SMILES: CCc1nn(CCCOC(=O)c2c[nH]nn2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 1H-triazole-4-carboxylate | 1.68 | ** |
| 26 | 125 | 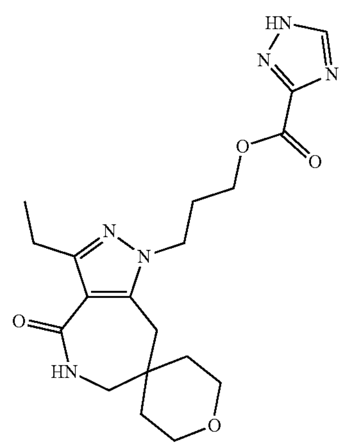 [SMILES: CCc1nn(CCCOC(=O)c2nc[nH]n2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 1H-1,2,4-triazole-3-carboxylate | 1.62 | * |
| 27 | 126 | 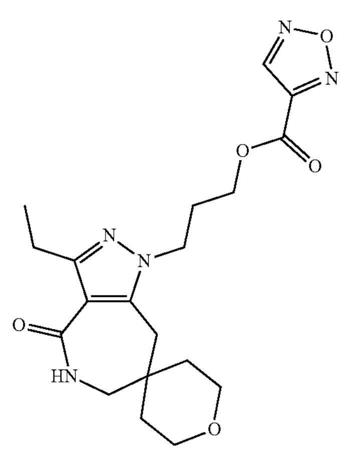 [SMILES: CCc1nn(CCCOC(=O)c2cnon2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 1,2,5-oxadiazole-3-carboxylate | 1.83 | ** |

TABLE 2-continued

| Ex. | Cmpd | Structure | IUPAC Name | HPLC Rt (min) | PDE4 Potency Range |
|---|---|---|---|---|---|
| 28 | 127 | 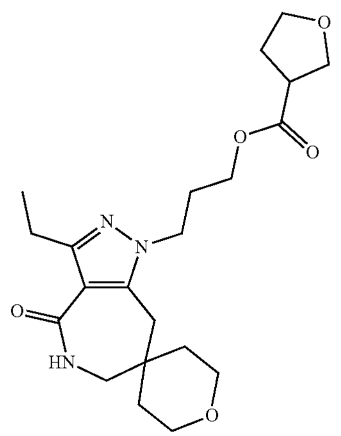 [SMILES: CCc1nn(CCCOC(=O)C2CCOC2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl tetrahydrofuran-3-carboxylate | 1.79 | * |
| 29 | 128 | 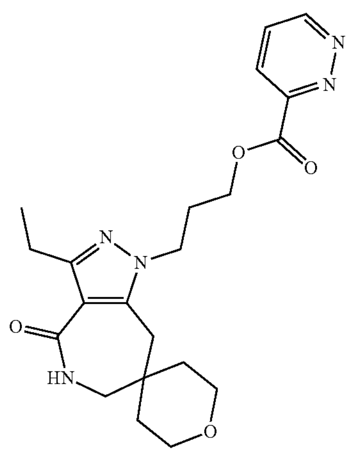 [SMILES: CCc1nn(CCCOC(=O)c2cccnn2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl pyridazine-3-carboxylate | 1.68 | * |
| 30 | 129 | 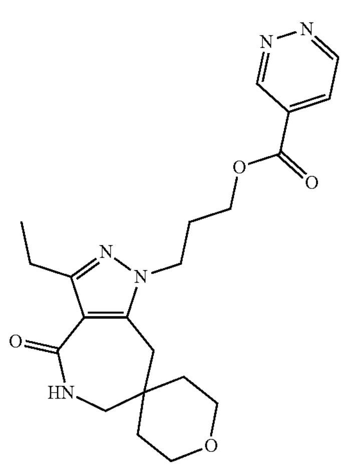 [SMILES: CCc1nn(CCCOC(=O)c2ccnnc2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl pyridazine-4-carboxylate | 1.71 | * |

TABLE 2-continued

| Ex. | Cmpd | Structure | IUPAC Name | HPLC Rt (min) | PDE4 Potency Range |
|---|---|---|---|---|---|
| 31 | 130 | 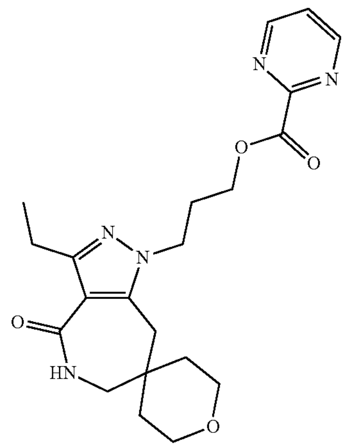 [SMILES: CCc1nn(CCCOC(=O)c2ncccn2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl pyrimidine-2-carboxylate | 1.66 | * |
| 32 | 131 | 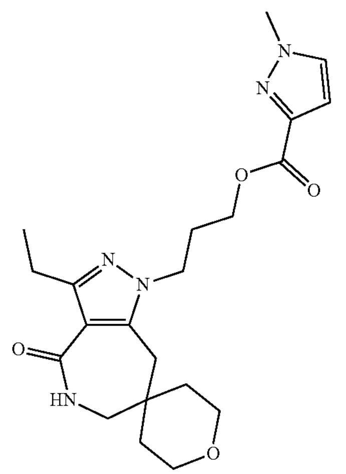 [SMILES: CCc1nn(CCCOC(=O)c2ccn(C)n2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 1-methylpyrazole-3-carboxylate | 1.76 | * |
| 33 | 132 | 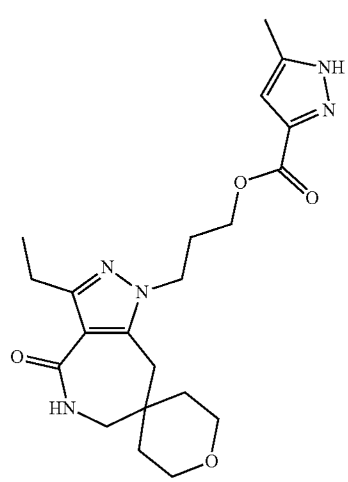 [SMILES: CCc1nn(CCCOC(=O)c2cc(C)[nH]n2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 5-methyl-1H-pyrazole-3-carboxylate | 1.77 | ** |

TABLE 2-continued

| Ex. | Cmpd | Structure | IUPAC Name | HPLC Rt (min) | PDE4 Potency Range |
|---|---|---|---|---|---|
| 34 | 133 | 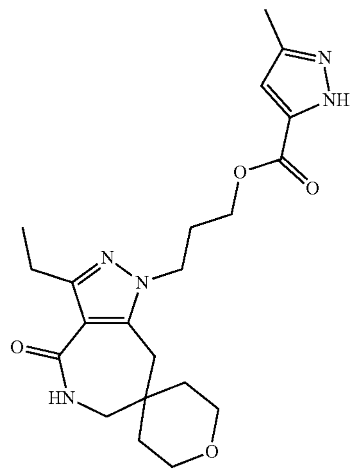 [SMILES: CCc1nn(CCCOC(=O)c2cc(C)n[nH]2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-methyl-1H-pyrazole-5-carboxylate | 1.77 | ** |
| 35 | 134 | 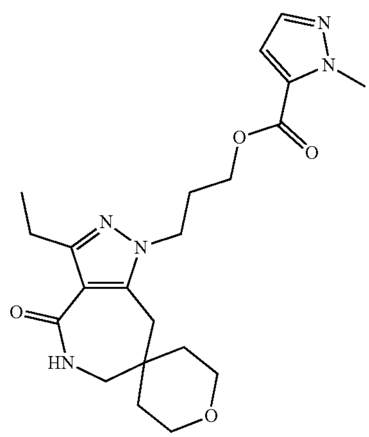 [SMILES: CCc1nn(CCCOC(=O)c2ccnn2C)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-methylpyrazole-3-carboxylate | 1.85 | ** |
| 36 | 135 | 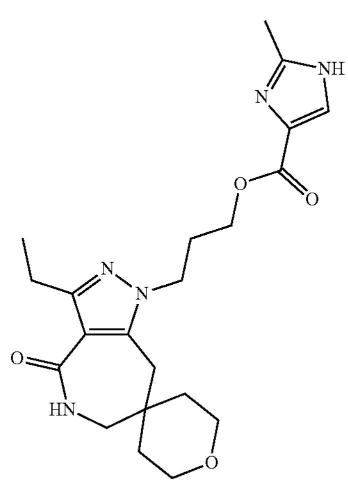 [SMILES: CCc1nn(CCCOC(=O)c2c[nH]c(C)n2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-methyl-1H-imidazole-4-carboxylate | 1.59 | ** |

TABLE 2-continued

| Ex. | Cmpd | Structure | IUPAC Name | HPLC Rt (min) | PDE4 Potency Range |
|---|---|---|---|---|---|
| 37 | 136 | 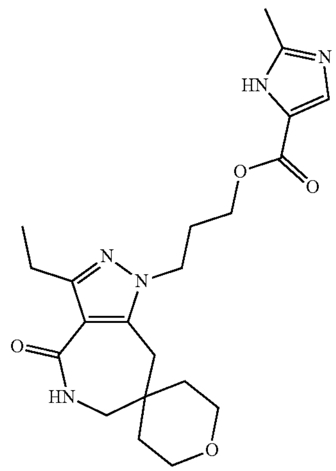 [SMILES: CCc1nn(CCCOC(=O)c2cnc(C)[nH]2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-methyl-1H-imidazole-5-carboxylate | 1.59 | ** |
| 38 | 137 | 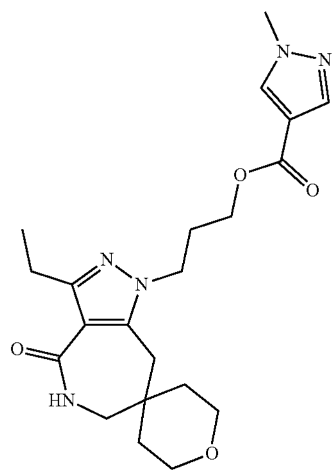 [SMILES: CCc1nn(CCCOC(=O)c2cnn(C)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 1-methylpyrazole-4-carboxylate | 1.76 | ** |
| 39 | 138 | 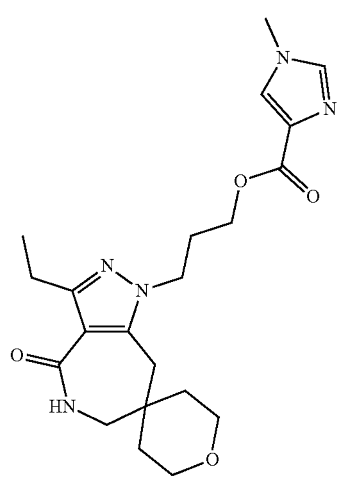 [SMILES: CCc1nn(CCCOC(=O)c2cn(C)cn2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 1-methylimidazole-4-carboxylate | 1.66 | * |

TABLE 2-continued

| Ex. | Cmpd | Structure | IUPAC Name | HPLC Rt (min) | PDE4 Potency Range |
|---|---|---|---|---|---|
| 40 | 139 | 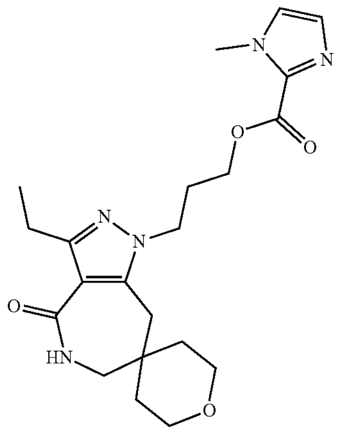 [SMILES: CCc1nn(CCCOC(=O)c2nccn2C)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 1-methylimidazole-2-carboxylate | 1.71 | ** |
| 41 | 140 | 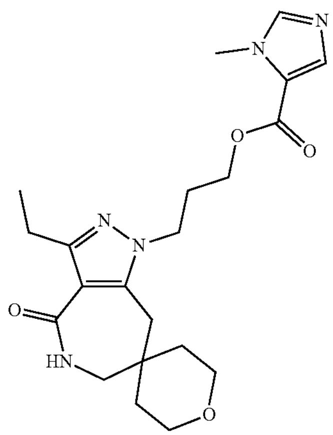 [SMILES: CCc1nn(CCCOC(=O)c2cncn2C)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-methylimidazole-4-carboxylate | 1.68 | ** |
| 42 | 141 | 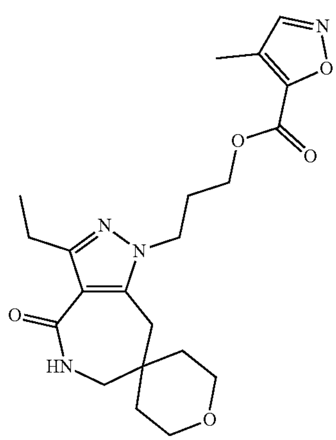 [SMILES: CCc1nn(CCCOC(=O)c2oncc2C)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-methylisoxazole-5-carboxylate | 1.91 | ** |

TABLE 2-continued

| Ex. | Cmpd | Structure | IUPAC Name | HPLC Rt (min) | PDE4 Potency Range |
|---|---|---|---|---|---|
| 43 | 142 | 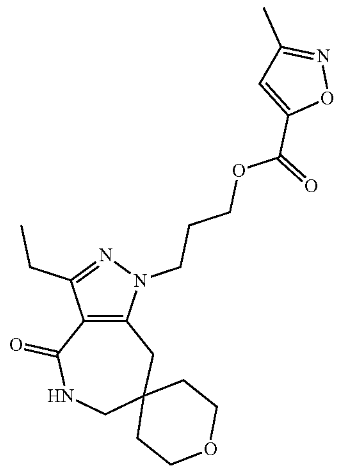 [SMILES: CCc1nn(CCCOC(=O)c2cc(C)no2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-methylisoxazole-5-carboxylate | 1.90 | ** |
| 44 | 143 | 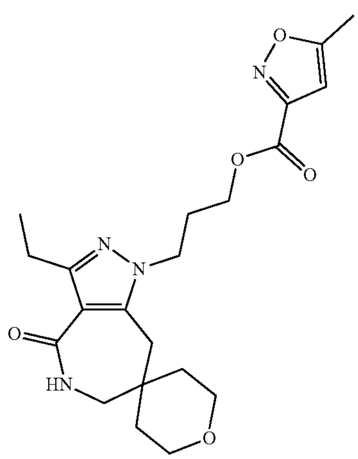 [SMILES: CCc1nn(CCCOC(=O)c2cc(C)on2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 5-methylisoxazole-3-carboxylate | 1.90 | ** |
| 45 | 144 | 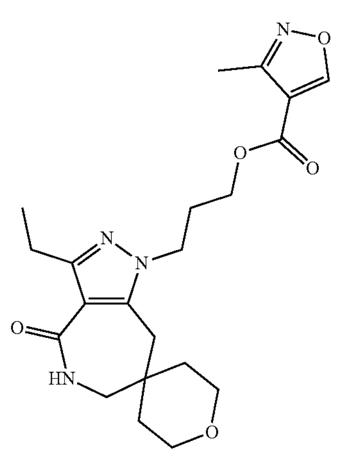 [SMILES: CCc1nn(CCCOC(=O)c2conc2C)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-methylisoxazole-4-carboxylate | 1.91 | ** |

TABLE 2-continued

| Ex. | Cmpd | Structure | IUPAC Name | HPLC Rt (min) | PDE4 Potency Range |
|---|---|---|---|---|---|
| 46 | 145 | 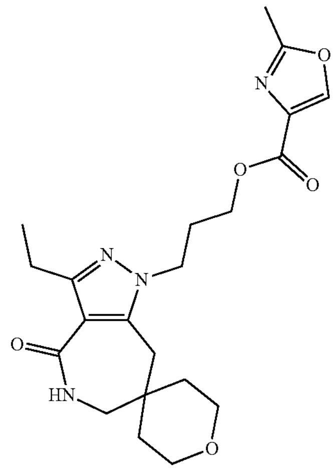 [SMILES: CCc1nn(CCCOC(=O)c2coc(C)n2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-methyloxazole-4-carboxylate | 1.78 | * |
| 47 | 146 | 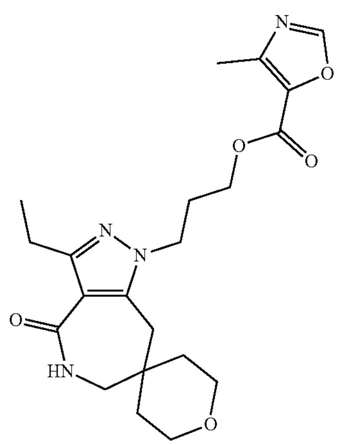 [SMILES: CCc1nn(CCCOC(=O)c2ocnc2C)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-methyloxazole-5-carboxylate | 1.81 | ** |
| 48 | 147 | 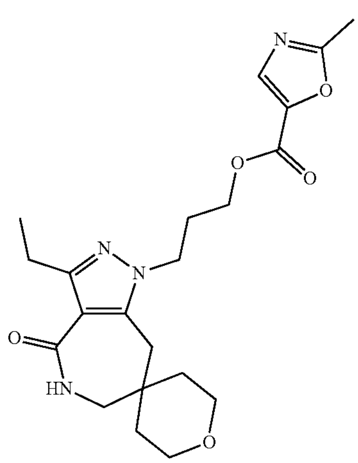 [SMILES: CCc1nn(CCCOC(=O)c2cnc(C)o2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-methyloxazole-5-carboxylate | 1.79 | ** |

TABLE 2-continued

| Ex. | Cmpd | Structure | IUPAC Name | HPLC Rt (min) | PDE4 Potency Range |
|---|---|---|---|---|---|
| 49 | 148 | 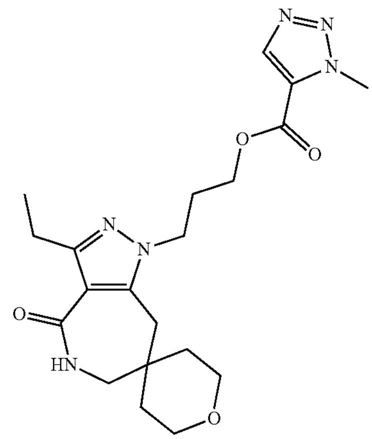 [SMILES: CCc1nn(CCCOC(=O)c2cnnn2C)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-methyltriazole-4-carboxylate | 1.78 | ** |
| 50 | 149 | 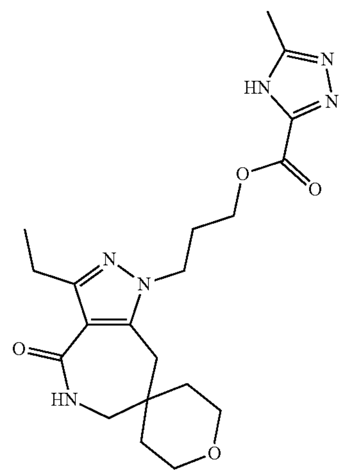 [SMILES: CCc1nn(CCCOC(=O)c2nnc(C)[nH]2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 5-methyl-4H-1,2,4-triazole-3-carboxylate | 1.63 | * |
| 51 | 150 | 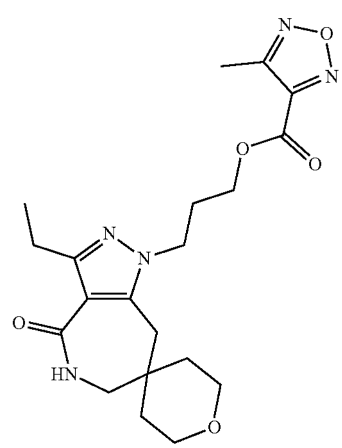 [SMILES: CCc1nn(CCCOC(=O)c2nonc2C)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-methyl-1,2,5-oxadiazole-3-carboxylate | 1.99 | ** |

TABLE 2-continued

| Ex. | Cmpd | Structure | IUPAC Name | HPLC Rt (min) | PDE4 Potency Range |
|---|---|---|---|---|---|
| 52 | 151 | 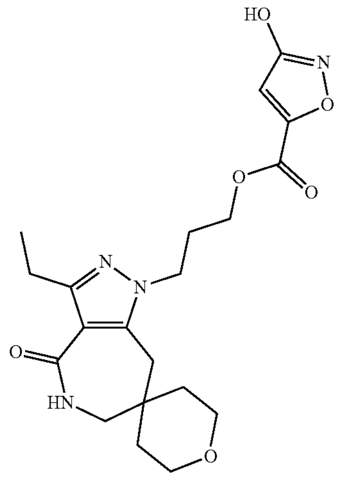 [SMILES: CCc1nn(CCCOC(=O)c2cc(O)no2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-hydroxyisoxazole-5-carboxylate | 1.78 | ** |
| 53 | 152 | 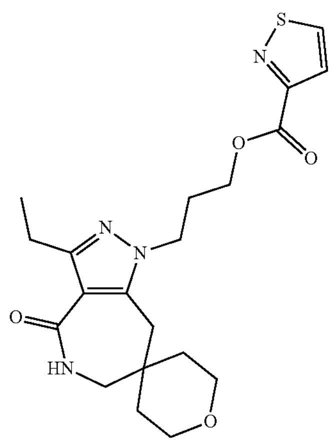 [SMILES: CCc1nn(CCCOC(=O)c2ccsn2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl isothiazole-3-carboxylate | 1.82 | ** |
| 54 | 153 | 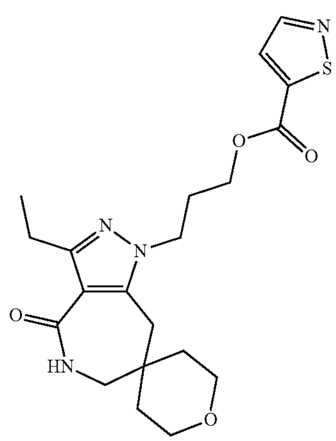 [SMILES: CCc1nn(CCCOC(=O)c2ccns2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl isothiazole-5-carboxylate | 1.82 | ** |

TABLE 2-continued

| Ex. | Cmpd | Structure | IUPAC Name | HPLC Rt (min) | PDE4 Potency Range |
|---|---|---|---|---|---|
| 55 | 154 | 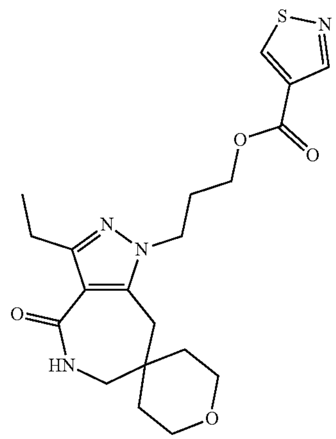 [SMILES: CCc1nn(CCCOC(=O)c2cnsc2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl isothiazole-4-carboxylate | 1.86 | ** |
| 56 | 155 | 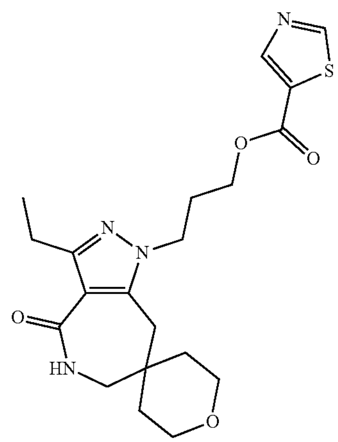 [SMILES: CCc1nn(CCCOC(=O)c2cncs2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl thiazole-5-carboxylate | 1.81 | ** |
| 57 | 156 | 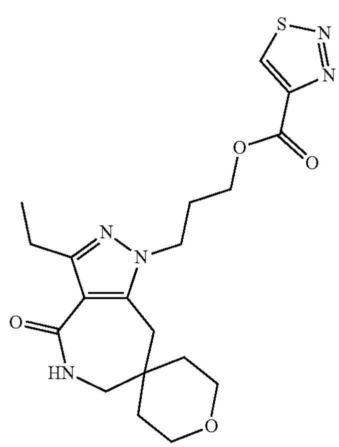 [SMILES: CCc1nn(CCCOC(=O)c2csnn2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl thiadiazole-4-carboxylate | 1.79 | ** |

TABLE 2-continued

| Ex. | Cmpd | Structure | IUPAC Name | HPLC Rt (min) | PDE4 Potency Range |
|---|---|---|---|---|---|
| 58 | 157 | 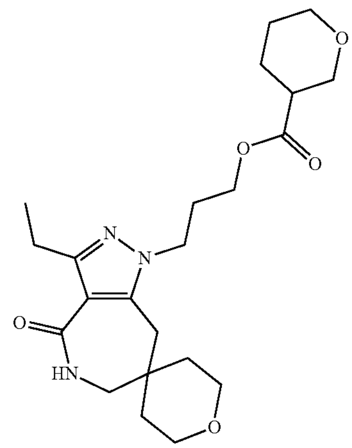 [SMILES: CCc1nn(CCCOC(=O)C2CCCOC2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl tetrahydropyran-3-carboxylate | 1.87 | * |
| 59 | 158 | 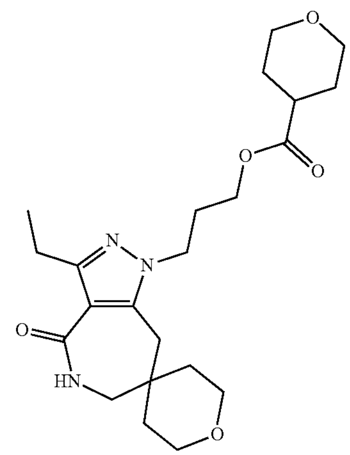 [SMILES: CCc1nn(CCCOC(=O)C2CCOCC2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl tetrahydropyran-4-carboxylate | 1.82 | * |
| 60 | 159 | 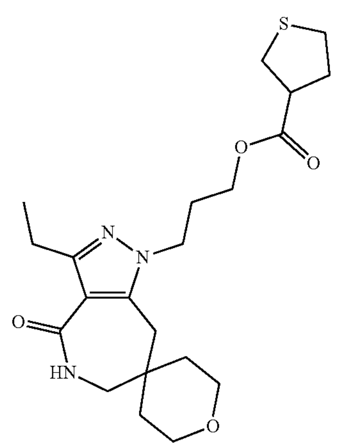 [SMILES: CCc1nn(CCCOC(=O)C2CCSC2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl tetrahydrothiophene-3-carboxylate | 1.98 | ** |

TABLE 2-continued

| Ex. | Cmpd | Structure | IUPAC Name | HPLC Rt (min) | PDE4 Potency Range |
|---|---|---|---|---|---|
| 61 | 160 | 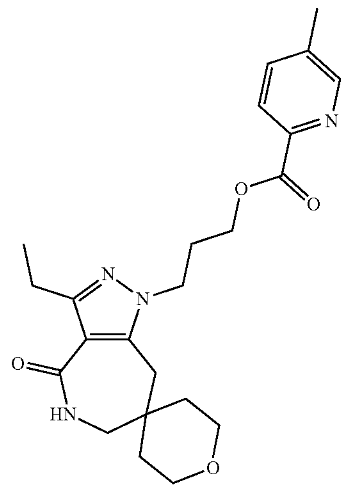 [SMILES: CCc1nn(CCCOC(=O)c2ccc(C)cn2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 5-methylpyridine-2-carboxylate | 1.84 | ** |
| 62 | 161 | 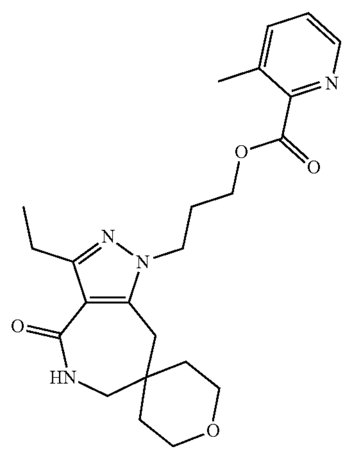 [SMILES: CCc1nn(CCCOC(=O)c2ncccc2C)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-methylpyridine-2-carboxylate | 1.86 | * |
| 63 | 162 | 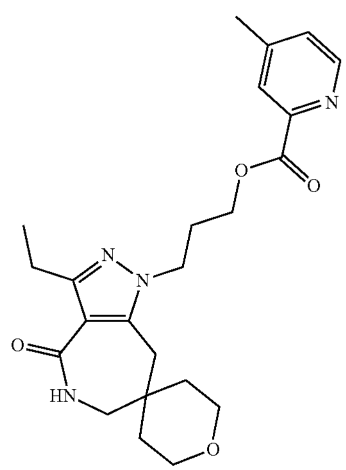 [SMILES: CCc1nn(CCCOC(=O)c2cc(C)ccn2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-methylpyridine-2-carboxylate | 1.83 | * |

TABLE 2-continued

| Ex. | Cmpd | Structure | IUPAC Name | HPLC Rt (min) | PDE4 Potency Range |
|---|---|---|---|---|---|
| 64 | 163 | 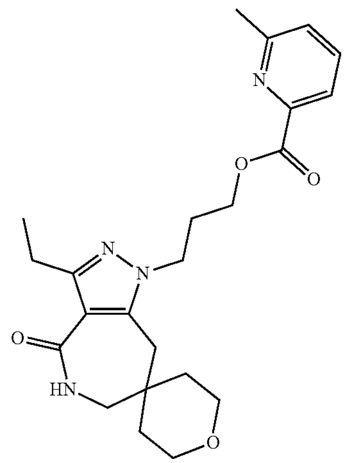 [SMILES: CCc1nn(CCCOC(=O)c2cccc(C)n2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 6-methylpyridine-2-carboxylate | 1.82 | * |
| 65 | 164 | 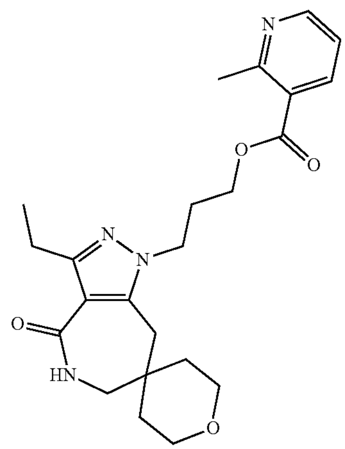 [SMILES: CCc1nn(CCCOC(=O)c2cccnc2C)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-methylpyridine-3-carboxylate | 1.80 | ** |
| 66 | 165 | 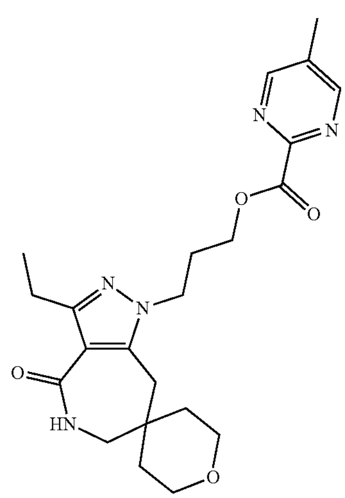 [SMILES: CCc1nn(CCCOC(=O)c2ncc(C)cn2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 5-methylpyrimidine-2-carboxylate | 1.71 | * |

TABLE 2-continued

| Ex. | Cmpd | Structure | IUPAC Name | HPLC Rt (min) | PDE4 Potency Range |
|---|---|---|---|---|---|
| 67 | 166 | 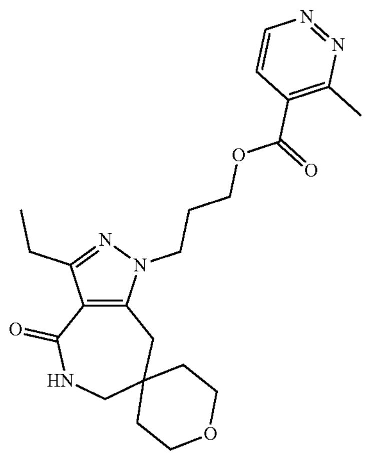 [SMILES: CCc1nn(CCCOC(=O)c2ccnnc2C)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-methylpyridazine-4-carboxylate | 1.75 | * |
| 68 | 167 | 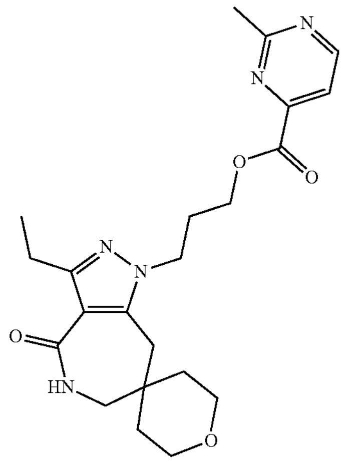 [SMILES: CCc1nn(CCCOC(=O)c2ccnc(C)n2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-methylpyrimidine-4-carboxylate | 1.73 | * |
| 69 | 168 | 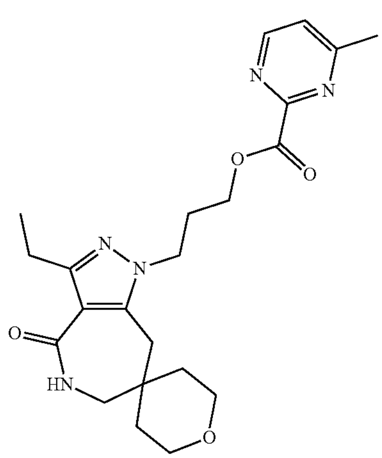 [SMILES: CCc1nn(CCCOC(=O)c2nccc(C)n2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-methylpyrimidine-2-carboxylate | 1.69 | * |

TABLE 2-continued

| Ex. | Cmpd | Structure | IUPAC Name | HPLC Rt (min) | PDE4 Potency Range |
|---|---|---|---|---|---|
| 70 | 169 | 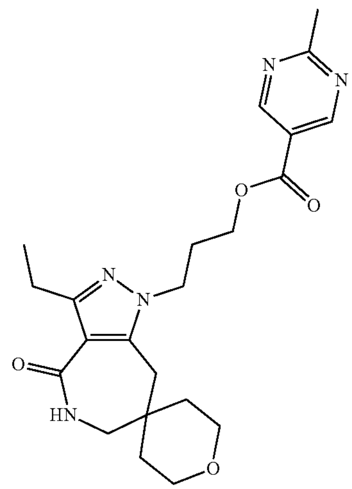 [SMILES: CCc1nn(CCCOC(=O)c2cnc(C)nc2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-methylpyrimidine-5-carboxylate | 1.77 | ** |
| 71 | 170 | 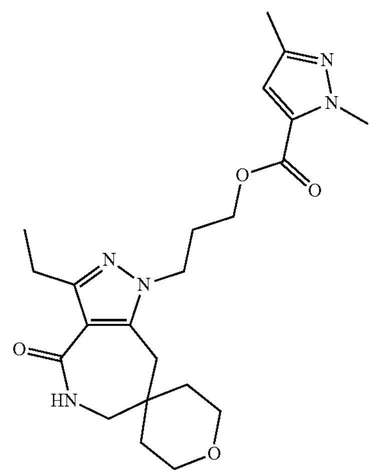 [SMILES: CCc1nn(CCCOC(=O)c2cc(C)nn2C)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2,5-dimethylpyrazole-3-carboxylate | 1.90 | ** |
| 72 | 171 | 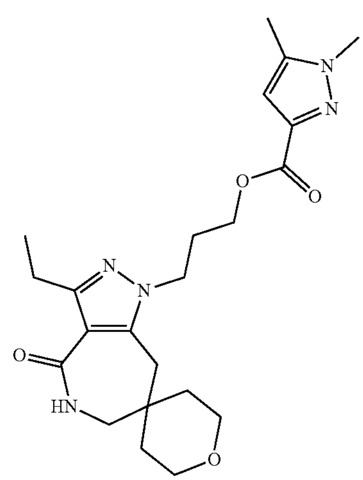 [SMILES: CCc1nn(CCCOC(=O)c2cc(C)n(C)n2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 1,5-dimethylpyrazole-3-carboxylate | 1.81 | * |

TABLE 2-continued

| Ex. | Cmpd | Structure | IUPAC Name | HPLC Rt (min) | PDE4 Potency Range |
|---|---|---|---|---|---|
| 73 | 172 | 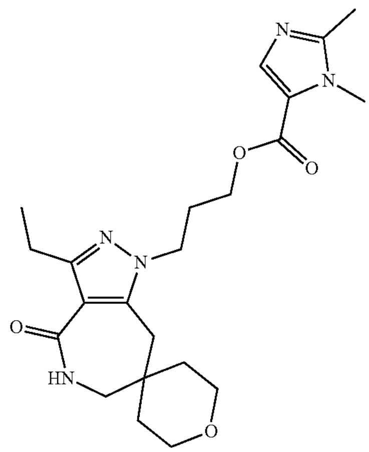 [SMILES: CCc1nn(CCCOC(=O)c2cnc(C)n2C)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2,3-dimethylimidazole-4-carboxylate | 1.63 | ** |
| 74 | 173 | 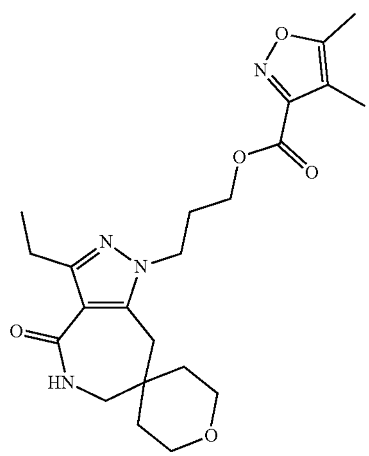 [SMILES: CCc1nn(CCCOC(=O)c2noc(C)c2C)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4,5-dimethylisoxazole-3-carboxylate | 1.98 | ** |
| 75 | 174 | 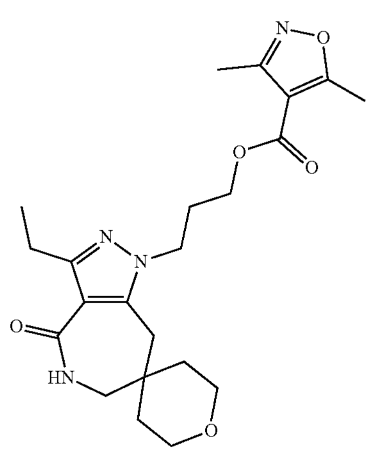 [SMILES: CCc1nn(CCCOC(=O)c2c(C)noc2C)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3,5-dimethylisoxazole-4-carboxylate | 1.97 | * |

TABLE 2-continued

| Ex. | Cmpd | Structure | IUPAC Name | HPLC Rt (min) | PDE4 Potency Range |
|---|---|---|---|---|---|
| 76 | 175 | 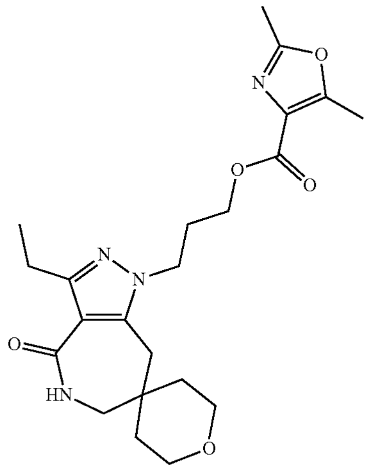 [SMILES: CCc1nn(CCCOC(=O)c2nc(C)oc2C)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2,5-dimethyloxazole-4-carboxylate | 1.84 | * |
| 77 | 176 | 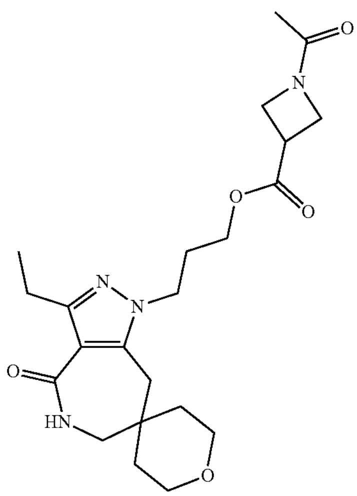 [SMILES: CCc1nn(CCCOC(=O)C2CN(C(C)=O)C2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 1-acetylazetidine-3-carboxylate | 1.68 | * |
| 78 | 177 | 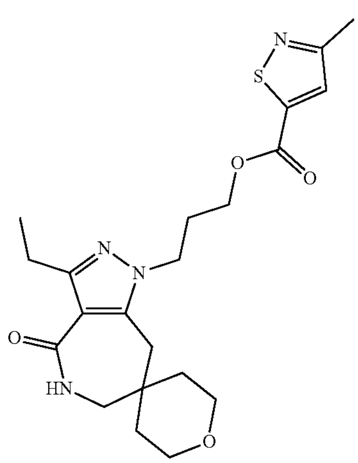 [SMILES: CCc1nn(CCCOC(=O)c2cc(C)ns2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-methylisothiazole-5-carboxylate | 1.97 | ** |

TABLE 2-continued

| Ex. | Cmpd | Structure | IUPAC Name | HPLC Rt (min) | PDE4 Potency Range |
|---|---|---|---|---|---|
| 79 | 178 | 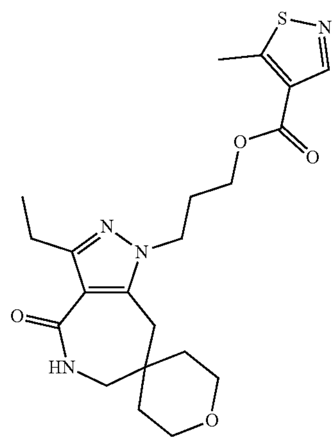 [SMILES: CCc1nn(CCCOC(=O)c2cnsc2C)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 5-methylisothiazole-4-carboxylate | 1.95 | ** |
| 80 | 179 | 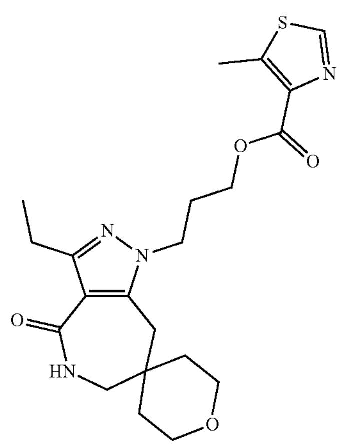 [SMILES: CCc1nn(CCCOC(=O)c2ncsc2C)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 5-methylthiazole-4-carboxylate | 1.84 | ** |
| 81 | 180 | 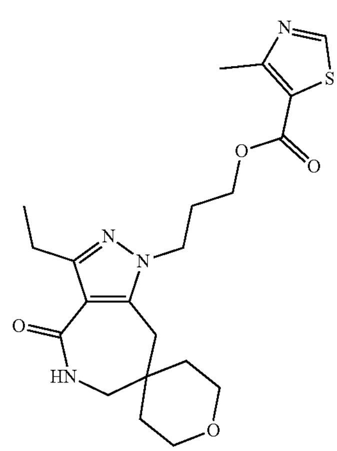 [SMILES: CCc1nn(CCCOC(=O)c2scnc2C)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-methylthiazole-5-carboxylate | 1.87 | ** |

TABLE 2-continued

| Ex. | Cmpd | Structure | IUPAC Name | HPLC Rt (min) | PDE4 Potency Range |
|---|---|---|---|---|---|
| 82 | 181 | 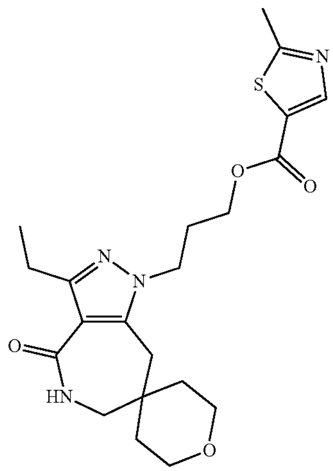 [SMILES: CCc1nn(CCCOC(=O)c2cnc(C)s2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-methylthiazole-5-carboxylate | 1.86 | ** |
| 83 | 182 | 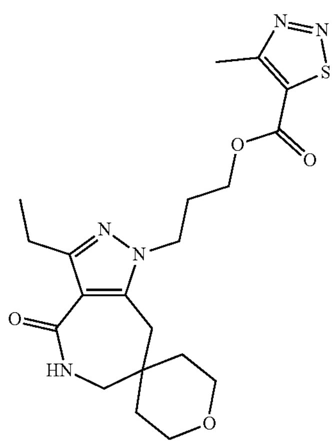 [SMILES: CCc1nn(CCCOC(=O)c2snnc2C)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-methylthiadiazole-5-carboxylate | 1.94 | * |
| 84 | 183 | 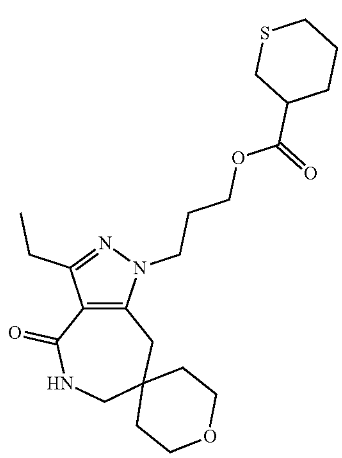 [SMILES: CCc1nn(CCCOC(=O)C2CCCSC2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl tetrahydrothiopyran-3-carboxylate | 2.04 | ** |

TABLE 2-continued

| Ex. | Cmpd | Structure | IUPAC Name | HPLC Rt (min) | PDE4 Potency Range |
|---|---|---|---|---|---|
| 85 | 184 | 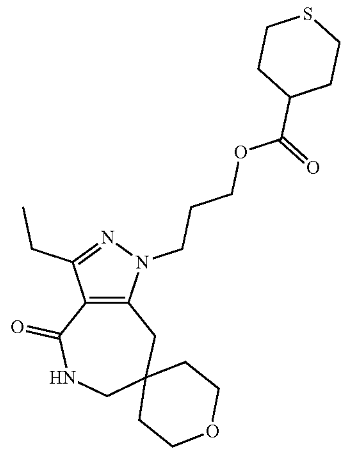 | 3-(3-ethyl-4-oxo-spiro[6,8-dihydro-5H-pyrazolo[4,3-c]azepine-7,4'-tetrahydropyran]-1-yl)propyl tetrahydrothiopyran-4-carboxylate | 2.02 | ** |
| 86 | 185 | 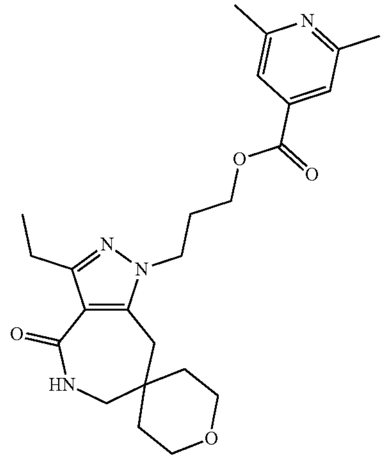 [SMILES: CCc1nn(CCCOC(=O)c2cc(C)nc(C)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2,6-dimethylpyridine-4-carboxylate | 1.78 | ** |
| 87 | 186 | 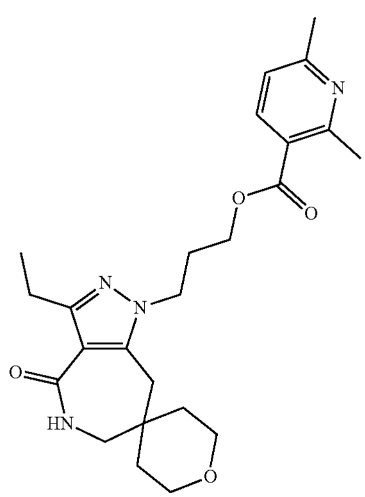 [SMILES: CCc1nn(CCCOC(=O)c2ccc(C)nc2C)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2,6-dimethylpyridine-3-carboxylate | 1.77 | *** |

TABLE 2-continued

| Ex. | Cmpd | Structure | IUPAC Name | HPLC Rt (min) | PDE4 Potency Range |
|---|---|---|---|---|---|
| 88 | 187 | 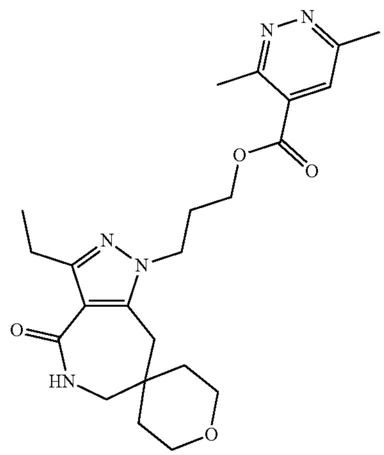 [SMILES: CCc1nn(CCCOC(=O)c2cc(C)nnc2C)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3,6-dimethylpyridazine-4-carboxylate | 1.78 | * |
| 89 | 188 | 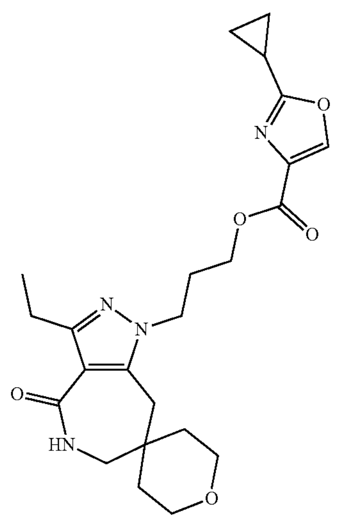 [SMILES: CCc1nn(CCCOC(=O)c2coc(C3CC3)n2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-cyclopropyloxazole-4-carboxylate | 1.89 | ** |
| 90 | 189 | 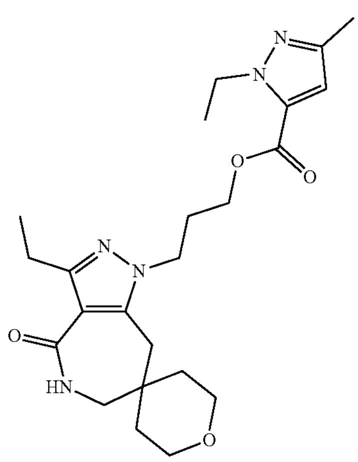 [SMILES: CCc1nn(CCCOC(=O)c2cc(C)nn2CC)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-ethyl-5-methyl-pyrazole-3-carboxylate | 1.97 | ** |

TABLE 2-continued

| Ex. | Cmpd | Structure | IUPAC Name | HPLC Rt (min) | PDE4 Potency Range |
|---|---|---|---|---|---|
| 91 | 190 | 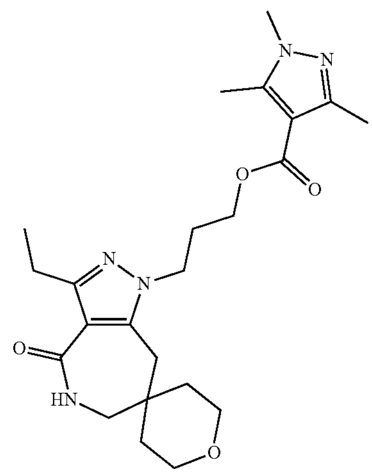 [SMILES: CCc1nn(CCCOC(=O)c2c(C)nn(C)c2C)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 1,3,5-trimethylpyrazole-4-carboxylate | 1.85 | ** |
| 92 | 191 | 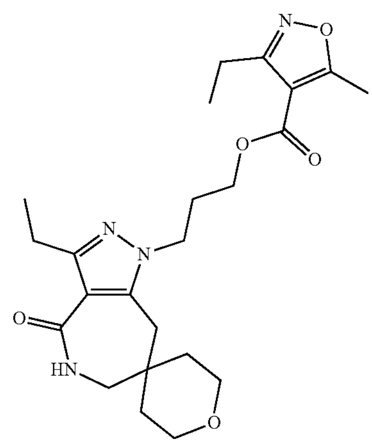 [SMILES: CCc1noc(C)c1C(=O)OCCCn1nc(CC)c2c1CC1(CCOCC1)CNC2=O] | 3-(3-ethyl-4-oxo-spiro[6,8-dihydro-5H-pyrazolo[4,3-c]azepine-7,4'-tetrahydropyran]-1-yl)propyl 3-ethyl-5-methyl-isoxazole-4-carboxylate | 2.05 | * |
| 93 | 192 | 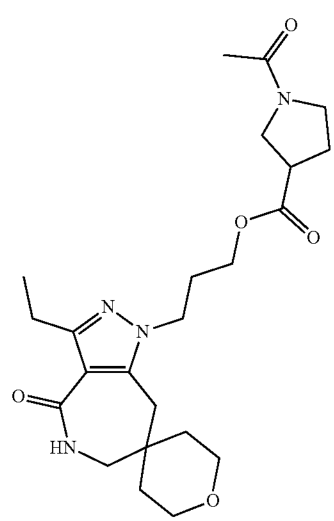 [SMILES: CCc1nn(CCCOC(=O)C2CCN(C(C)=O)C2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 1-acetylpyrrolidine-3-carboxylate | 1.72 | * |

TABLE 2-continued

| Ex. | Cmpd | Structure | IUPAC Name | HPLC Rt (min) | PDE4 Potency Range |
|---|---|---|---|---|---|
| 94 | 193 | 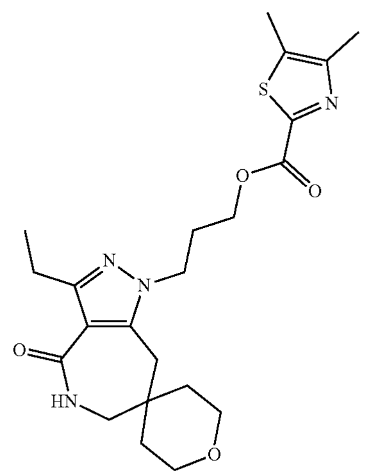 [SMILES: CCc1nn(CCCOC(=O)c2nc(C)c(C)s2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4,5-dimethylthiazole-2-carboxylate | 1.93 | ** |
| 95 | 194 | 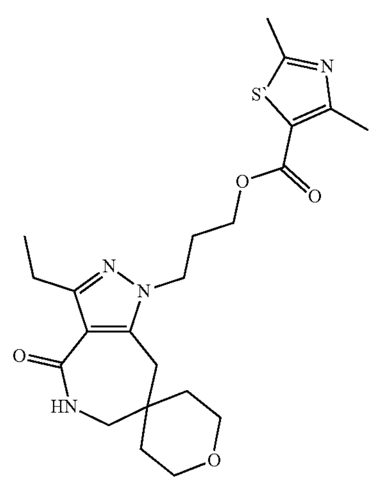 | 3-(3-ethyl-4-oxo-spiro[6,8-dihydro-5H-pyrazolo[4,3-c]azepine-7,4'-tetrahydropyran]-1-yl)propyl 2,4-dimethylthiazole-5-carboxylate | 1.91 | ** |
| 96 | 195 | 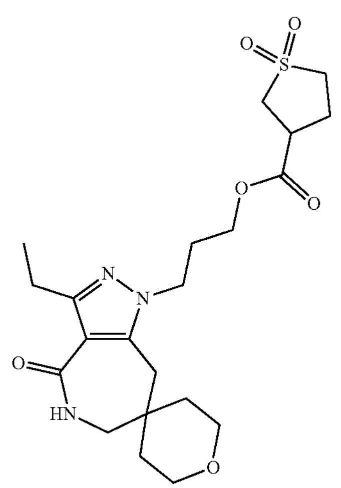 [SMILES: CCc1nn(CCCOC(=O)C2CCS(=O)(=O)C2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 1,1-dioxothiolane-3-carboxylate | 1.75 | * |

TABLE 2-continued

| Ex. | Cmpd | Structure | IUPAC Name | HPLC Rt (min) | PDE4 Potency Range |
|---|---|---|---|---|---|
| 97 | 196 | 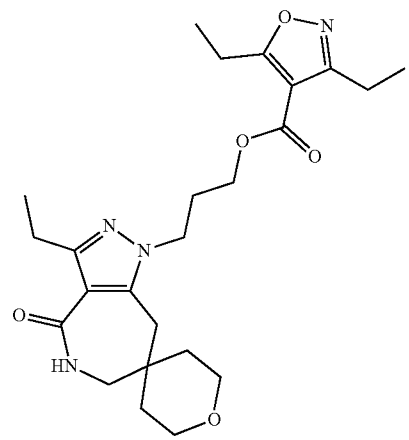 [SMILES: CCc1noc(CC)c1C(=O)OCCCn1nc(CC)c2c1CC1(CCOCC1)CNC2=O] | 3-(3-ethyl-4-oxo-spiro[6,8-dihydro-5H-pyrazolo[4,3-c]azepine-7,4'-tetrahydropyran]-1-yl)propyl 3,5-diethylisoxazole-4-carboxylate | 2.15 | ** |
| 98 | 197 | 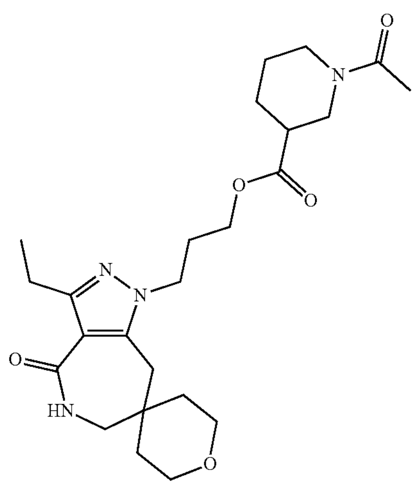 [SMILES: CCc1nn(CCCOC(=O)C2CCCN(C(C)=O)C2)c2c1C(=O)NCC1(CCOCC1)C2] | 3-(3-ethyl-4-oxo-spiro[6,8-dihydro-5H-pyrazolo[4,3-c]azepine-74'-tetrahydropyran]-1-yl)propyl 1-acetylpiperidine-3-carboxylate | 1.78 | * |
| 99 | 198 | 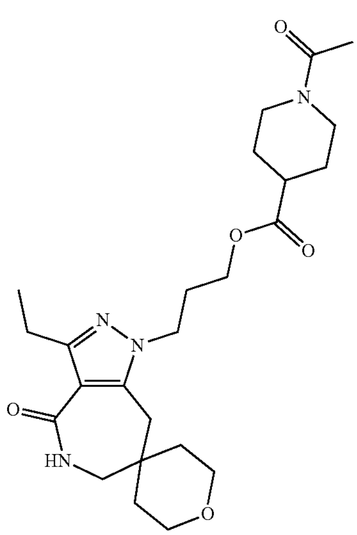 [SMILES: CCc1nn(CCCOC(=O)C2CCN(C(C)=O)CC2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 1-acetylpiperidine-4-carboxylate | 1.75 | * |

TABLE 2-continued

| Ex. | Cmpd | Structure | IUPAC Name | HPLC Rt (min) | PDE4 Potency Range |
|---|---|---|---|---|---|
| 100 | 199 | 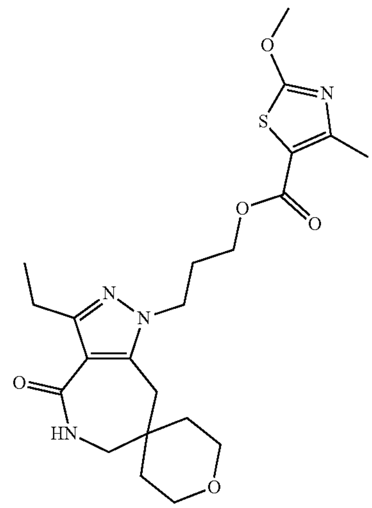 [SMILES: CCc1nn(CCCOC(=O)c2sc(OC)nc2C)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-methoxy-4-methyl-thiazole-5-carboxylate | 2.01 | ** |
| 101 | 200 | 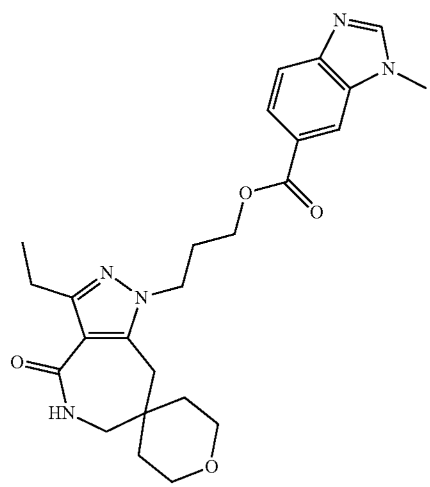 [SMILES: CCc1nn(CCCOC(=O)c2ccc3ncn(C)c3c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-methylbenzimidazole-5-carboxylate | 1.77 | *** |
| 102 | 201 | 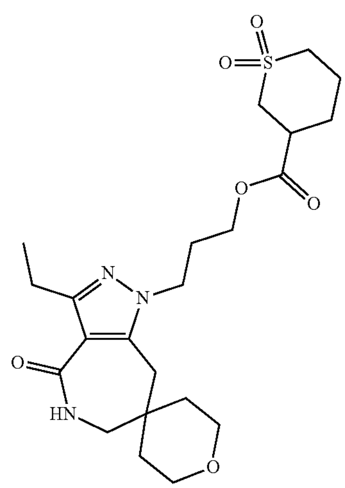 [SMILES: CCc1nn(CCCOC(=O)C2CCCS(=O)(=O)C2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 1,1-dioxothiane-3-carboxylate | 1.78 | * |

TABLE 2-continued

| Ex. | Cmpd | Structure | IUPAC Name | HPLC Rt (min) | PDE4 Potency Range |
|---|---|---|---|---|---|
| 103 | 202 | 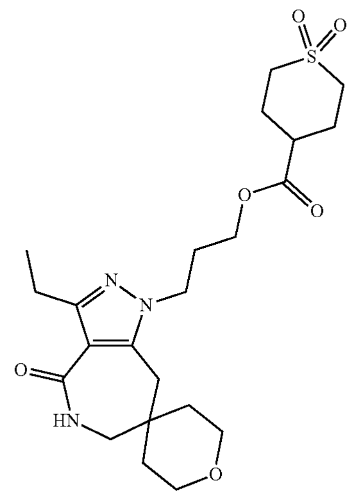 [SMILES: CCc1nn(CCCOC(=O)C2CCS(=O)(=O)CC2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 1,1-dioxothiane-4-carboxylate | 1.76 | * |
| 104 | 203 | 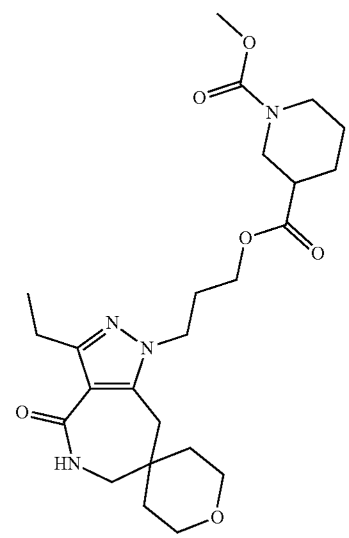 [SMILES: CCc1nn(CCCOC(=O)C2CCCN(C(=O)OC)C2)c2c1C(=O)NCC1(CCOCC1)C2] | O3-[3-(3-ethyl-4-oxo-spiro[6,8-dihydro-5H-pyrazolo[4,3-c]azepine-7,4'-tetrahydropyran]-1-yl)propyl] O1-methyl piperidine-1,3-dicarboxylate | 1.92 | ** |
| 105 | 204 | 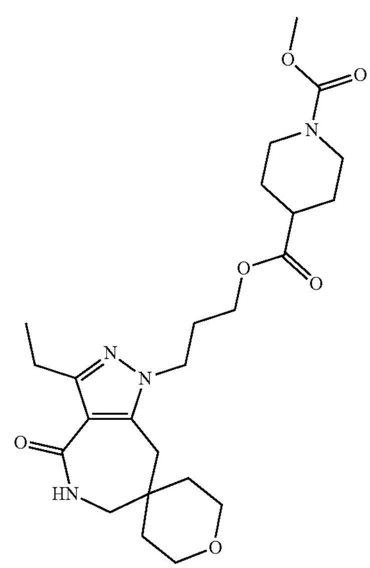 [SMILES: CCc1nn(CCCOC(=O)C2CCN(C(=O)OC)CC2)c2c1C(=O)NCC1(CCOCC1)C2] | O4-[3-(3-ethyl-4-oxo-spiro[6,8-dihydro-5H-pyrazolo[4,3-c]azepine-7,4'-tetrahydropyran]-1-yl)propyl] O1-methyl piperidine-1,4-dicarboxylate | 1.89 | ** |

TABLE 2-continued

| Ex. | Cmpd | Structure | IUPAC Name | HPLC Rt (min) | PDE4 Potency Range |
|---|---|---|---|---|---|
| 106 | 205 | 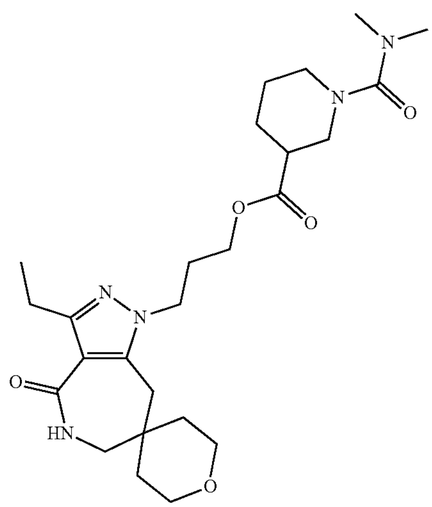 [SMILES: CCc1nn(CCCOC(=O)C2CCCN(C(=O)N(C)C)C2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 1-(dimethylcarbamoyl)piperidine-3-carboxylate | 1.86 | ** |
| 107 | 206 | 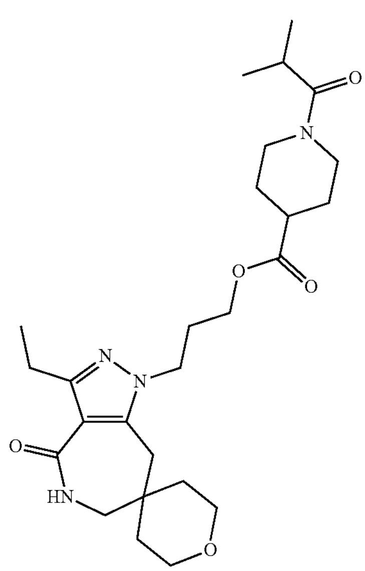 [SMILES: CCc1nn(CCCOC(=O)C2CCN(C(=O)C(C)C)CC2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 1-(dimethylcarbamoyl)piperidine-4-carboxylate | 1.84 | ** |

The Examples 108-109 shown in Table 3 were prepared by reacting Compound 021 as described in General Procedure 2 with the appropriate acid:

TABLE 3

| Ex. | Cmpd | Structure | IUPAC Name | HPLC Rt (min) | PDE4 Potency Range |
|---|---|---|---|---|---|
| 108 | 207 | 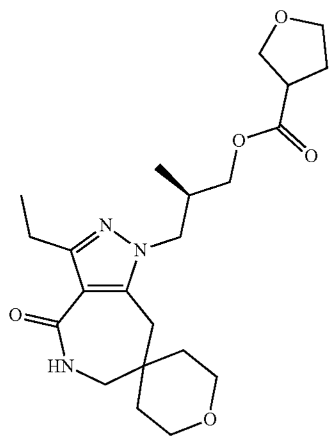 [SMILES: CCc1nn(C[C@@H](C)COC(=O)C2CCOC2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] tetrahydrofuran-3-carboxylate | 1.87 | *** |
| 109 | 208 | 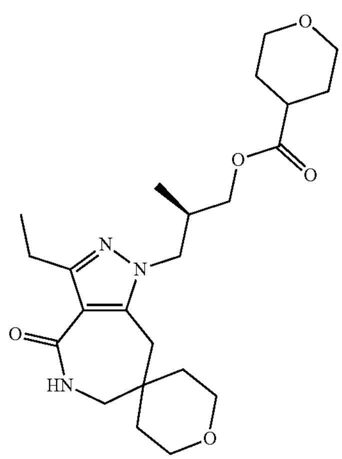 [SMILES: CCc1nn(C[C@@H](C)COC(=O)C2CCOCC2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] tetrahydropyran-4-carboxylate | 1.90 | *** |

The Examples 110-111 shown in Table 4 were prepared by reacting Compound 028 as described in General Procedure 2 with the appropriate acid:

TABLE 4

| Ex. | Cmpd | Structure | IUPAC Name | HPLC Rt (min) | PDE4 Potency Range |
|---|---|---|---|---|---|
| 110 | 209 | 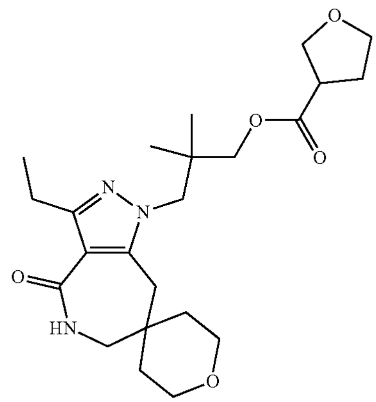 [SMILES: CCc1nn(CC(C)(C)COC(=O)C2CCOC2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] tetrahydrofuran-3-carboxylate | 1.97 | ** |
| 111 | 210 | 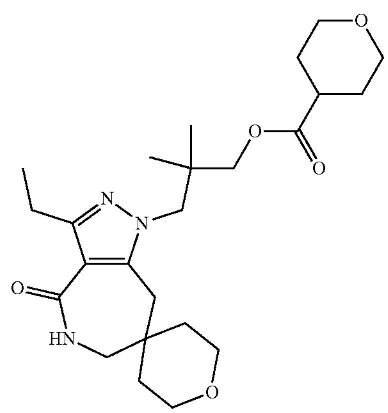 [SMILES: CCc1nn(CC(C)(C)COC(=O)C2CCOCC2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] tetrahydropyran-4-carboxylate | 2.00 | ** |

The Examples 112-115 shown in Table 5 were prepared by reacting Compound 031 as described in General Procedure 2 with the appropriate acid:

TABLE 5

| Ex. | Cmpd | Structure | IUPAC Name | HPLC Rt (min) | PDE4 Potency Range |
|---|---|---|---|---|---|
| 112 | 211 | 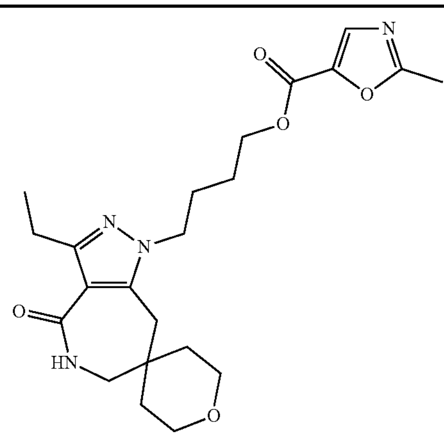 | 4-(3-ethyl-4-oxo-spiro[6,8-dihydro-5H-pyrazolo[4,3-c]azepine-7,4'-tetrahydropyran]-1-yl)butyl 2-methyloxazole-5-carboxylate | | |

TABLE 5-continued

| Ex. | Cmpd | Structure | IUPAC Name | HPLC Rt (min) | PDE4 Potency Range |
|---|---|---|---|---|---|
| 113 | 212 | 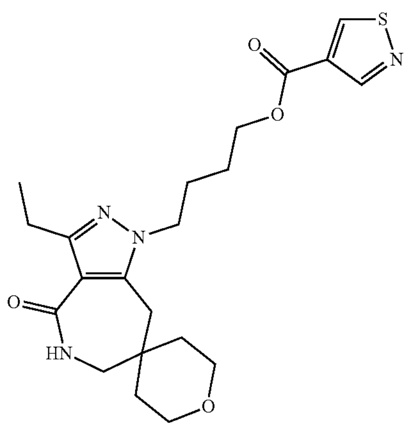 [SMILES: CCc1nn(CCCCOC(=O)c2cnsc2)c2c1C(=O)NCC1(CCOCC1)C2] | 4-(3-ethyl-4-oxo-spiro[6,8-dihydro-5H-pyrazolo[4,3-c]azepine-7,4'-tetrahydropyran]-1-yl)butyl isothiazole-4-carboxylate | | |
| 114 | 213 | 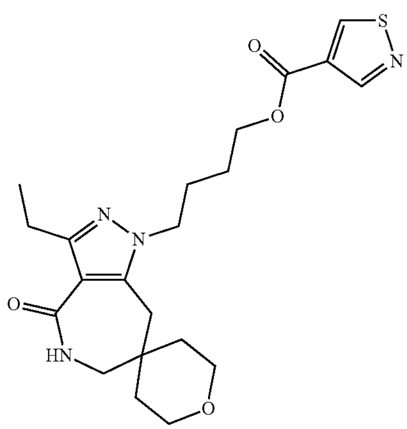 [SMILES: CCc1nn(CCCCOC(=O)c2cnsc2)c2c1C(=O)NCC1(CCOCC1)C2] | 4-(3-ethyl-4-oxo-spiro[6,8-dihydro-5H-pyrazolo[4,3-c]azepine-7,4'-tetrahydropyran]-1-yl)butyl thiazole-4-carboxylate | | |
| 115 | 214 | 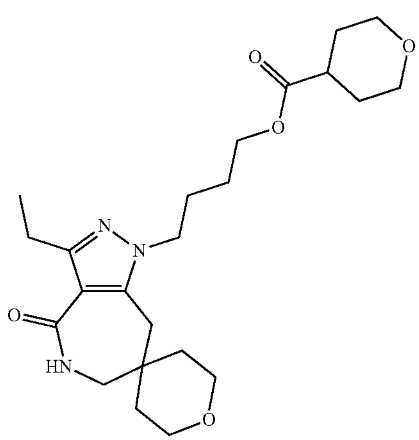 [SMILES: CCc1nn(CCCCOC(=O)C2CCOCC2)c2c1C(=O)NCC1(CCOCC1)C2] | 4-(3-ethyl-4-oxo-spiro[6,8-dihydro-5H-pyrazolo[4,3-c]azepine-7,4'-tetrahydropyran]-1-yl)butyl tetrahydropyran-4-carboxylate | | |

Clauses

In view of the description the present inventors have in particular provided:

Clause 1. A compound of general formula (I)

$$\text{(I)}$$

wherein $R_1$ and $R_4$ are independently selected from the group consisting of hydrogen and $(C_1-C_4)$alkyl;

$R_2$ and $R_3$ are independently selected from the group consisting of hydrogen and $(C_1-C_4)$alkyl; or $R_2$ and $R_3$ together with the carbon atom to which they are attached form a cyclopropyl, cyclobutyl, cyclopentyl, oxetanyl, tetrahydrofuranyl, or tetrahydropyranyl ring;

n=0, 1 or 2; and when n is 0, $R_4$ does not exist;

Q is selected from the group consisting of —O—C(O)—$R_5$ and —O—C(O)—$(C_1-C_6)$alkyl-$R_5$;

$R_5$ is selected from the group consisting of heteroaryl and heterocycloalkyl, wherein said heteroaryl and heterocycloalkyl are optionally substituted with one or more substituents independently selected from $R_6$;

$R_6$ consists of halogen, cyano, hydroxyl, $(C_1-C_4)$alkyl, halo$(C_1-C_4)$alkyl, $(C_1-C_4)$alkyloxy, —S(O)$_2R_x$, —S(O)$_2$NR$_a$R$_b$, —OR$_x$, —C(O)NR$_a$R$_b$, —C(O)OR$_a$, —C(O)R$_a$, cycloalkyl, aryl and heteroaryl;

$R_x$ is $(C_1-C_4)$alkyl;

$R_a$ and $R_b$ are independently selected from the group consisting of hydrogen, $(C_1-C_4)$alkyl, phenyl-$(C_1-C_4)$alkyl, or $R_a$ and $R_b$ together with the nitrogen to which they are attached form a 4-6 membered heterocycloalkyl, wherein said heterocycloalkyl is optionally substituted with one or more $(C_1-C_4)$alkyl; and pharmaceutically acceptable salts, hydrates or solvates thereof.

Clause 2. A compound according to clause 1 wherein $R_1$ and $R_4$ are independently selected from the group consisting of hydrogen and $(C_1-C_4)$alkyl;

$R_2$ and $R_3$ are independently selected from the group consisting of hydrogen and $(C_1-C_4)$alkyl;

n=0, 1 or 2; and when n is 0, $R_4$ does not exist;

Q is selected from the group consisting of —O—C(O)—$R_5$ and —C(O)—$(C_1-C_6)$alkyl-$R_5$;

$R_5$ is selected from the group consisting of a (5-6) membered heteroaryl, a (9-10) membered heteroaryl and a (4-6) membered heterocycloalkyl, wherein said heteroaryl and heterocycloalkyl are optionally substituted with one or more substituents independently selected from $R_6$;

$R_6$ consists of halogen, cyano, hydroxyl, $(C_1-C_4)$alkyl, halo$(C_1-C_4)$alkyl, $(C_1-C_4)$alkyloxy, —OR$_x$, —C(O)NR$_a$R$_b$, —C(O)OR$_a$, —C(O)R$_a$, and cycloalkyl;

$R_x$ is $(C_1-C_4)$alkyl;

$R_a$ and $R_b$ are independently selected from the group consisting of hydrogen and $(C_1-C_4)$alkyl, and pharmaceutically acceptable salts, hydrates or solvates thereof.

Clause 3. A compound according to clause 1 or 2 wherein all of $R_1$, $R_2$, $R_3$ are hydrogen, n is 0, Q is selected from the group consisting of —O—C(O)—$R_5$ and —O—C(O)($C_1-C_6$)alkyl-$R_5$, wherein $R_5$ is selected from the group consisting of a (5-6) membered heteroaryl and a (4-6) membered heterocycloalkyl, wherein said heteroaryl and heterocycloalkyl are optionally substituted with one or more substituents independently selected from $(C_1-C_4)$alkyl, $(C_1-C_4)$alkyloxy, —C(O)R$_a$, and $(C_3-C_6)$cycloalkyl, wherein $R_a$ is $(C_1-C_4)$alkyl.

Clause 4. A compound according to clause 3 wherein all of $R_1$, $R_2$, $R_3$ are hydrogen, n is 0, Q is —O—C(O)—$R_5$; wherein $R_5$ is a (5-6) membered heteroaryl optionally substituted with one or more of $(C_1-C_4)$alkyl.

Clause 5. A compound according to clause 4 wherein all of $R_1$, $R_2$, $R_3$ are hydrogen, n is 0, Q is —O—C(O)—$R_5$; wherein $R_5$ is selected from the group consisting of isoxazolyl, oxazolyl, pyrazolyl, thiazolyl, isothiazolyl, all of which are optionally substituted with one or more of $(C_1-C_4)$alkyl.

Clause 6. A compound according to clause 3 wherein all of $R_1$, $R_2$, $R_3$ are hydrogen, n is 0, Q is —C(O)—$R_5$; wherein $R_5$ is a (4-6) membered heterocycloalkyl optionally substituted with one or more of —C(O)R$_a$, wherein $R_a$ is $(C_1-C_4)$alkyl.

Clause 7. A compound according to clause 6 whereinall of $R_1$, $R_2$, $R_3$ are hydrogen, n is 0, Q is —O—C(O)—$R_5$; wherein $R_5$ is selected from the group consisting of tetrahydropyranyl and piperidinyl, optionally substituted with —C(O)R$_a$, wherein $R_a$ is $(C_1-C_4)$alkyl.

Clause 8. A compound according to clause 3 wherein all of $R_1$, $R_2$, $R_3$ are hydrogen, n is 0, Q is —O—C(O)—($C_1-C_6$)alkyl-$R_5$; wherein $R_5$ is a (5-6) membered heteroaryl optionally substituted with one or more of $(C_1-C_4)$alkyl.

Clause 9. A compound according to clause 8 wherein all of $R_1$, $R_2$, $R_3$ are hydrogen, n is 0, Q is —O—C(O)—($C_1-C_6$)alkyl-$R_5$; wherein $R_5$ is selected from the group consisting of pyrrolyl, isoxazolyl and thiazolyl, all of which are optionally substituted with one or more of $(C_1-C_4)$alkyl.

Clause 10. A compound according to clause 1 or 2 wherein all of $R_1$, $R_2$, $R_3$, $R_4$ are hydrogen, n is 1, Q is —O—C(O)—$R_5$, wherein $R_5$ is selected from the group consisting of a (5-6) membered heteroaryl, a (9-10) membered heteroaryl, and a (4-6) membered heterocycloalkyl, wherein said heteroaryl and heterocycloalkyl are optionally substituted with one or more substituents independently selected from $R_6$, wherein $R_6$ consists of hydroxyl, $(C_1-C_4)$alkyl, $(C_1-C_4)$alkyloxy, —OR$_x$, —C(O)NR$_a$R$_b$, —C(O)OR$_a$, —C(O)R$_a$, and $(C_3-C_6)$cycloalkyl, wherein $R_x$, $R_a$, $R_b$ are all $(C_1-C_4)$alkyl.

Clause 11. A compound according to clause 10 wherein all of $R_1$, $R_2$, $R_3$, $R_4$ are hydrogen, n is 1, Q is —O—C(O)—$R_5$; wherein $R_5$ is a (5-6) membered or a (9-10) membered heteroaryl, optionally substituted with one or more substituents independently selected from $R_6$, wherein $R_6$ consists of hydroxyl, $(C_1-C_4)$alkyl, $(C_1-C_4)$alkyloxy, —OR$_x$, —C(O)NR$_a$R$_b$, —C(O)OR$_a$, —C(O)R$_a$, and $(C_3-C_6)$cycloalkyl, wherein $R_x$, $R_a$, $R_b$ are all $(C_1-C_4)$alkyl.

Clause 12. A compound according to clause 11 wherein all of $R_1$, $R_2$, $R_3$, $R_4$ are hydrogen, n is 1, Q is —O—C(O)—$R_5$; wherein $R_5$ is selected from the group consisting of imidazolyl, pyrazolyl, isoxazolyl, oxazolyl, triazolyl, oxadiazolyl, pyridazinyl, pyrimidinyl, pyridinyl, isothiazolyl, thiazolyl, thiadiazolyl, benzimidazolyl, all of which are optionally substituted with one or more substituents independently selected from $R_6$, wherein $R_6$ consists of hydroxyl, $(C_1-C_4)$alkyl, $(C_1-C_4)$alkyloxy, $(C_3-C_6)$cycloalkyl and —$OR_x$, wherein $R_x$ is $(C_1-C_4)$alkyl.

Clause 13. A compound according to clause 10 wherein all of $R_1$, $R_2$, $R_3$, $R_4$ are hydrogen, n is 1, Q is —O—C(O)—$R_5$, wherein $R_5$ is a (4-6) membered heterocycloalkyl, optionally substituted with one or more substituents independently selected from $R_6$, wherein $R_6$ consists of hydroxyl, $(C_1-C_4)$alkyl, $(C_1-C_4)$alkyloxy, —$OR_x$, —C(O)$NR_aR_b$, —C(O)$OR_a$, —C(O)$R_a$, and $(C_3-C_6)$cycloalkyl, wherein $R_x$, $R_a$, $R_b$ are all $(C_1-C_4)$alkyl.

Clause 14. A compound according to clause 13 wherein all of $R_1$, $R_2$, $R_3$, $R_4$ are hydrogen, n is 1, Q is —O—C(O)—$R_5$, wherein $R_5$ is selected from the group consisting of pyrrolidinyl, piperidinyl, tetrahydrofuranyl, tetrahydropyranyl, azetidinyl, tetrahydrothiopyranyl, dioxothiolanyl and dioxothianyl, all of which are optionally substituted with —C(O)$NR_aR_b$, —C(O)$OR_a$, and —C(O)$R_a$, wherein $R_a$, $R_b$ are $(C_1-C_4)$alkyl.

Clause 15. A compound according to clause 1 or 2 wherein $R_1$ and $R_4$ are both hydrogen, one of $R_2$ and $R_3$ is hydrogen and the other one of $R_2$ and $R_3$ is $(C_1-C_4)$alkyl; n is 1, Q is —O—C(O)—$R_5$; wherein $R_5$ is a (4-6) membered heterocycloalkyl.

Clause 16. A compound according to clause 15 wherein $R_1$ and $R_4$ are both hydrogen, one of $R_2$ and $R_3$ is hydrogen and the other one of $R_2$ and $R_3$ is $(C_1-C_4)$alkyl; n is 1, Q is —O—C(O)—$R_5$; wherein $R_5$ is selected from the group consisting of tetrahydrofuranyl or tetrahydropyranyl.

Clause 17. A compound according to clause 1 or 2 wherein $R_1$ and $R_4$ are both hydrogen, $R_2$ and $R_3$ are both $(C_1-C_4)$alkyl; n is 1, Q is —O—C(O)—$R_5$; wherein $R_5$ is a (4-6) membered heterocycloalkyl.

Clause 18. A compound according to clause 17 wherein, $R_1$ and $R_4$ are both hydrogen, $R_2$ and $R_3$ are both $(C_1-C_4)$alkyl; n is 1, Q is —O—C(O)—$R_5$; wherein $R_5$ is selected from the group consisting of tetrahydrofuranyl or tetrahydropyranyl.

Clause 19. A compound according to clause 1 or 2 wherein all of $R_1$, $R_2$, $R_3$, $R_4$ are hydrogen, n is 2, Q is —O—C(O)—$R_5$; wherein $R_5$ is selected from the group consisting of a (5-6) membered heteroaryl and a (4-6) membered heterocycloalkyl, wherein said heteroaryl is optionally substituted with one or more of $(C_1-C_4)$alkyl.

Clause 20. A compound according to clause 19 wherein all of $R_1$, $R_2$, $R_3$, $R_4$ are hydrogen, n is 2, Q is —O—C(O)—$R_5$; wherein $R_5$ is a (5-6) membered heteroaryl optionally substituted with one or more of $(C_1-C_4)$alkyl.

Clause 21. A compound according to clause 20 wherein all of $R_1$, $R_2$, $R_3$, $R_4$ are hydrogen, n is 2, Q is —O—C(O)—$R_5$; wherein $R_5$ is selected from the group consisting of oxazolyl, isothiazolyl and thiazolyl, all of which are optionally substituted with one or more of $(C_1-C_4)$alkyl.

Clause 22. A compound according to clause 19 wherein all of $R_1$, $R_2$, $R_3$, $R_4$ are hydrogen, n is 2, Q is —O—C(O)—$R_5$; wherein $R_5$ is a (4-6) membered heterocycloalkyl.

Clause 23. A compound according to clause 22 wherein all of $R_1$, $R_2$, $R_3$, $R_4$ are hydrogen, n is 2, Q is —O—C(O)—$R_5$; wherein $R_5$ is tetrahydropyranyl.

Clause 24. A compound according to clause 1 or 2 wherein $R_1$ and $R_4$ are both hydrogen.

Clause 25. A compound according to clause 1 or 2 wherein one of $R_2$ and $R_3$ is hydrogen and the other one of $R_2$ and $R_3$ is $(C_1-C_4)$alkyl.

Clause 26. A compound according to clause 1 or 2 wherein $R_2$ and $R_3$ are both hydrogen.

Clause 27 A compound according to clause 1 or 2 wherein $R_2$ and $R_3$ are both $(C_1-C_4)$alkyl, e.g. both methyl.

Clause 28. A compound according to clause 1 or 2 wherein n is 0.

Clause 29. A compound according to clause 1 or 2 wherein n is 1.

Clause 30. A compound according to clause 1 or 2 wherein, n is 2.

Clause 31. A compound according to clause 1 or 2 wherein Q is —O—C(O)—$R_5$.

Clause 32. A compound according to clause 1 or 2 wherein Q is -O—C(O)—$(C_1-C_6)$alkyl-$R_5$.

Clause 33. A compound according to clause 1 or 2 wherein $R_5$ is heteroaryl optionally substituted with one or more substituents independently selected from $R_6$.

Clause 34. A compound according to clause 33 wherein $R_5$ is a (5-6) membered heteroaryl optionally substituted with one or more substituents independently selected from $R_6$.

Clause 35. A compound according to clause 33 wherein $R_5$ is a (9-10) membered heteroaryl optionally substituted with one or more substituents independently selected from $R_6$.

Clause 36. A compound according to clause 1 or 2 wherein $R_5$ is heterocycloalkyl optionally substituted with one or more substituents independently selected from $R_6$.

Clause 37. A compound according to clause 36 wherein $R_5$ is a (4-6) membered heterocycloalkyl optionally substituted with one or more substituents independently selected from $R_6$.

Clause 38. A compound according to clause 1 or 2 wherein $R_6$ consists of hydroxyl, $(C_1-C_4)$alkyl, $(C_1-C_4)$alkyloxy, —$OR_x$, —C(O)$NR_aR_b$, —C(O)$OR_a$, —C(O)$R_a$, and cycloalkyl, wherein all of $R_x$, $R_a$, $R_b$ are $(C_1-C_4)$alkyl.

Clause 39. A compound according to clause 38 wherein $R_6$ is hydroxyl.

Clause 40. A compound according to clause 38 wherein $R_6$ is $(C_1-C_4)$alkyl.

Clause 41. A compound according to clause 38 wherein $R_6$ is $(C_1-C_4)$alkyloxy.

Clause 42. A compound according to clause 38 wherein $R_6$ is —$OR_x$, wherein $R_x$ is $(C_1-C_4)$alkyl.

Clause 43. A compound according to clause 38 wherein $R_6$ is —C(O)$NR_aR_b$, wherein $R_a$, $R_b$ are $(C_1-C_4)$alkyl.

Clause 44. A compound according to clause 38 wherein $R_6$ is —C(O)$OR_a$, wherein $R_a$ is $(C_1-C_4)$alkyl.

Clause 45. A compound according to clause 38 wherein $R_6$ is C(O)$R_a$, wherein $R_a$ is $(C_1-C_4)$alkyl.

Clause 46. A compound according to clause 38 wherein $R_6$ is $(C_3-C_6)$cycloalkyl.

Clause 47. A compound according to any of the preceding clauses selected from the group consisting of 2-(3-ethyl-4-oxo-spiro[6,8-dihydro-5H-pyrazolo[4,3-c]azepine-7,4'-tetrahydropyran]-1-yl)ethyl isoxazole-5-carboxylate;

2-(3-ethyl-4-oxo-spiro[6,8-dihydro-5H-pyrazolo[4,3-c]azepine-7,4'-tetrahydropyran]-1-yl)ethyl oxazole-4-carboxylate;

2-(3-ethyl-4-oxo-spiro[6,8-dihydro-5H-pyrazolo[4,3-c]azepine-7,4'-tetrahydropyran]-1-yl)ethyl 1-methylpyrazole-4-carboxylate;

2-(3-ethyl-4-oxo-spiro[6,8-dihydro-5H-pyrazolo[4,3-c]azepine-7,4'-tetrahydropyran]-1-yl)ethyl 5-methylisoxazole-3-carboxylate;

2-(3-ethyl-4-oxo-spiro[6,8-dihydro-5H-pyrazolo[4,3-c]
azepine-7,4'-tetrahydropyran]-1-yl)ethyl 2-methyloxazole-4-carboxylate;
2-(3-ethyl-4-oxo-spiro[6,8-dihydro-5H-pyrazolo[4,3-c]
azepine-7,4'-tetrahydropyran]-1-yl)ethyl 2-methyloxazole-5-carboxylate;
2-(3-ethyl-4-oxo-spiro[6,8-dihydro-5H-pyrazolo[4,3-c]
azepine-7,4'-tetrahydropyran]-1-yl)ethyl thiazole-4-carboxylate;
2-(3-ethyl-4-oxo-spiro[6,8-dihydro-5H-pyrazolo[4,3-c]
azepine-7,4'-tetrahydropyran]-1-yl)ethyl tetrahydropyran-4-carboxylate;
2-(3-ethyl-4-oxo-spiro[6,8-dihydro-5H-pyrazolo[4,3-c]
azepine-7,4'-tetrahydropyran]-1-yl)ethyl 2-(1-methylpyrrol-2-yl)acetate;
2-(3-ethyl-4-oxo-spiro[6,8-dihydro-5H-pyrazolo[4,3-c]
azepine-7,4'-tetrahydropyran]-1-yl)ethyl 1,5-dimethylpyrazole-3-carboxylate;
2-(3-ethyl-4-oxo-spiro[6,8-dihydro-5H-pyrazolo[4,3-c]
azepine-7,4'-tetrahydropyran]-1-yl)ethyl 2-(5-methylisoxazol-3-yl)acetate;
2-(3-ethyl-4-oxo-spiro[6,8-dihydro-5H-pyrazolo[4,3-c]
azepine-7,4'-tetrahydropyran]-1-yl)ethyl 2-(3-methylisoxazol-5-yl)acetate;
2-(3-ethyl-4-oxo-spiro[6,8-dihydro-5H-pyrazolo[4,3-c]
azepine-7,4'-tetrahydropyran]-1-yl)ethyl 3-methylisothiazole-5-carboxylate;
2-(3-ethyl-4-oxo-spiro[6,8-dihydro-5H-pyrazolo[4,3-c]
azepine-7,4'-tetrahydropyran]-1-yl)ethyl 4-methylthiazole-2-carboxylate;
2-(3-ethyl-4-oxo-spiro[6,8-dihydro-5H-pyrazolo[4,3-c]
azepine-7,4'-tetrahydropyran]-1-yl)ethyl 2-(2-methylthiazol-4-yl)acetate;
2-(3-ethyl-4-oxo-spiro[6,8-dihydro-5H-pyrazolo[4,3-c]
azepine-7,4'-tetrahydropyran]-1-yl)ethyl 1-acetylpiperidine-4-carboxylate; or
a pharmaceutically acceptable salt, hydrate or solvate thereof.

Clause 48. A compound according to any of the preceding clauses 1-46 selected from the group consisting of
3-(3-ethyl-4-oxo-spiro[6,8-dihydro-5H-pyrazolo[4,3-c]
azepine-7,4'-tetrahydropyran]-1-yl)propyl 1H-imidazole-4-carboxylate;
3-(3-ethyl-4-oxo-spiro[6,8-dihydro-5H-pyrazolo[4,3-c]
azepine-7,4'-tetrahydropyran]-1-yl)propyl 1H-pyrazole-3-carboxylate;
3-(3-ethyl-4-oxo-spiro[6,8-dihydro-5H-pyrazolo[4,3-c]
azepine-7,4'-tetrahydropyran]-1-yl)propyl 1H-imidazole-2-carboxylate;
3-(3-ethyl-4-oxo-spiro[6,8-dihydro-5H-pyrazolo[4,3-c]
azepine-7,4'-tetrahydropyran]-1-yl)propyl 1H-pyrazole-4-carboxylate;
3-(3-ethyl-4-oxo-spiro[6,8-dihydro-5H-pyrazolo[4,3-c]
azepine-7,4'-tetrahydropyran]-1-yl)propyl isoxazole-3-carboxylate;
3-(3-ethyl-4-oxo-spiro[6,8-dihydro-5H-pyrazolo[4,3-c]
azepine-7,4'-tetrahydropyran]-1-yl)propyl isoxazole-5-carboxylate;
3-(3-ethyl-4-oxo-spiro[6,8-dihydro-5H-pyrazolo[4,3-c]
azepine-7,4'-tetrahydropyran]-1-yl)propyl oxazole-4-carboxylate;
3-(3-ethyl-4-oxo-spiro[6,8-dihydro-5H-pyrazolo[4,3-c]
azepine-7,4'-tetrahydropyran]-1-yl)propyl oxazole-5-carboxylate;
3-(3-ethyl-4-oxo-spiro[6,8-dihydro-5H-pyrazolo[4,3-c]
azepine-7,4'-tetrahydropyran]-1-yl)propyl 1H-triazole-4-carboxylate;
3-(3-ethyl-4-oxo-spiro[6,8-dihydro-5H-pyrazolo[4,3-c]
azepine-7,4'-tetrahydropyran]-1-yl)propyl 1H-1,2,4-triazole-3-carboxylate;
3-(3-ethyl-4-oxo-spiro[6,8-dihydro-5H-pyrazolo[4,3-c]
azepine-7,4'-tetrahydropyran]-1-yl)propyl 1,2,5-oxadiazole-3-carboxylate;
3-(3-ethyl-4-oxo-spiro[6,8-dihydro-5H-pyrazolo[4,3-c]
azepine-7,4'-tetrahydropyran]-1-yl)propyl tetrahydrofuran-3-carboxylate;
3-(3-ethyl-4-oxo-spiro[6,8-dihydro-5H-pyrazolo[4,3-c]
azepine-7,4'-tetrahydropyran]-1-yl)propyl pyridazine-3-carboxylate;
3-(3-ethyl-4-oxo-spiro[6,8-dihydro-5H-pyrazolo[4,3-c]
azepine-7,4'-tetrahydropyran]-1-yl)propyl pyridazine-4-carboxylate;
3-(3-ethyl-4-oxo-spiro[6,8-dihydro-5H-pyrazolo[4,3-c]
azepine-7,4'-tetrahydropyran]-1-yl)propyl pyrimidine-2-carboxylate;
3-(3-ethyl-4-oxo-spiro[6,8-dihydro-5H-pyrazolo[4,3-c]
azepine-7,4'-tetrahydropyran]-1-yl)propyl 1-methylpyrazole-3-carboxylate;
3-(3-ethyl-4-oxo-spiro[6,8-dihydro-5H-pyrazolo[4,3-c]
azepine-7,4'-tetrahydropyran]-1-yl)propyl 5-methyl-1H-pyrazole-3-carboxylate;
3-(3-ethyl-4-oxo-spiro[6,8-dihydro-5H-pyrazolo[4,3-c]
azepine-7,4'-tetrahydropyran]-1-yl)propyl 3-methyl-1H-pyrazole-5-carboxylate;
3-(3-ethyl-4-oxo-spiro[6,8-dihydro-5H-pyrazolo[4,3-c]
azepine-7,4'-tetrahydropyran]-1-yl)propyl 2-methylpyrazole-3-carboxylate;
3-(3-ethyl-4-oxo-spiro[6,8-dihydro-5H-pyrazolo[4,3-c]
azepine-7,4'-tetrahydropyran]-1-yl)propyl 2-methyl-1H-imidazole-4-carboxylate;
3-(3-ethyl-4-oxo-spiro[6,8-dihydro-5H-pyrazolo[4,3-c]
azepine-7,4'-tetrahydropyran]-1-yl)propyl 2-methyl-1H-imidazole-5-carboxylate;
3-(3-ethyl-4-oxo-spiro[6,8-dihydro-5H-pyrazolo[4,3-c]
azepine-7,4'-tetrahydropyran]-1-yl)propyl 1-methylpyrazole-4-carboxylate;
3-(3-ethyl-4-oxo-spiro[6,8-dihydro-5H-pyrazolo[4,3-c]
azepine-7,4'-tetrahydropyran]-1-yl)propyl 1-methylimidazole-4-carboxylate;
3-(3-ethyl-4-oxo-spiro[6,8-dihydro-5H-pyrazolo[4,3-c]
azepine-7,4'-tetrahydropyran]-1-yl)propyl 1-methylimidazole-2-carboxylate;
3-(3-ethyl-4-oxo-spiro[6,8-dihydro-5H-pyrazolo[4,3-c]
azepine-7,4'-tetrahydropyran]-1-yl)propyl 3-methylimidazole-4-carboxylate;
3-(3-ethyl-4-oxo-spiro[6,8-dihydro-5H-pyrazolo[4,3-c]
azepine-7,4'-tetrahydropyran]-1-yl)propyl 4-methylisoxazole-5-carboxylate;
3-(3-ethyl-4-oxo-spiro[6,8-dihydro-5H-pyrazolo[4,3-c]
azepine-7,4'-tetrahydropyran]-1-yl)propyl 3-methylisoxazole-5-carboxylate;
3-(3-ethyl-4-oxo-spiro[6,8-dihydro-5H-pyrazolo[4,3-c]
azepine-7,4'-tetrahydropyran]-1-yl)propyl 5-methylisoxazole-3-carboxylate;
3-(3-ethyl-4-oxo-spiro[6,8-dihydro-5H-pyrazolo[4,3-c]
azepine-7,4'-tetrahydropyran]-1-yl)propyl 3-methylisoxazole-4-carboxylate;
3-(3-ethyl-4-oxo-spiro[6,8-dihydro-5H-pyrazolo[4,3-c]
azepine-7,4'-tetrahydropyran]-1-yl)propyl 2-methyloxazole-4-carboxylate;
3-(3-ethyl-4-oxo-spiro[6,8-dihydro-5H-pyrazolo[4,3-c]
azepine-7,4'-tetrahydropyran]-1-yl)propyl 4-methyloxazole-5-carboxylate;

3-(3-ethyl-4-oxo-spiro[6,8-dihydro-5H-pyrazolo[4,3-c]azepine-7,4'-tetrahydropyran]-1-yl)propyl 2-methyloxazole-5-carboxylate;

3-(3-ethyl-4-oxo-spiro[6,8-dihydro-5H-pyrazolo[4,3-c]azepine-7,4'-tetrahydropyran]-1-yl)propyl 3-methyltriazole-4-carboxylate;

3-(3-ethyl-4-oxo-spiro[6,8-dihydro-5H-pyrazolo[4,3-c]azepine-7,4'-tetrahydropyran]-1-yl)propyl 5-methyl-4H-1,2,4-triazole-3-carboxylate;

3-(3-ethyl-4-oxo-spiro[6,8-dihydro-5H-pyrazolo[4,3-c]azepine-7,4'-tetrahydropyran]-1-yl)propyl 4-methyl-1,2,5-oxadiazole-3-carboxylate;

3-(3-ethyl-4-oxo-spiro[6,8-dihydro-5H-pyrazolo[4,3-c]azepine-7,4'-tetrahydropyran]-1-yl)propyl 3-hydroxyisoxazole-5-carboxylate;

3-(3-ethyl-4-oxo-spiro[6,8-dihydro-5H-pyrazolo[4,3-c]azepine-7,4'-tetrahydropyran]-1-yl)propyl isothiazole-3-carboxylate;

3-(3-ethyl-4-oxo-spiro[6,8-dihydro-5H-pyrazolo[4,3-c]azepine-7,4'-tetrahydropyran]-1-yl)propyl isothiazole-5-carboxylate;

3-(3-ethyl-4-oxo-spiro[6,8-dihydro-5H-pyrazolo[4,3-c]azepine-7,4'-tetrahydropyran]-1-yl)propyl isothiazole-4-carboxylate;

3-(3-ethyl-4-oxo-spiro[6,8-dihydro-5H-pyrazolo[4,3-c]azepine-7,4'-tetrahydropyran]-1-yl)propyl thiazole-5-carboxylate;

3-(3-ethyl-4-oxo-spiro[6,8-dihydro-5H-pyrazolo[4,3-c]azepine-7,4'-tetrahydropyran]-1-yl)propyl thiadiazole-4-carboxylate;

3-(3-ethyl-4-oxo-spiro[6,8-dihydro-5H-pyrazolo[4,3-c]azepine-7,4'-tetrahydropyran]-1-yl)propyl tetrahydropyran-3-carboxylate;

3-(3-ethyl-4-oxo-spiro[6,8-dihydro-5H-pyrazolo[4,3-c]azepine-7,4'-tetrahydropyran]-1-yl)propyl tetrahydropyran-4-carboxylate;

3-(3-ethyl-4-oxo-spiro[6,8-dihydro-5H-pyrazolo[4,3-c]azepine-7,4'-tetrahydropyran]-1-yl)propyl tetrahydrothiophene-3-carboxylate;

3-(3-ethyl-4-oxo-spiro[6,8-dihydro-5H-pyrazolo[4,3-c]azepine-7,4'-tetrahydropyran]-1-yl)propyl 5-methylpyridine-2-carboxylate;

3-(3-ethyl-4-oxo-spiro[6,8-dihydro-5H-pyrazolo[4,3-c]azepine-7,4'-tetrahydropyran]-1-yl)propyl 3-methylpyridine-2-carboxylate;

3-(3-ethyl-4-oxo-spiro[6,8-dihydro-5H-pyrazolo[4,3-c]azepine-7,4'-tetrahydropyran]-1-yl)propyl 4-methylpyridine-2-carboxylate;

3-(3-ethyl-4-oxo-spiro[6,8-dihydro-5H-pyrazolo[4,3-c]azepine-7,4'-tetrahydropyran]-1-yl)propyl 6-methylpyridine-2-carboxylate;

3-(3-ethyl-4-oxo-spiro[6,8-dihydro-5H-pyrazolo[4,3-c]azepine-7,4'-tetrahydropyran]-1-yl)propyl 2-methylpyridine-3-carboxylate;

3-(3-ethyl-4-oxo-spiro[6,8-dihydro-5H-pyrazolo[4,3-c]azepine-7,4'-tetrahydropyran]-1-yl)propyl 5-methylpyrimidine-2-carboxylate;

3-(3-ethyl-4-oxo-spiro[6,8-dihydro-5H-pyrazolo[4,3-c]azepine-7,4'-tetrahydropyran]-1-yl)propyl 3-methylpyridazine-4-carboxylate;

3-(3-ethyl-4-oxo-spiro[6,8-dihydro-5H-pyrazolo[4,3-c]azepine-7,4'-tetrahydropyran]-1-yl)propyl 2-methylpyrimidine-4-carboxylate;

3-(3-ethyl-4-oxo-spiro[6,8-dihydro-5H-pyrazolo[4,3-c]azepine-7,4'-tetrahydropyran]-1-yl)propyl 4-methylpyrimidine-2-carboxylate;

3-(3-ethyl-4-oxo-spiro[6,8-dihydro-5H-pyrazolo[4,3-c]azepine-7,4'-tetrahydropyran]-1-yl)propyl 2-methylpyrimidine-5-carboxylate;

3-(3-ethyl-4-oxo-spiro[6,8-dihydro-5H-pyrazolo[4,3-c]azepine-7,4'-tetrahydropyran]-1-yl)propyl 2,5-dimethylpyrazole-3-carboxylate;

3-(3-ethyl-4-oxo-spiro[6,8-dihydro-5H-pyrazolo[4,3-c]azepine-7,4'-tetrahydropyran]-1-yl)propyl 1,5-dimethylpyrazole-3-carboxylate;

3-(3-ethyl-4-oxo-spiro[6,8-dihydro-5H-pyrazolo[4,3-c]azepine-7,4'-tetrahydropyran]-1-yl)propyl 2,3-dimethylimidazole-4-carboxylate;

3-(3-ethyl-4-oxo-spiro[6,8-dihydro-5H-pyrazolo[4,3-c]azepine-7,4'-tetrahydropyran]-1-yl)propyl 4,5-dimethylisoxazole-3-carboxylate;

3-(3-ethyl-4-oxo-spiro[6,8-dihydro-5H-pyrazolo[4,3-c]azepine-7,4'-tetrahydropyran]-1-yl)propyl 3,5-dimethylisoxazole-4-carboxylate;

3-(3-ethyl-4-oxo-spiro[6,8-dihydro-5H-pyrazolo[4,3-c]azepine-7,4'-tetrahydropyran]-1-yl)propyl 2,5-dimethyloxazole-4-carboxylate;

3-(3-ethyl-4-oxo-spiro[6,8-dihydro-5H-pyrazolo[4,3-c]azepine-7,4'-tetrahydropyran]-1-yl)propyl 1-acetylazetidine-3-carboxylate;

3-(3-ethyl-4-oxo-spiro[6,8-dihydro-5H-pyrazolo[4,3-c]azepine-7,4'-tetrahydropyran]-1-yl)propyl 3-methylisothiazole-5-carboxylate;

3-(3-ethyl-4-oxo-spiro[6,8-dihydro-5H-pyrazolo[4,3-c]azepine-7,4'-tetrahydropyran]-1-yl)propyl 5-methylisothiazole-4-carboxylate;

3-(3-ethyl-4-oxo-spiro[6,8-dihydro-5H-pyrazolo[4,3-c]azepine-7,4'-tetrahydropyran]-1-yl)propyl 5-methylthiazole-4-carboxylate;

3-(3-ethyl-4-oxo-spiro[6,8-dihydro-5H-pyrazolo[4,3-c]azepine-7,4'-tetrahydropyran]-1-yl)propyl 4-methylthiazole-5-carboxylate;

3-(3-ethyl-4-oxo-spiro[6,8-dihydro-5H-pyrazolo[4,3-c]azepine-7,4'-tetrahydropyran]-1-yl)propyl 2-methylthiazole-5-carboxylate;

3-(3-ethyl-4-oxo-spiro[6,8-dihydro-5H-pyrazolo[4,3-c]azepine-7,4'-tetrahydropyran]-1-yl)propyl 4-methylthiadiazole-5-carboxylate;

3-(3-ethyl-4-oxo-spiro[6,8-dihydro-5H-pyrazolo[4,3-c]azepine-7,4'-tetrahydropyran]-1-yl)propyl tetrahydrothiopyran-3-carboxylate;

3-(3-ethyl-4-oxo-spiro[6,8-dihydro-5H-pyrazolo[4,3-c]azepine-7,4'-tetrahydropyran]-1-yl)propyl tetrahydrothiopyran-4-carboxylate;

3-(3-ethyl-4-oxo-spiro[6,8-dihydro-5H-pyrazolo[4,3-c]azepine-7,4'-tetrahydropyran]-1-yl)propyl 2,6-dimethylpyridine-4-carboxylate;

3-(3-ethyl-4-oxo-spiro[6,8-dihydro-5H-pyrazolo[4,3-c]azepine-7,4'-tetrahydropyran]-1-yl)propyl 2,6-dimethylpyridine-3-carboxylate;

3-(3-ethyl-4-oxo-spiro[6,8-dihydro-5H-pyrazolo[4,3-c]azepine-7,4'-tetrahydropyran]-1-yl)propyl 3,6-dimethylpyridazine-4-carboxylate;

3-(3-ethyl-4-oxo-spiro[6,8-dihydro-5H-pyrazolo[4,3-c]azepine-7,4'-tetrahydropyran]-1-yl) propyl 2-cyclopropyloxazole-4-carboxylate;

3-(3-ethyl-4-oxo-spiro[6,8-dihydro-5H-pyrazolo[4,3-c]azepine-7,4'-tetrahydropyran]-1-yl)propyl 2-ethyl-5-methyl-pyrazole-3-carboxylate;

3-(3-ethyl-4-oxo-spiro[6,8-dihydro-5H-pyrazolo[4,3-c]azepine-7,4'-tetrahydropyran]-1-yl)propyl 1,3,5-trimethylpyrazole-4-carboxylate;

3-(3-ethyl-4-oxo-spiro[6,8-dihydro-5H-pyrazolo[4,3-c]azepine-7,4'-tetrahydropyran]-1-yl)propyl 3-ethyl-5-methyl-isoxazole-4-carboxylate;

3-(3-ethyl-4-oxo-spiro[6,8-dihydro-5H-pyrazolo[4,3-c]azepine-7,4'-tetrahydropyran]-1-yl)propyl 1-acetylpyrrolidine-3-carboxylate;

3-(3-ethyl-4-oxo-spiro[6,8-dihydro-5H-pyrazolo[4,3-c]azepine-7,4'-tetrahydropyran]-1-yl)propyl 4,5-dimethyl-thiazole-2-carboxylate;

3-(3-ethyl-4-oxo-spiro[6,8-dihydro-5H-pyrazolo[4,3-c]azepine-7,4'-tetrahydropyran]-1-yl)propyl 2,4-dimethyl-thiazole-5-carboxylate;

3-(3-ethyl-4-oxo-spiro[6,8-dihydro-5H-pyrazolo[4,3-c]azepine-7,4'-tetrahydropyran]-1-yl)propyl 1,1-dioxothiolane-3-carboxylate;

3-(3-ethyl-4-oxo-spiro[6,8-dihydro-5H-pyrazolo[4,3-c]azepine-7,4'-tetrahydropyran]-1-yl)propyl 3,5-diethyl-isoxazole-4-carboxylate;

3-(3-ethyl-4-oxo-spiro[6,8-dihydro-5H-pyrazolo[4,3-c]azepine-7,4'-tetrahydropyran]-1-yl)propyl 1-acetylpiperidine-3-carboxylate;

3-(3-ethyl-4-oxo-spiro[6,8-dihydro-5H-pyrazolo[4,3-c]azepine-7,4'-tetrahydropyran]-1-yl)propyl 1-acetylpiperidine-4-carboxylate;

3-(3-ethyl-4-oxo-spiro[6,8-dihydro-5H-pyrazolo[4,3-c]azepine-7,4'-tetrahydropyran]-1-yl)propyl 2-methoxy-4-methyl-thiazole-5-carboxylate;

3-(3-ethyl-4-oxo-spiro[6,8-dihydro-5H-pyrazolo[4,3-c]azepine-7,4'-tetrahydropyran]-1-yl)propyl 3-methylbenzimidazole-5-carboxylate;

3-(3-ethyl-4-oxo-spiro[6,8-dihydro-5H-pyrazolo[4,3-c]azepine-7,4'-tetrahydropyran]-1-yl)propyl 1,1-dioxothiane-3-carboxylate;

3-(3-ethyl-4-oxo-spiro[6,8-dihydro-5H-pyrazolo[4,3-c]azepine-7,4'-tetrahydropyran]-1-yl)propyl 1,1-dioxothiane-4-carboxylate;

O3-[3-(3-ethyl-4-oxo-spiro[6,8-dihydro-5H-pyrazolo[4,3-c]azepine-7,4'-tetrahydropyran]-1-yl)propyl] O1-methyl piperidine-1,3-dicarboxylate;

O4-[3-(3-ethyl-4-oxo-spiro[6,8-dihydro-5H-pyrazolo[4,3-c]azepine-7,4'-tetrahydropyran]-1-yl)propyl] O1-methyl piperidine-1,4-dicarboxylate;

3-(3-ethyl-4-oxo-spiro[6,8-dihydro-5H-pyrazolo[4,3-c]azepine-7,4'-tetrahydropyran]-1-yl)propyl 1-(dimethylcarbamoyl)piperidine-3-carboxylate;

3-(3-ethyl-4-oxo-spiro[6,8-dihydro-5H-pyrazolo[4,3-c]azepine-7,4'-tetrahydropyran]-1-yl)propyl 1-(dimethylcarbamoyl)piperidine-4-carboxylate; or a pharmaceutically acceptable salt, hydrate or solvate thereof.

Clause 49. A compound according to any of the preceding clauses 1-46 selected from the group consisting of

[(2R)-3-(3-ethyl-4-oxo-spiro[6,8-dihydro-5H-pyrazolo[4,3-c]azepine-7,4'-tetrahydropyran]-1-yl)-2-methyl-propyl] tetrahydrofuran-3-carboxylate;

[(2R)-3-(3-ethyl-4-oxo-spiro[6,8-dihydro-5H-pyrazolo[4,3-c]azepine-7,4'-tetrahydropyran]-1-yl)-2-methyl-propyl] tetrahydropyran-4-carboxylate; or a pharmaceutically acceptable salt, hydrate or solvate thereof.

Clause 50. A compound according to any of the preceding clauses 1-46 selected from the group consisting of

[3-(3-ethyl-4-oxo-spiro[6,8-dihydro-5H-pyrazolo[4,3-c]azepine-7,4'-tetrahydropyran]-1-yl)-2,2-dimethyl-propyl] tetrahydrofuran-3-carboxylate;

[3-(3-ethyl-4-oxo-spiro[6,8-dihydro-5H-pyrazolo[4,3-c]azepine-7,4'-tetrahydropyran]-1-yl)-2,2-dimethyl-propyl] tetrahydropyran-4-carboxylate; or a pharmaceutically acceptable salt, hydrate or solvate thereof.

Clause 51. A compound according to any of the preceding clauses 1-46 selected from the group consisting of 4-(3-ethyl-4-oxo-spiro[6,8-dihydro-5H-pyrazolo[4,3-c]azepine-7,4'-tetrahydropyran]-1-yl)butyl 2-methyloxazole-5-carboxylate;

4-(3-ethyl-4-oxo-spiro[6,8-dihydro-5H-pyrazolo[4,3-c]azepine-7,4'-tetrahydropyran]-1-yl)butyl isothiazole-4-carboxylate;

4-(3-ethyl-4-oxo-spiro[6,8-dihydro-5H-pyrazolo[4,3-c]azepine-7,4'-tetrahydropyran]-1-yl)butyl thiazole-4-carboxylate;

4-(3-ethyl-4-oxo-spiro[6,8-dihydro-5H-pyrazolo[4,3-c]azepine-7,4'-tetrahydropyran]-1-yl)butyl tetrahydropyran-4-carboxylate; or a pharmaceutically acceptable salt, hydrate or solvate thereof.

Clause 52. A pharmaceutical composition comprising a compound according to any one of clauses 1-51 together with a pharmaceutically acceptable vehicle or excipient or pharmaceutically acceptable carrier(s).

Clause 53. The pharmaceutical composition according to clause 52 further comprising one or more other therapeutically active compound(s).

Clause 54. A use of the compound according to any of the clauses 1-51, for the manufacture of a pharmaceutical composition.

Clause 55. The use of a compound according to clause 54 in the manufacture of a pharmaceutical composition for the treatment or amelioration of a disease, disorder or condition responsive to PDE4 inhibitory activity.

Clause 56. The use according to clause 55, wherein the disease, disorder or condition is dermal diseases or conditions.

Clause 57. The use according to clause 56, wherein the disease, disorder or condition is proliferative and inflammatory skin disorders, dermatitis, atopic dermatitis, seborrheic dermatitis, contact dermatitis, psoriasis, cancer, epidermal inflammation, alopecia, alopecia areata, skin atrophy, steroid induced skin atrophy, skin ageing, photo skin ageing, acne, urticaria, pruritis, and eczema.

Clause 58. The compound according to any of the clauses 1-51, for use as a medicament.

Clause 59. The compound according to clause 58 for use in the treatment or amelioration of a disease, disorder or condition responsive to PDE4 inhibitory activity.

Clause 60. The compound according to clause 59 for use in the treatment or amelioration of dermal diseases or conditions.

Clause 61. The compound according to clause 60 for use in the treatment of proliferative and inflammatory skin disorders, dermatitis, atopic dermatitis, seborrheic dermatitis, contact dermatitis, psoriasis, cancer, epidermal inflammation, alopecia, alopecia areata, skin atrophy, steroid induced skin atrophy, skin ageing, photo skin ageing, acne, urticaria, pruritis, and eczema.

Clause 62. A method for treatment or alleviation of a disease or a disorder or a condition responsive to PDE4 inhibitory activity, which method comprises the step of administering to a living animal body a therapeutically effective amount of a compound according to any of the clauses 1-51.

Clause 63. A method of treating or ameliorating dermal diseases or conditions, the method comprising administering to a person suffering from at least one of said diseases an effective amount of one or more compounds according to according to any one of clauses 1-51, optionally together with a pharmaceutically acceptable carrier or one or more excipients, optionally in combination with other therapeutically active compounds.

Clause 64. The method according to clause 62, wherein the dermal disease or condition is selected from the group consisting of proliferative and inflammatory skin disorders, dermatitis, atopic dermatitis, seborrheic dermatitis, contact dermatitis, psoriasis, cancer, epidermal inflammation, alopecia, alopecia areata, skin atrophy, steroid induced skin atrophy, skin ageing, photo skin ageing, acne, urticaria, pruritis, and eczema.

Clause 65. An intermediate compound

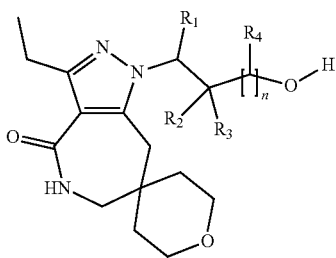

wherein $R_1$, $R_2$, $R_3$, $R_4$, and n are as defined in clause 1.

*** indicates that $IC_{50}$ values are <100 nM

The Examples 1-16 shown in Table 1 were prepared by reacting Compound 009 as described in General Procedure 1 with the appropriate acid:

The Examples 17-107 shown in Table 2 were prepared by reacting Compound 014 as described in General Procedure 1 with the appropriate acid:

The Examples 108-109 shown in Table 3 were prepared by reacting Compound 021 as described in General Procedure 2 with the appropriate acid:

The Examples 110-111 shown in Table 4 were prepared by reacting Compound 028 as described in General Procedure 2 with the appropriate acid:

The Examples 112-115 shown in Table 5 were prepared by reacting Compound 031 as described in General Procedure 2 with the appropriate acid:

Clauses

In view of the description the present inventors have in particular provided:

Clause 1. A compound of general formula (I)

wherein $R_1$ and $R_4$ are independently selected from the group consisting of hydrogen and $(C_1-C_4)$alkyl;

The invention claimed is:
1. A compound of general formula (I)

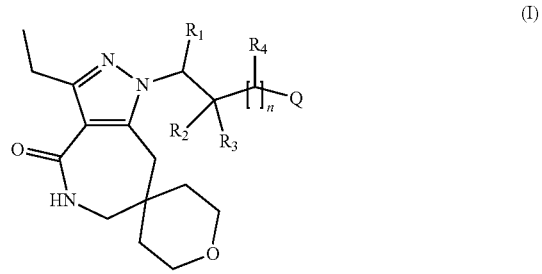

wherein
$R_1$ and $R_4$ are independently selected from the group consisting of hydrogen and $(C_1-C_4)$alkyl;
$R_2$ and $R_3$ are independently selected from the group consisting of hydrogen and $(C_1-C_4)$alkyl; or $R_2$ and $R_3$ together with the carbon atom to which they are attached form a cyclopropyl, cyclobutyl, cyclopentyl, oxetanyl, tetrahydrofuranyl, or tetrahydropyranyl ring;
n=0, 1 or 2; and when n is 0, $R_4$ does not exist;
Q is selected from the group consisting of —O—C(O)—$R_5$ and —O—C(O)—$(C_1-C_6)$alkyl-$R_5$;
$R_5$ is selected from the group consisting of heteroaryl and heterocycloalkyl, wherein said heteroaryl and heterocycloalkyl are optionally substituted with one or more substituents independently selected from $R_6$;
$R_6$ consists of halogen, cyano, hydroxyl, $(C_1-C_4)$alkyl, halo$(C_1-C_4)$alkyl, $(C_1-C_4)$-alkyloxy, —S(O)$_2R_x$, —S(O)$_2NR_aR_b$, —$OR_x$, —C(O)$NR_aR_b$, —C(O)$OR_a$, —C(O)$R_a$, cycloalkyl, aryl and heteroaryl;
$R_x$ is $(C_1-C_4)$alkyl;
$R_a$ and $R_b$ are independently selected from the group consisting of hydrogen, $(C_1-C_4)$alkyl, phenyl-$(C_1-C_4)$alkyl, or
$R_a$ and $R_b$ together with the nitrogen to which they are attached form a 4-6 membered heterocycloalkyl, wherein said heterocycloalkyl is optionally substituted with one or more $(C_1-C_4)$alkyl;
or a pharmaceutically acceptable salt, hydrate or solvate thereof.

2. A compound according to claim 1 wherein each of $R_1$, $R_2$, and $R_3$ is hydrogen, n is 0, Q is selected from the group consisting of —O—C(O)—$R_5$ and —O—C(O)—$(C_1-C_6)$alkyl-$R_5$;
wherein $R_5$ is selected from the group consisting of a (5-6) membered heteroaryl, and a (4-6) membered heterocycloalkyl, and
wherein said heteroaryl and heterocycloalkyl are optionally substituted with one or more substituents independently selected from $(C_1-C_4)$alkyl, $(C_1-C_4)$-alkyloxy, —C(O)$R_a$, $(C_3-C_6)$cycloalkyl; wherein $R_a$ is $(C_1-C_4)$alkyl.

3. A compound according to claim 1 wherein each of $R_1$, $R_2$, $R_3$, and $R_4$ is hydrogen, n is 1, Q is —O—C(O)—$R_5$;
wherein $R_5$ is selected from the group consisting of a (5-6) membered heteroaryl, a (9-10) membered heteroaryl and a (4-6) membered heterocycloalkyl,
wherein said heteroaryl and heterocycloalkyl are optionally substituted with one or more substituents independently selected from $R_6$; and
wherein $R_6$ consists of hydroxyl, $(C_1-C_4)$alkyl, $(C_1-C_4)$alkyloxy, —$OR_x$, —C(O)$NR_aR_b$, —C(O)$OR_a$, —C(O)$R_a$, and $(C_3-C_6)$cycloalkyl, and $R_x$, $R_a$, $R_b$ are all $(C_1-C_4)$alkyl.

4. A compound according to claim 1 wherein $R_1$ and $R_4$ are both hydrogen, one of $R_2$ and $R_3$ is hydrogen and the other one of $R_2$ and $R_3$ is $(C_1-C_4)$alkyl; n is 1, Q is —O—C(O)—$R_5$; wherein $R_5$ is a (4-6) membered heterocycloalkyl.

5. A compound according to claim 1 wherein $R_1$ and $R_4$ are both hydrogen, $R_2$ and $R_3$ are both $(C_1-C_4)$alkyl; n is 1, Q is —O—C(O)—$R_5$; wherein $R_5$ is a (4-6) membered heterocycloalkyl.

6. A compound according to claim 1 wherein each of $R_1$, $R_2$, $R_3$, $R_4$ is hydrogen, n is 2, Q is —O—C(O)—$R_5$;
  wherein $R_5$ is selected from the group consisting of a (5-6) membered heteroaryl and a (4-6) membered heterocycloalkyl, and
  wherein said heteroaryl is optionally substituted with one or more of $(C_1-C_4)$alkyl.

7. A compound according to claim 1 selected from the group consisting of
  (i) 2-(3-ethyl-4-oxo-spiro[6,8-dihydro-5H-pyrazolo[4,3-c]azepine-7,4'-tetrahydropyran]-1-yl)ethyl isoxazole-5-carboxylate;
  (ii) 2-(3-ethyl-4-oxo-spiro[6,8-dihydro-5H-pyrazolo[4,3-c]azepine-7,4'-tetrahydropyran]-1-yl)ethyl oxazole-4-carboxylate;
  (iii) 2-(3-ethyl-4-oxo-spiro[6,8-dihydro-5H-pyrazolo[4,3-c]azepine-7,4'-tetrahydropyran]-1-yl)ethyl 1-methylpyrazole-4-carboxylate;
  (iv) 2-(3-ethyl-4-oxo-spiro[6,8-dihydro-5H-pyrazolo[4,3-c]azepine-7,4'-tetrahydropyran]-1-yl)ethyl 5-methylisoxazole-3-carboxylate;
  (v) 2-(3-ethyl-4-oxo-spiro[6,8-dihydro-5H-pyrazolo[4,3-c]azepine-7,4'-tetrahydropyran]-1-yl)ethyl 2-methyloxazole-4-carboxylate;
  (vi) 2-(3-ethyl-4-oxo-spiro[6,8-dihydro-5H-pyrazolo[4,3-c]azepine-7,4'-tetrahydropyran]-1-yl)ethyl 2-methyloxazole-5-carboxylate;
  (vii) 2-(3-ethyl-4-oxo-spiro[6,8-dihydro-5H-pyrazolo[4,3-c]azepine-7,4'-tetrahydropyran]-1-yl)ethyl thiazole-4-carboxylate;
  (viii) 2-(3-ethyl-4-oxo-spiro[6,8-dihydro-5H-pyrazolo[4,3-c]azepine-7,4'-tetrahydropyran]-1-yl)ethyl tetrahydropyran-4-carboxylate;
  (ix) 2-(3-ethyl-4-oxo-spiro[6,8-dihydro-5H-pyrazolo[4,3-c]azepine-7,4'-tetrahydropyran]-1-yl)ethyl 2-(1-methylpyrrol-2-yl)acetate;
  (x) 2-(3-ethyl-4-oxo-spiro[6,8-dihydro-5H-pyrazolo[4,3-c]azepine-7,4'-tetrahydropyran]-1-yl)ethyl 1,5-dimethylpyrazole-3-carboxylate;
  (xi) 2-(3-ethyl-4-oxo-spiro[6,8-dihydro-5H-pyrazolo[4,3-c]azepine-7,4'-tetrahydropyran]-1-yl)ethyl 2-(5-methylisoxazol-3-yl)acetate;
  (xii) 2-(3-ethyl-4-oxo-spiro[6,8-dihydro-5H-pyrazolo[4,3-c]azepine-7,4'-tetrahydropyran]-1-yl)ethyl 2-(3-methylisoxazol-5-yl)acetate;
  (xiii) 2-(3-ethyl-4-oxo-spiro[6,8-dihydro-5H-pyrazolo[4,3-c]azepine-7,4'-tetrahydropyran]-1-yl)ethyl 3-methylisothiazole-5-carboxylate;
  (xiv) 2-(3-ethyl-4-oxo-spiro[6,8-dihydro-5H-pyrazolo[4,3-c]azepine-7,4'-tetrahydropyran]-1-yl)ethyl 4-methylthiazole-2-carboxylate;
  (xv) 2-(3-ethyl-4-oxo-spiro[6,8-dihydro-5H-pyrazolo[4,3-c]azepine-7,4'-tetrahydropyran]-1-yl)ethyl 2-(2-methylthiazol-4-yl)acetate;
  (xvi) 2-(3-ethyl-4-oxo-spiro[6,8-dihydro-5H-pyrazolo[4,3-c]azepine-7,4'-tetrahydropyran]-1-yl)ethyl 1-acetylpiperidine-4-carboxylate;
  (xvii) 3-(3-ethyl-4-oxo-spiro[6,8-dihydro-5H-pyrazolo[4,3-c]azepine-7,4'-tetrahydropyran]-1-yl)propyl 1H-imidazole-4-carboxylate;
  (xviii) 3-(3-ethyl-4-oxo-spiro[6,8-dihydro-5H-pyrazolo[4,3-c]azepine-7,4'-tetrahydropyran]-1-yl)propyl 1H-pyrazole-3-carboxylate;
  (xix) 3-(3-ethyl-4-oxo-spiro[6,8-dihydro-5H-pyrazolo[4,3-c]azepine-7,4'-tetrahydropyran]-1-yl)propyl 1H-imidazole-2-carboxylate;
  (xx) 3-(3-ethyl-4-oxo-spiro[6,8-dihydro-5H-pyrazolo[4,3-c]azepine-7,4'-tetrahydropyran]-1-yl)propyl 1H-pyrazole-4-carboxylate;
  (xxi) 3-(3-ethyl-4-oxo-spiro[6,8-dihydro-5H-pyrazolo[4,3-c]azepine-7,4'-tetrahydropyran]-1-yl)propyl isoxazole-3-carboxylate;
  (xxii) 3-(3-ethyl-4-oxo-spiro[6,8-dihydro-5H-pyrazolo[4,3-c]azepine-7,4'-tetrahydropyran]-1-yl)propyl isoxazole-5-carboxylate;
  (xxiii) 3-(3-ethyl-4-oxo-spiro[6,8-dihydro-5H-pyrazolo[4,3-c]azepine-7,4'-tetrahydropyran]-1-yl)propyl oxazole-4-carboxylate;
  (xxiv) 3-(3-ethyl-4-oxo-spiro[6,8-dihydro-5H-pyrazolo[4,3-c]azepine-7,4'-tetrahydropyran]-1-yl)propyl oxazole-5-carboxylate;
  (xxv) 3-(3-ethyl-4-oxo-spiro[6,8-dihydro-5H-pyrazolo[4,3-c]azepine-7,4'-tetrahydropyran]-1-yl)propyl 1H-triazole-4-carboxylate;
  (xxvi) 3-(3-ethyl-4-oxo-spiro[6,8-dihydro-5H-pyrazolo[4,3-c]azepine-7,4'-tetrahydropyran]-1-yl)propyl 1H-1,2,4-triazole-3-carboxylate;
  (xxvii) 3-(3-ethyl-4-oxo-spiro[6,8-dihydro-5H-pyrazolo[4,3-c]azepine-7,4'-tetrahydropyran]-1-yl)propyl 1,2,5-oxadiazole-3-carboxylate;
  (xxviii) 3-(3-ethyl-4-oxo-spiro[6,8-dihydro-5H-pyrazolo[4,3-c]azepine-7,4'-tetrahydropyran]-1-yl)propyl tetrahydrofuran-3-carboxylate;
  (xxix) 3-(3-ethyl-4-oxo-spiro[6,8-dihydro-5H-pyrazolo[4,3-c]azepine-7,4'-tetrahydropyran]-1-yl)propyl pyridazine-3-carboxylate;
  (xxx) 3-(3-ethyl-4-oxo-spiro[6,8-dihydro-5H-pyrazolo[4,3-c]azepine-7,4'-tetrahydropyran]-1-yl)propyl pyridazine-4-carboxylate;
  (xxxi) 3-(3-ethyl-4-oxo-spiro[6,8-dihydro-5H-pyrazolo[4,3-c]azepine-7,4'-tetrahydropyran]-1-yl)propyl pyrimidine-2-carboxylate;
  (xxxii) 3-(3-ethyl-4-oxo-spiro[6,8-dihydro-5H-pyrazolo[4,3-c]azepine-7,4'-tetrahydropyran]-1-yl)propyl 1-methylpyrazole-3-carboxylate;
  (xxxiii) 3-(3-ethyl-4-oxo-spiro[6,8-dihydro-5H-pyrazolo[4,3-c]azepine-7,4'-tetrahydropyran]-1-yl)propyl 5-methyl-1H-pyrazole-3-carboxylate;
  (xxxiv) 3-(3-ethyl-4-oxo-spiro[6,8-dihydro-5H-pyrazolo[4,3-c]azepine-7,4'-tetrahydropyran]-1-yl)propyl 3-methyl-1H-pyrazole-5-carboxylate;
  (xxxv) 3-(3-ethyl-4-oxo-spiro[6,8-dihydro-5H-pyrazolo[4,3-c]azepine-7,4'-tetrahydropyran]-1-yl)propyl 2-methylpyrazole-3-carboxylate;
  (xxxvi) 3-(3-ethyl-4-oxo-spiro[6,8-dihydro-5H-pyrazolo[4,3-c]azepine-7,4'-tetrahydropyran]-1-yl)propyl 2-methyl-1H-imidazole-4-carboxylate;
  (xxxvii) 3-(3-ethyl-4-oxo-spiro[6,8-dihydro-5H-pyrazolo[4,3-c]azepine-7,4'-tetrahydropyran]-1-yl)propyl 2-methyl-1H-imidazole-5-carboxylate;
  (xxxviii) 3-(3-ethyl-4-oxo-spiro[6,8-dihydro-5H-pyrazolo[4,3-c]azepine-7,4'-tetrahydropyran]-1-yl)propyl 1-methylpyrazole-4-carboxylate;

(xxxix) 3-(3-ethyl-4-oxo-spiro[6,8-dihydro-5H-pyrazolo[4,3-c]azepine-7,4'-tetrahydropyran]-1-yl)propyl 1-methylimidazole-4-carboxylate;

(xl) 3-(3-ethyl-4-oxo-spiro[6,8-dihydro-5H-pyrazolo[4,3-c]azepine-7,4'-tetrahydropyran]-1-yl)propyl 1-methylimidazole-2-carboxylate;

(xli) 3-(3-ethyl-4-oxo-spiro[6,8-dihydro-5H-pyrazolo[4,3-c]azepine-7,4'-tetrahydropyran]-1-yl)propyl 3-methylimidazole-4-carboxylate;

(xlii) 3-(3-ethyl-4-oxo-spiro[6,8-dihydro-5H-pyrazolo[4,3-c]azepine-7,4'-tetrahydropyran]-1-yl)propyl 4-methylisoxazole-5-carboxylate;

(xliii) 3-(3-ethyl-4-oxo-spiro[6,8-dihydro-5H-pyrazolo[4,3-c]azepine-7,4'-tetrahydropyran]-1-yl)propyl 3-methylisoxazole-5-carboxylate;

(xliv) 3-(3-ethyl-4-oxo-spiro[6,8-dihydro-5H-pyrazolo[4,3-c]azepine-7,4'-tetrahydropyran]-1-yl)propyl 5-methylisoxazole-3-carboxylate;

(xlv) 3-(3-ethyl-4-oxo-spiro[6,8-dihydro-5H-pyrazolo[4,3-c]azepine-7,4'-tetrahydropyran]-1-yl)propyl 3-methylisoxazole-4-carboxylate;

(xlvi) 3-(3-ethyl-4-oxo-spiro[6,8-dihydro-5H-pyrazolo[4,3-c]azepine-7,4'-tetrahydropyran]-1-yl)propyl 2-methyloxazole-4-carboxylate;

(xlvii) 3-(3-ethyl-4-oxo-spiro[6,8-dihydro-5H-pyrazolo[4,3-c]azepine-7,4'-tetrahydropyran]-1-yl)propyl 4-methyloxazole-5-carboxylate;

(xlviii) 3-(3-ethyl-4-oxo-spiro[6,8-dihydro-5H-pyrazolo[4,3-c]azepine-7,4'-tetrahydropyran]-1-yl)propyl 2-methyloxazole-5-carboxylate;

(xlix) 3-(3-ethyl-4-oxo-spiro[6,8-dihydro-5H-pyrazolo[4,3-c]azepine-7,4'-tetrahydropyran]-1-yl)propyl 3-methyltriazole-4-carboxylate;

(l) 3-(3-ethyl-4-oxo-spiro[6,8-dihydro-5H-pyrazolo[4,3-c]azepine-7,4'-tetrahydropyran]-1-yl)propyl 5-methyl-4H-1,2,4-triazole-3-carboxylate;

(li) 3-(3-ethyl-4-oxo-spiro[6,8-dihydro-5H-pyrazolo[4,3-c]azepine-7,4'-tetrahydropyran]-1-yl)propyl 4-methyl-1,2,5-oxadiazole-3-carboxylate;

(lii) 3-(3-ethyl-4-oxo-spiro[6,8-dihydro-5H-pyrazolo[4,3-c]azepine-7,4'-tetrahydropyran]-1-yl)propyl 3-hydroxyisoxazole-5-carboxylate;

(liii) 3-(3-ethyl-4-oxo-spiro[6,8-dihydro-5H-pyrazolo[4,3-c]azepine-7,4'-tetrahydropyran]-1-yl)propyl isothiazole-3-carboxylate;

(liv) 3-(3-ethyl-4-oxo-spiro[6,8-dihydro-5H-pyrazolo[4,3-c]azepine-7,4'-tetrahydropyran]-1-yl)propyl isothiazole-5-carboxylate;

(lv) 3-(3-ethyl-4-oxo-spiro[6,8-dihydro-5H-pyrazolo[4,3-c]azepine-7,4'-tetrahydropyran]-1-yl)propyl isothiazole-4-carboxylate;

(lvi) 3-(3-ethyl-4-oxo-spiro[6,8-dihydro-5H-pyrazolo[4,3-c]azepine-7,4'-tetrahydropyran]-1-yl)propyl thiazole-5-carboxylate;

(lvii) 3-(3-ethyl-4-oxo-spiro[6,8-dihydro-5H-pyrazolo[4,3-c]azepine-7,4'-tetrahydropyran]-1-yl)propyl thiadiazole-4-carboxylate;

(lviii) 3-(3-ethyl-4-oxo-spiro[6,8-dihydro-5H-pyrazolo[4,3-c]azepine-7,4'-tetrahydropyran]-1-yl)propyl tetrahydropyran-3-carboxylate;

(lix) 3-(3-ethyl-4-oxo-spiro[6,8-dihydro-5H-pyrazolo[4,3-c]azepine-7,4'-tetrahydropyran]-1-yl)propyl tetrahydropyran-4-carboxylate;

(lx) 3-(3-ethyl-4-oxo-spiro[6,8-dihydro-5H-pyrazolo[4,3-c]azepine-7,4'-tetrahydropyran]-1-yl)propyl tetrahydrothiophene-3-carboxylate;

(lxi) 3-(3-ethyl-4-oxo-spiro[6,8-dihydro-5H-pyrazolo[4,3-c]azepine-7,4'-tetrahydropyran]-1-yl)propyl 5-methylpyridine-2-carboxylate;

(lxii) 3-(3-ethyl-4-oxo-spiro[6,8-dihydro-5H-pyrazolo[4,3-c]azepine-7,4'-tetrahydropyran]-1-yl)propyl 3-methylpyridine-2-carboxylate;

(lxiii) 3-(3-ethyl-4-oxo-spiro[6,8-dihydro-5H-pyrazolo[4,3-c]azepine-7,4'-tetrahydropyran]-1-yl)propyl 4-methylpyridine-2-carboxylate;

(lxiv) 3-(3-ethyl-4-oxo-spiro[6,8-dihydro-5H-pyrazolo[4,3-c]azepine-7,4'-tetrahydropyran]-1-yl)propyl 6-methylpyridine-2-carboxylate;

(lxv) 3-(3-ethyl-4-oxo-spiro[6,8-dihydro-5H-pyrazolo[4,3-c]azepine-7,4'-tetrahydropyran]-1-yl)propyl 2-methylpyridine-3-carboxylate;

(lxvi) 3-(3-ethyl-4-oxo-spiro[6,8-dihydro-5H-pyrazolo[4,3-c]azepine-7,4'-tetrahydropyran]-1-yl)propyl 5-methylpyrimidine-2-carboxylate;

(lxvii) 3-(3-ethyl-4-oxo-spiro[6,8-dihydro-5H-pyrazolo[4,3-c]azepine-7,4'-tetrahydropyran]-1-yl)propyl 3-methylpyridazine-4-carboxylate;

(lxviii) 3-(3-ethyl-4-oxo-spiro[6,8-dihydro-5H-pyrazolo[4,3-c]azepine-7,4'-tetrahydropyran]-1-yl)propyl 2-methylpyrimidine-4-carboxylate;

(lxix) 3-(3-ethyl-4-oxo-spiro[6,8-dihydro-5H-pyrazolo[4,3-c]azepine-7,4'-tetrahydropyran]-1-yl)propyl 4-methylpyrimidine-2-carboxylate;

(lxx) 3-(3-ethyl-4-oxo-spiro[6,8-dihydro-5H-pyrazolo[4,3-c]azepine-7,4'-tetrahydropyran]-1-yl)propyl 2-methylpyrimidine-5-carboxylate;

(lxxi) 3-(3-ethyl-4-oxo-spiro[6,8-dihydro-5H-pyrazolo[4,3-c]azepine-7,4'-tetrahydropyran]-1-yl)propyl 2,5-dimethylpyrazole-3-carboxylate;

(lxxii) 3-(3-ethyl-4-oxo-spiro[6,8-dihydro-5H-pyrazolo[4,3-c]azepine-7,4'-tetrahydropyran]-1-yl)propyl 1,5-dimethylpyrazole-3-carboxylate;

(lxxiii) 3-(3-ethyl-4-oxo-spiro[6,8-dihydro-5H-pyrazolo[4,3-c]azepine-7,4'-tetrahydropyran]-1-yl)propyl 2,3-dimethylimidazole-4-carboxylate;

(lxxiv) 3-(3-ethyl-4-oxo-spiro[6,8-dihydro-5H-pyrazolo[4,3-c]azepine-7,4'-tetrahydropyran]-1-yl)propyl 4,5-dimethylisoxazole-3-carboxylate;

(lxxv) 3-(3-ethyl-4-oxo-spiro[6,8-dihydro-5H-pyrazolo[4,3-c]azepine-7,4'-tetrahydropyran]-1-yl)propyl 3,5-dimethylisoxazole-4-carboxylate;

(lxxvi) 3-(3-ethyl-4-oxo-spiro[6,8-dihydro-5H-pyrazolo[4,3-c]azepine-7,4'-tetrahydropyran]-1-yl)propyl 2,5-dimethyloxazole-4-carboxylate;

(lxxvii) 3-(3-ethyl-4-oxo-spiro[6,8-dihydro-5H-pyrazolo[4,3-c]azepine-7,4'-tetrahydropyran]-1-yl)propyl 1-acetylazetidine-3-carboxylate;

(lxxviii) 3-(3-ethyl-4-oxo-spiro[6,8-dihydro-5H-pyrazolo[4,3-c]azepine-7,4'-tetrahydropyran]-1-yl)propyl 3-methylisothiazole-5-carboxylate;

(lxxix) 3-(3-ethyl-4-oxo-spiro[6,8-dihydro-5H-pyrazolo[4,3-c]azepine-7,4'-tetrahydropyran]-1-yl)propyl 5-methylisothiazole-4-carboxylate;

(lxxx) 3-(3-ethyl-4-oxo-spiro[6,8-dihydro-5H-pyrazolo[4,3-c]azepine-7,4'-tetrahydropyran]-1-yl)propyl 5-methylthiazole-4-carboxylate;

(lxxxi) 3-(3-ethyl-4-oxo-spiro[6,8-dihydro-5H-pyrazolo[4,3-c]azepine-7,4'-tetrahydropyran]-1-yl)propyl 4-methylthiazole-5-carboxylate;

(lxxxii) 3-(3-ethyl-4-oxo-spiro[6,8-dihydro-5H-pyrazolo[4,3-c]azepine-7,4'-tetrahydropyran]-1-yl)propyl 2-methylthiazole-5-carboxylate;

(lxxxiii) 3-(3-ethyl-4-oxo-spiro[6,8-dihydro-5H-pyrazolo[4,3-c]azepine-7,4'-tetrahydropyran]-1-yl)propyl 4-methylthiadiazole-5-carboxylate;

(lxxxiv) 3-(3-ethyl-4-oxo-spiro[6,8-dihydro-5H-pyrazolo[4,3-c]azepine-7,4'-tetrahydropyran]-1-yl)propyl tetrahydrothiopyran-3-carboxylate;

(lxxxv) 3-(3-ethyl-4-oxo-spiro[6,8-dihydro-5H-pyrazolo[4,3-c]azepine-7,4'-tetrahydropyran]-1-yl)propyl tetrahydrothiopyran-4-carboxylate;

(lxxxvi) 3-(3-ethyl-4-oxo-spiro[6,8-dihydro-5H-pyrazolo[4,3-c]azepine-7,4'-tetrahydropyran]-1-yl)propyl 2,6-dimethylpyridine-4-carboxylate;

(lxxxvii) 3-(3-ethyl-4-oxo-spiro[6,8-dihydro-5H-pyrazolo[4,3-c]azepine-7,4'-tetrahydropyran]-1-yl)propyl 2,6-dimethylpyridine-3-carboxylate;

(lxxxviii) 3-(3-ethyl-4-oxo-spiro[6,8-dihydro-5H-pyrazolo[4,3-c]azepine-7,4'-tetrahydropyran]-1-yl)propyl 3,6-dimethylpyridazine-4-carboxylate;

(lxxxix) 3-(3-ethyl-4-oxo-spiro[6,8-dihydro-5H-pyrazolo[4,3-c]azepine-7,4'-tetrahydropyran]-1-yl)propyl 2-cyclopropyloxazole-4-carboxylate;

(xc) 3-(3-ethyl-4-oxo-spiro[6,8-dihydro-5H-pyrazolo[4,3-c]azepine-7,4'-tetrahydropyran]-1-yl)propyl 2-ethyl-5-methyl-pyrazole-3-carboxylate;

(xci) 3-(3-ethyl-4-oxo-spiro[6,8-dihydro-5H-pyrazolo[4,3-c]azepine-7,4'-tetrahydropyran]-1-yl)propyl 1,3,5-trimethylpyrazole-4-carboxylate;

(xcii) 3-(3-ethyl-4-oxo-spiro[6,8-dihydro-5H-pyrazolo[4,3-c]azepine-7,4'-tetrahydropyran]-1-yl)propyl 3-ethyl-5-methyl-isoxazole-4-carboxylate;

(xciii) 3-(3-ethyl-4-oxo-spiro[6,8-dihydro-5H-pyrazolo[4,3-c]azepine-7,4'-tetrahydropyran]-1-yl)propyl 1-acetylpyrrolidine-3-carboxylate;

(xciv) 3-(3-ethyl-4-oxo-spiro[6,8-dihydro-5H-pyrazolo[4,3-c]azepine-7,4'-tetrahydropyran]-1-yl)propyl 4,5-dimethylthiazole-2-carboxylate;

(xcv) 3-(3-ethyl-4-oxo-spiro[6,8-dihydro-5H-pyrazolo[4,3-c]azepine-7,4'-tetrahydropyran]-1-yl)propyl 2,4-dimethylthiazole-5-carboxylate;

(xcvi) 3-(3-ethyl-4-oxo-spiro[6,8-dihydro-5H-pyrazolo[4,3-c]azepine-7,4'-tetrahydropyran]-1-yl)propyl 1,1-dioxothiolane-3-carboxylate;

(xcvii) 3-(3-ethyl-4-oxo-spiro[6,8-dihydro-5H-pyrazolo[4,3-c]azepine-7,4'-tetrahydropyran]-1-yl)propyl 3,5-diethylisoxazole-4-carboxylate;

(xcviii) 3-(3-ethyl-4-oxo-spiro[6,8-dihydro-5H-pyrazolo[4,3-c]azepine-7,4'-tetrahydropyran]-1-yl)propyl 1-acetylpiperidine-3-carboxylate;

(xcix) 3-(3-ethyl-4-oxo-spiro[6,8-dihydro-5H-pyrazolo[4,3-c]azepine-7,4'-tetrahydropyran]-1-yl)propyl 1-acetylpiperidine-4-carboxylate;

(c) 3-(3-ethyl-4-oxo-spiro[6,8-dihydro-5H-pyrazolo[4,3-c]azepine-7,4'-tetrahydropyran]-1-yl)propyl 2-methoxy-4-methyl-thiazole-5-carboxylate;

(ci) 3-(3-ethyl-4-oxo-spiro[6,8-dihydro-5H-pyrazolo[4,3-c]azepine-7,4'-tetrahydropyran]-1-yl)propyl 3-methyl-benzimidazole-5-carboxylate;

(cii) 3-(3-ethyl-4-oxo-spiro[6,8-dihydro-5H-pyrazolo[4,3-c]azepine-7,4'-tetrahydropyran]-1-yl)propyl 1,1-dioxothiane-3-carboxylate;

(ciii) 3-(3-ethyl-4-oxo-spiro[6,8-dihydro-5H-pyrazolo[4,3-c]azepine-7,4'-tetrahydropyran]-1-yl)propyl 1,1-dioxothiane-4-carboxylate;

(civ) O3-[3-(3-ethyl-4-oxo-spiro[6,8-dihydro-5H-pyrazolo[4,3-c]azepine-7,4'-tetrahydropyran]-1-yl)propyl] O1-methyl piperidine-1,3-dicarboxylate;

(cv) O4-[3-(3-ethyl-4-oxo-spiro[6,8-dihydro-5H-pyrazolo[4,3-c]azepine-7,4'-tetrahydropyran]-1-yl)propyl] O1-methyl piperidine-1,4-dicarboxylate;

(cvi) 3-(3-ethyl-4-oxo-spiro[6,8-dihydro-5H-pyrazolo[4,3-c]azepine-7,4'-tetrahydropyran]-1-yl)propyl 1-(dimethylcarbamoyl)piperidine-3-carboxylate;

(cvii) 3-(3-ethyl-4-oxo-spiro[6,8-dihydro-5H-pyrazolo[4,3-c]azepine-7,4'-tetrahydropyran]-1-yl)propyl 1-(dimethylcarbamoyl)piperidine-4-carboxylate;

(cviii) [(2R)-3-(3-ethyl-4-oxo-spiro[6,8-dihydro-5H-pyrazolo[4,3-c]azepine-7,4'-tetrahydropyran]-1-yl)-2-methyl-propyl] tetrahydrofuran-3-carboxylate;

(cix) [(2R)-3-(3-ethyl-4-oxo-spiro[6,8-dihydro-5H-pyrazolo[4,3-c]azepine-7,4'-tetrahydropyran]-1-yl)-2-methyl-propyl] tetrahydropyran-4-carboxylate;

(cx) [3-(3-ethyl-4-oxo-spiro[6,8-dihydro-5H-pyrazolo[4,3-c]azepine-7,4'-tetrahydropyran]-1-yl)-2,2-dimethyl-propyl] tetrahydrofuran-3-carboxylate;

(cxi) [3-(3-ethyl-4-oxo-spiro[6,8-dihydro-5H-pyrazolo[4,3-c]azepine-7,4'-tetrahydropyran]-1-yl)-2,2-dimethyl-propyl] tetrahydropyran-4-carboxylate;

(cxii) 4-(3-ethyl-4-oxo-spiro[6,8-dihydro-5H-pyrazolo[4,3-c]azepine-7,4'-tetrahydropyran]-1-yl)butyl 2-methyl-oxazole-5-carboxylate;

(cxiii) 4-(3-ethyl-4-oxo-spiro[6,8-dihydro-5H-pyrazolo[4,3-c]azepine-7,4'-tetrahydropyran]-1-yl)butyl isothiazole-4-carboxylate;

(cxiv) 4-(3-ethyl-4-oxo-spiro[6,8-dihydro-5H-pyrazolo[4,3-c]azepine-7,4'-tetrahydropyran]-1-yl)butyl thiazole-4-carboxylate;

(cxv) 4-(3-ethyl-4-oxo-spiro[6,8-dihydro-5H-pyrazolo[4,3-c]azepine-7,4'-tetrahydropyran]-1-yl)butyl tetrahydropyran-4-carboxylate;

or a pharmaceutically acceptable salt, hydrate or solvate thereof.

8. A pharmaceutical composition comprising a compound according to claim 1 and one or more pharmaceutically acceptable vehicles or excipients and/or pharmaceutically acceptable carriers.

9. The pharmaceutical composition according to claim 8 further comprising one or more other therapeutically active compounds.

* * * * *